US012653672B2

(12) United States Patent
Hamill et al.

(10) Patent No.: US 12,653,672 B2
(45) Date of Patent: Jun. 16, 2026

(54) PERICARDIAL ANCHORING SYSTEM

(71) Applicant: Pipeline Medical Technologies, Inc., Santa Rosa, CA (US)

(72) Inventors: Whittaker I. Hamill, Santa Rosa, CA (US); Todd J. Johnson, Flagstaff, AZ (US); Stephen R. McDaniel, San Rafael, CA (US); Cameron Paul Purcell, Santa Rosa, CA (US); Katie Nicole Riojas, Santa Rosa, CA (US); Kip J. Wetter, Petaluma, CA (US); Paul Sorajja, Minneapolis, MN (US)

(73) Assignee: Pipeline Medical Technologies, Inc., Newark, DE (US)

( * ) Notice: Subject to any disclaimer, the term of this patent is extended or adjusted under 35 U.S.C. 154(b) by 909 days.

(21) Appl. No.: 17/728,838

(22) Filed: Apr. 25, 2022

(65) Prior Publication Data

US 2022/0338990 A1 Oct. 27, 2022

Related U.S. Application Data

(60) Provisional application No. 63/182,375, filed on Apr. 30, 2021, provisional application No. 63/182,727, (Continued)

(51) Int. Cl.
*A61B 17/00* (2006.01)
*A61B 17/04* (2006.01)
(Continued)

(52) U.S. Cl.
CPC ........ *A61F 2/2457* (2013.01); *A61B 17/0401* (2013.01); *A61F 2/2454* (2013.01); *A61F 2/2466* (2013.01); *A61B 2017/0406* (2013.01);

*A61B 2017/0409* (2013.01); *A61B 2017/3488* (2013.01); *A61F 2220/0008* (2013.01)

(58) Field of Classification Search
CPC .... A61F 2/2457; A61F 2/2454; A61F 2/2442; A61F 2/2445; A61B 2017/0401; A61B 2017/0446; A61B 2017/0448; A61B 2017/0406; A61B 17/0401
See application file for complete search history.

(56) References Cited

U.S. PATENT DOCUMENTS

| | | | |
|---|---|---|---|
| 3,895,632 A | 7/1975 | Plowiecki | |
| 5,329,923 A | 7/1994 | Lundquist | |
| (Continued) | | | |

FOREIGN PATENT DOCUMENTS

| | | |
|---|---|---|
| CN | 101495049 | 7/2009 |
| CN | 101553190 | 10/2009 |
| (Continued) | | |

OTHER PUBLICATIONS

International Preliminary Report on Patentability received for PCT Patent Application No. PCT/US22/26227, mailed on Nov. 9, 2023, 18 pages.

(Continued)

*Primary Examiner* — Sarah W Aleman
*Assistant Examiner* — Paris Marie Blass

(57) ABSTRACT

Various aspects of the present disclosure are directed toward apparatuses, systems, and methods for cardiac device anchoring and more specifically to accessing and anchoring in the pericardial space.

21 Claims, 42 Drawing Sheets

Related U.S. Application Data filed on Apr. 30, 2021, provisional application No. 63/179,490, filed on Apr. 25, 2021.

(51) Int. Cl.
  *A61B 17/34* (2006.01)
  *A61F 2/24* (2006.01)

(56) References Cited

U.S. PATENT DOCUMENTS

| | | | |
|---|---|---|---|
| 5,456,708 A | 10/1995 | Doan et al. |
| 5,674,217 A | 10/1997 | Wahlstrom et al. |
| 6,269,819 B1 | 8/2001 | Oz |
| 6,458,107 B1 | 10/2002 | Ockuly |
| 6,461,366 B1 | 10/2002 | Seguin |
| 6,569,105 B1 | 5/2003 | Kortenbach et al. |
| 6,626,930 B1 | 9/2003 | Allen et al. |
| 6,629,534 B1 | 10/2003 | St. Goar et al. |
| 6,743,239 B1 | 6/2004 | Kuehn et al. |
| 6,752,813 B2 | 6/2004 | Goldfarb et al. |
| 6,770,083 B2 | 8/2004 | Seguin |
| 6,840,246 B2 | 1/2005 | Downing |
| 6,978,176 B2 | 12/2005 | Lattouf |
| 7,048,754 B2 | 5/2006 | Martin et al. |
| 7,083,628 B2 | 8/2006 | Bachman |
| 7,191,545 B2 | 3/2007 | Yi |
| 7,226,467 B2 | 6/2007 | Lucatero et al. |
| 7,288,097 B2 | 10/2007 | Seguin |
| 7,464,712 B2 | 12/2008 | Oz et al. |
| 7,563,267 B2 | 7/2009 | Goldfarb et al. |
| 7,604,646 B2 | 10/2009 | Goldfarb et al. |
| 7,608,091 B2 | 10/2009 | Goldfarb et al. |
| 7,632,308 B2 | 12/2009 | Loulmet |
| 7,635,386 B1 | 12/2009 | Gammie |
| 7,637,903 B2 | 12/2009 | Lentz et al. |
| 7,655,015 B2 | 2/2010 | Goldfarb et al. |
| 7,666,204 B2 | 2/2010 | Thornton et al. |
| 7,682,369 B2 | 3/2010 | Seguin |
| 7,736,388 B2 | 6/2010 | Goldfarb et al. |
| 7,871,368 B2 | 1/2011 | Zollinger et al. |
| 7,871,433 B2 | 1/2011 | Lattouf |
| 7,887,552 B2 | 2/2011 | Bachman |
| 7,914,515 B2 | 3/2011 | Heideman et al. |
| 7,914,545 B2 | 3/2011 | Ek |
| 8,075,570 B2 | 12/2011 | Bolduc et al. |
| 8,100,923 B2 | 1/2012 | Paraschac et al. |
| 8,172,872 B2 | 5/2012 | Osypka |
| 8,241,304 B2 | 8/2012 | Bachman |
| 8,252,050 B2 | 8/2012 | Maisano et al. |
| 8,273,054 B2 | 9/2012 | St. Germain et al. |
| 8,303,622 B2 | 11/2012 | Alkhatib |
| 8,382,829 B1 | 2/2013 | Call et al. |
| 8,409,273 B2 | 4/2013 | Thornton et al. |
| 8,465,500 B2 | 6/2013 | Speziali |
| 8,475,472 B2 | 7/2013 | Bachman |
| 8,475,525 B2 | 7/2013 | Maisano et al. |
| 8,480,730 B2 | 7/2013 | Maurer et al. |
| 8,545,551 B2 | 10/2013 | Loulmet |
| 8,545,553 B2 | 10/2013 | Zipory et al. |
| 8,603,066 B2 | 12/2013 | Heidman et al. |
| 8,690,939 B2 | 4/2014 | Miller et al. |
| 8,718,794 B2 | 5/2014 | Helland |
| 8,740,940 B2 | 6/2014 | Maahs et al. |
| 8,778,016 B2 | 7/2014 | Janovsky et al. |
| 8,814,824 B2 | 8/2014 | Kauphusman et al. |
| 8,852,213 B2 | 10/2014 | Gammie et al. |
| 8,940,042 B2 | 1/2015 | Miller et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,594 B2 | 2/2015 | Maisano et al. |
| 8,961,596 B2 | 2/2015 | Maisano et al. |
| 9,011,520 B2 | 4/2015 | Miller et al. |
| 9,023,065 B2 | 5/2015 | Bolduc et al. |
| 9,050,187 B2 | 6/2015 | Sugimoto et al. |
| 9,131,939 B1 | 9/2015 | Call et al. |
| 9,180,007 B2 | 11/2015 | Reich et al. |
| 9,198,649 B2 | 12/2015 | Karapetian et al. |
| 9,241,702 B2 | 1/2016 | Maisano et al. |
| 9,259,218 B2 | 2/2016 | Robinson |
| 9,277,994 B2 | 3/2016 | Miller et al. |
| 9,307,980 B2 | 4/2016 | Gilmore et al. |
| 9,314,242 B2 | 4/2016 | Bachman |
| 9,474,606 B2 | 10/2016 | Zipory et al. |
| 9,492,264 B2 | 11/2016 | Fifer et al. |
| 9,572,667 B2 | 2/2017 | Solem |
| 9,636,205 B2 | 5/2017 | Lee et al. |
| 9,636,224 B2 | 5/2017 | Zipory et al. |
| 9,668,860 B2 | 6/2017 | Kudlik et al. |
| 9,681,864 B1 | 6/2017 | Gammie et al. |
| 9,681,964 B2 | 6/2017 | MacKenzie |
| 9,693,865 B2 | 7/2017 | Gilmore et al. |
| 9,724,195 B2 | 8/2017 | Goodwin et al. |
| 9,750,493 B2 | 9/2017 | Robinson et al. |
| 9,788,948 B2 | 10/2017 | Gilmore et al. |
| 9,801,720 B2 | 10/2017 | Gilmore et al. |
| 9,814,454 B2 | 11/2017 | Sugimoto et al. |
| 9,877,833 B1 | 1/2018 | Bishop et al. |
| 9,907,547 B2 | 3/2018 | Gilmore et al. |
| 9,907,681 B2 | 3/2018 | Tobis et al. |
| 10,022,114 B2 | 7/2018 | Gilmore et al. |
| 10,039,643 B2 | 8/2018 | Gilmore et al. |
| 10,039,644 B2 | 8/2018 | Navia et al. |
| 10,052,095 B2 | 8/2018 | Gilmore et al. |
| 10,058,323 B2 | 8/2018 | Maisano |
| 10,076,327 B2 | 9/2018 | Ellis et al. |
| 10,076,658 B2 | 9/2018 | Hastings et al. |
| 10,130,791 B2 | 11/2018 | Heideman et al. |
| 10,159,571 B2 | 12/2018 | de Canniere |
| 10,206,673 B2 | 2/2019 | Maisano et al. |
| 10,231,727 B2 | 3/2019 | Sutherland et al. |
| 10,238,491 B2 | 3/2019 | Tobis |
| 10,285,686 B2 | 5/2019 | Gammie et al. |
| 10,543,090 B2 | 1/2020 | Griswold et al. |
| 10,548,733 B2 | 2/2020 | Purcell et al. |
| 10,595,994 B1 | 3/2020 | Christianson et al. |
| 10,617,523 B2 | 4/2020 | Purcell et al. |
| 10,624,743 B2 | 4/2020 | Keidar et al. |
| 10,660,753 B2 | 5/2020 | Pham et al. |
| 10,667,910 B2 | 6/2020 | Bishop et al. |
| 10,675,150 B2 | 6/2020 | Bishop et al. |
| 10,682,230 B2 | 6/2020 | Bishop et al. |
| 10,925,731 B2 | 2/2021 | Bishop et al. |
| 11,083,580 B2 | 8/2021 | Purcell et al. |
| 2003/0105519 A1 | 6/2003 | Fasol et al. |
| 2003/0120341 A1 | 6/2003 | Shennib et al. |
| 2003/0130598 A1 | 7/2003 | Manning et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0073216 A1 | 4/2004 | Lieberman |
| 2004/0097979 A1 | 5/2004 | Svanidze et al. |
| 2005/0119735 A1 | 6/2005 | Spence et al. |
| 2005/0177132 A1 | 8/2005 | Lentz et al. |
| 2005/0177180 A1 | 8/2005 | Kaganov et al. |
| 2007/0038230 A1 | 2/2007 | Stone et al. |
| 2007/0118151 A1 | 5/2007 | Davidson |
| 2007/0123979 A1 | 5/2007 | Perier et al. |
| 2007/0219565 A1 | 9/2007 | Saadat |
| 2008/0177281 A1 | 7/2008 | Weitzner et al. |
| 2008/0177304 A1 | 7/2008 | Westra et al. |
| 2008/0195126 A1 | 8/2008 | Solem |
| 2008/0228165 A1 | 9/2008 | Spence et al. |
| 2008/0228223 A1 | 9/2008 | Alkhatib |
| 2008/0288061 A1 | 11/2008 | Maurer et al. |
| 2008/0294188 A1 | 11/2008 | Appling et al. |
| 2009/0043153 A1 | 2/2009 | Zollinger et al. |
| 2009/0069847 A1 | 3/2009 | Hashiba et al. |
| 2009/0082828 A1 | 3/2009 | Ostroff |
| 2009/0088837 A1 | 4/2009 | Gillinov et al. |
| 2009/0287304 A1 | 11/2009 | Dahlgren et al. |
| 2009/0312790 A1 | 12/2009 | Forsberg et al. |
| 2010/0023118 A1 | 1/2010 | Medlock et al. |
| 2010/0161042 A1 | 6/2010 | Maisano et al. |

(56) References Cited

U.S. PATENT DOCUMENTS

| | | | |
|---|---|---|---|
| 2010/0161043 A1 | 6/2010 | Maisano et al. | |
| 2010/0249919 A1 | 9/2010 | Gillinov et al. | |
| 2010/0280604 A1 | 11/2010 | Zipory et al. | |
| 2011/0011917 A1 | 1/2011 | Loulmet | |
| 2011/0022083 A1 | 1/2011 | DiMatteo et al. | |
| 2011/0029071 A1* | 2/2011 | Zlotnick | A61B 17/00234 |
| | | | 623/2.11 |
| 2011/0060407 A1 | 3/2011 | Ketai et al. | |
| 2011/0106245 A1 | 5/2011 | Miller et al. | |
| 2011/0301698 A1 | 12/2011 | Miller et al. | |
| 2012/0065464 A1 | 3/2012 | Ellis et al. | |
| 2012/0116418 A1 | 5/2012 | Belson et al. | |
| 2012/0116489 A1 | 5/2012 | Khairkhahan et al. | |
| 2012/0158021 A1 | 6/2012 | Morrill | |
| 2012/0172915 A1 | 7/2012 | Fifer et al. | |
| 2013/0035757 A1 | 2/2013 | Zentgraf et al. | |
| 2013/0046380 A1 | 2/2013 | Maisano et al. | |
| 2013/0096672 A1 | 4/2013 | Reich et al. | |
| 2013/0190741 A1 | 7/2013 | Moll et al. | |
| 2013/0197575 A1 | 8/2013 | Karapetian et al. | |
| 2013/0197577 A1 | 8/2013 | Wolf et al. | |
| 2013/0197578 A1 | 8/2013 | Gregoire et al. | |
| 2013/0253639 A1 | 9/2013 | Alkhatib | |
| 2014/0142687 A1 | 5/2014 | De Canniere et al. | |
| 2014/0142689 A1 | 5/2014 | De Canniere et al. | |
| 2014/0243877 A9 | 8/2014 | Lee et al. | |
| 2014/0243963 A1 | 8/2014 | Sheps et al. | |
| 2014/0350417 A1 | 11/2014 | Van Bladel et al. | |
| 2015/0119979 A1 | 4/2015 | Maisano et al. | |
| 2015/0182255 A1 | 7/2015 | Shivkumar | |
| 2015/0230919 A1 | 8/2015 | Chau et al. | |
| 2015/0250590 A1 | 9/2015 | Gries et al. | |
| 2015/0289815 A1 | 10/2015 | Sham et al. | |
| 2015/0313620 A1 | 11/2015 | Suri | |
| 2015/0342737 A1 | 12/2015 | Biancucci et al. | |
| 2015/0359632 A1 | 12/2015 | Navia et al. | |
| 2016/0058557 A1 | 3/2016 | Reich et al. | |
| 2016/0143737 A1 | 5/2016 | Zentgraf et al. | |
| 2016/0174964 A1 | 6/2016 | Tobis | |
| 2016/0192925 A1 | 7/2016 | Bachman | |
| 2016/0228117 A1 | 8/2016 | Borden | |
| 2016/0240941 A1 | 8/2016 | Stavrianoudakis | |
| 2016/0256269 A1* | 9/2016 | Cahalane | A61B 17/0057 |
| 2016/0262741 A1 | 9/2016 | Gilmore et al. | |
| 2016/0310701 A1 | 10/2016 | Pai | |
| 2016/0354082 A1 | 12/2016 | Oz et al. | |
| 2016/0367367 A1 | 12/2016 | Maisano et al. | |
| 2017/0042658 A1 | 2/2017 | Lee et al. | |
| 2017/0079797 A1 | 3/2017 | Maisano et al. | |
| 2017/0086975 A1 | 3/2017 | Gilmore et al. | |
| 2017/0119368 A1 | 5/2017 | Solem | |
| 2017/0135817 A1* | 5/2017 | Tylis | A61F 2/2445 |
| 2017/0156719 A1 | 6/2017 | Tobis | |
| 2017/0156861 A1 | 6/2017 | Longoria et al. | |
| 2017/0202657 A1 | 7/2017 | Lee et al. | |
| 2017/0202669 A1 | 7/2017 | Schaffner et al. | |
| 2017/0252032 A1 | 9/2017 | Hiorth et al. | |
| 2017/0258464 A1 | 9/2017 | Gammie et al. | |
| 2017/0258588 A1 | 9/2017 | Zipory et al. | |
| 2017/0258594 A1 | 9/2017 | Gilmore et al. | |
| 2017/0273681 A1 | 9/2017 | Gilmore et al. | |
| 2017/0304051 A1 | 10/2017 | Tobis et al. | |
| 2017/0340433 A1 | 11/2017 | Berra et al. | |
| 2017/0340443 A1 | 11/2017 | Stearns et al. | |
| 2018/0064535 A1 | 3/2018 | Gilmore et al. | |
| 2018/0185150 A1 | 7/2018 | Bishop et al. | |
| 2018/0185179 A1 | 7/2018 | Murphy et al. | |
| 2018/0206992 A1 | 7/2018 | Brown | |
| 2018/0221148 A1 | 8/2018 | Guidotti et al. | |
| 2018/0249993 A1 | 9/2018 | Denti et al. | |
| 2018/0289480 A1 | 10/2018 | D'ambra et al. | |
| 2018/0303614 A1 | 10/2018 | Schaffner et al. | |
| 2018/0311007 A1 | 11/2018 | Tyler, II et al. | |
| 2018/0318079 A1 | 11/2018 | Patel et al. | |
| 2018/0318083 A1 | 11/2018 | Bolling et al. | |
| 2018/0344311 A1 | 12/2018 | Gilmore et al. | |
| 2018/0353297 A1 | 12/2018 | Griffin | |
| 2018/0360439 A1 | 12/2018 | Niland et al. | |
| 2019/0000624 A1 | 1/2019 | Wilson et al. | |
| 2019/0015205 A1 | 1/2019 | Rajagopal et al. | |
| 2019/0069891 A1 | 3/2019 | Gilmore et al. | |
| 2019/0083085 A1 | 3/2019 | Gilmore et al. | |
| 2019/0105027 A1 | 4/2019 | Gilmore et al. | |
| 2019/0117401 A1 | 4/2019 | Cortez, Jr. et al. | |
| 2019/0151090 A1 | 5/2019 | Gross et al. | |
| 2019/0175345 A1 | 6/2019 | Schaffner et al. | |
| 2019/0175346 A1 | 6/2019 | Schaffner et al. | |
| 2019/0183480 A1 | 6/2019 | Hiorth et al. | |
| 2019/0183648 A1 | 6/2019 | Trapp et al. | |
| 2019/0216599 A1 | 7/2019 | Alkhatib | |
| 2019/0216601 A1* | 7/2019 | Purcell | A61F 2/2454 |
| 2019/0240023 A1 | 8/2019 | Spence et al. | |
| 2019/0314155 A1 | 10/2019 | Franklin et al. | |
| 2019/0328530 A1 | 10/2019 | McDaniel et al. | |
| 2019/0365539 A1 | 12/2019 | Rabito et al. | |
| 2019/0380699 A1 | 12/2019 | Bak-Boychuk et al. | |
| 2020/0155798 A1 | 5/2020 | Yang et al. | |
| 2020/0297489 A1 | 9/2020 | Bishop et al. | |
| 2020/0330228 A1 | 10/2020 | Anderson et al. | |
| 2020/0345496 A1 | 11/2020 | Bishop et al. | |
| 2020/0390554 A1 | 12/2020 | Pham et al. | |
| 2021/0186699 A1 | 6/2021 | Bishop et al. | |
| 2021/0213259 A1 | 7/2021 | Giasolli et al. | |
| 2022/0339437 A1 | 10/2022 | Sorajja | |

FOREIGN PATENT DOCUMENTS

| | | |
|---|---|---|
| CN | 101184454 | 10/2010 |
| CN | 101902975 | 12/2010 |
| CN | 103491901 | 1/2014 |
| CN | 103635160 | 3/2014 |
| CN | 103813757 | 5/2014 |
| CN | 103889345 | 6/2014 |
| CN | 104000625 | 8/2014 |
| CN | 104582637 | 4/2015 |
| CN | 105555229 | 5/2016 |
| CN | 107569301 | 1/2018 |
| EP | 1 898 802 | 9/2015 |
| EP | 2 979 647 | 2/2016 |
| EP | 3562410 | 11/2019 |
| JP | 2014-523282 | 9/2014 |
| RU | 2219853 | 12/2003 |
| WO | WO 2007/061834 | 5/2007 |
| WO | WO 2007/100268 | 9/2007 |
| WO | WO 2008/005747 | 1/2008 |
| WO | WO 2010/128502 | 11/2010 |
| WO | WO 2012/040865 | 4/2012 |
| WO | WO 2013/179295 | 12/2013 |
| WO | WO 2014/134185 | 9/2014 |
| WO | WO 2017/066888 | 4/2017 |
| WO | WO 2017/066889 | 4/2017 |
| WO | WO 2017/066890 | 4/2017 |
| WO | WO 2017/117560 | 7/2017 |
| WO | WO 2018/035378 | 2/2018 |
| WO | WO 2018/126188 | 7/2018 |
| WO | WO 2018/148324 | 8/2018 |
| WO | WO 2018/148364 | 8/2018 |
| WO | WO 2018/160456 | 9/2018 |
| WO | WO 2018/227048 | 12/2018 |
| WO | WO 2019/013994 | 1/2019 |
| WO | WO 2019/074815 | 4/2019 |
| WO | WO 2019/177909 | 9/2019 |
| WO | WO 2019/195860 | 10/2019 |
| WO | WO 2019/231744 | 12/2019 |
| WO | WO 2019/236654 | 12/2019 |
| WO | WO 2020/106705 | 5/2020 |
| WO | WO 2020/109594 | 6/2020 |
| WO | WO 2020/109596 | 6/2020 |
| WO | WO 2020/109599 | 6/2020 |
| WO | WO 2020/123719 | 6/2020 |
| WO | WO 2020/219281 | 10/2020 |
| WO | WO-2020219281 A1 * | 10/2020 ......... A61B 17/0401 |

(56)            References Cited

FOREIGN PATENT DOCUMENTS

| WO | WO 2020/256853 | 12/2020 | |
| WO | WO-2021195460 A1 * | 9/2021 | ......... A61B 17/0401 |
| WO | WO 2021/257278 | 12/2021 | |

OTHER PUBLICATIONS

Invitation to Pay Additional Fee received for PCT Patent Application No. PCT/US22/26227, mailed on Aug. 9, 2022, 14 pages.
International Search Report and Written Opinion received in PCT Application No. PCT/US2016/069567, dated Mar. 23, 2017 in 13 pages.
International Search Report and Written Opinion received in PCT Application No. PCT/US2017/069046, dated Jun. 14, 2018 in 11 pages.
International Search Report and Written Opinion received in PCT Application No. PCT/US2019/021480, dated Jul. 15, 2019 in 16 pages.
International Search Report and Written Opinion received in PCT Application No. PCT/US2019/065814, dated Apr. 1, 2020 in 14 pages.

International Search Report and Written Opinion received in PCT Application No. PCT/US2021/035423, dated Oct. 6, 2021 in 20 pages.
Carpentier, M.D., Alain, "Cardiac Valve Surgery—the 'French Correction'", The Journal of Thoracic and Cardiovascular Surgery, Sep. 1983, vol. 86, No. 3, pp. 323-337.
Júnior, Francisco Gregori et al., "Surgical Repair of Chordae Tendineae Rupture After Degenerative Valvular Regurgitation Using Standardized Bovine Pericardium", Revista Brasileira de Cirurgia Cardiovascular, Jan. 2013, vol. 28, No. 1, pp. 36-46.
Kobayashi et al., "Ten Year Experience of Chordal Replacement with Expanded Polytetrafluoroethylene in Mitral Valve Repair", Circulation, American Heart Association, Nov. 7, 2000, pp. III-30-34.
Shikata et al., "Repair of Congenitally Absent Chordae in a Tricuspid Valve Leaflet with Hypoplastic Papillary Muscle Using Artificial Chordae", J Card Surg, 25:737-739 (2010).
International Search Report and Written Opinion received in PCT Application No. PCT/US2022/026227, dated Oct. 19, 2022, in 28 pages.

* cited by examiner

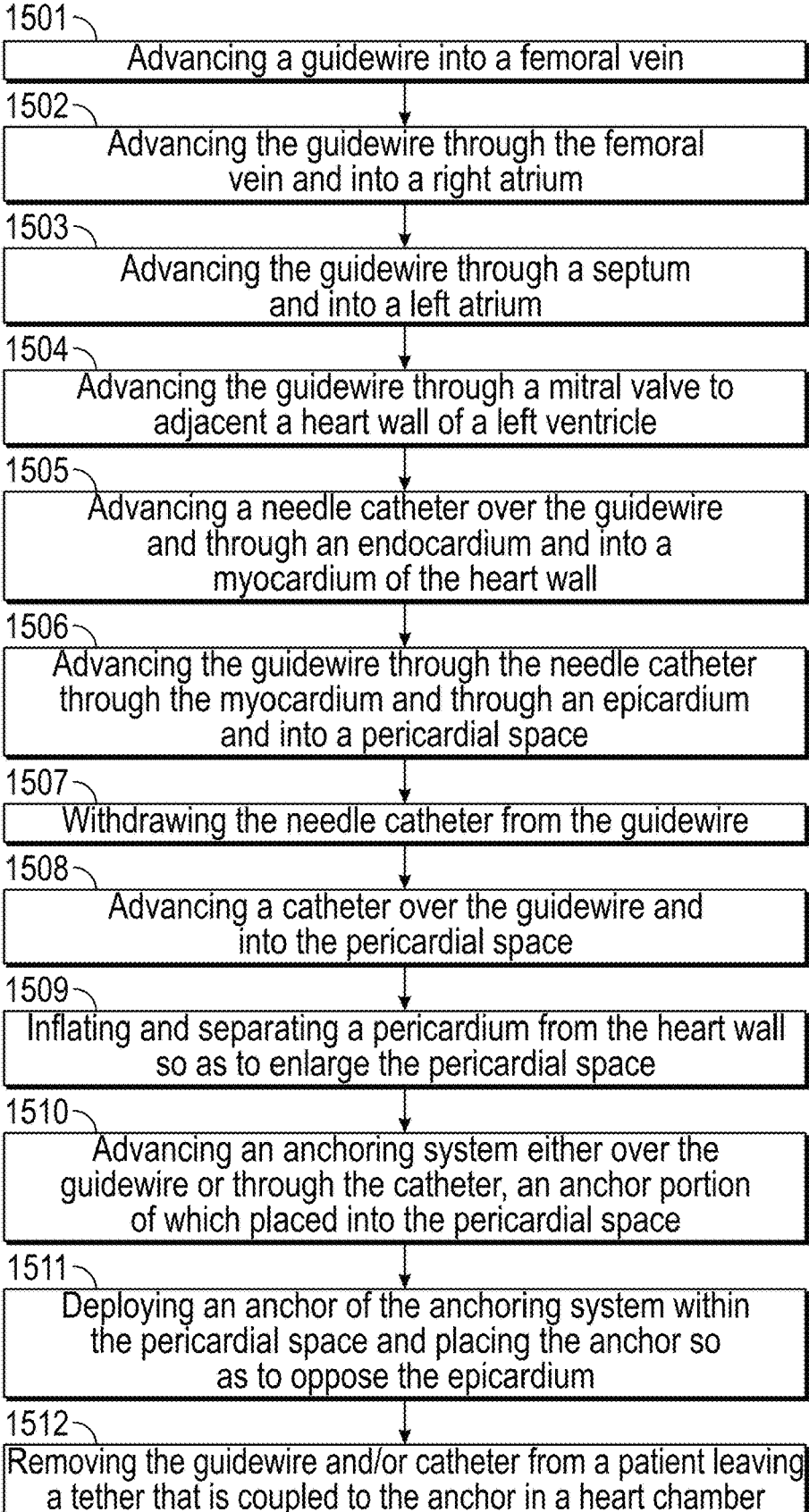

1501 — Advancing a guidewire into a femoral vein

1502 — Advancing the guidewire through the femoral vein and into a right atrium

1503 — Advancing the guidewire through a septum and into a left atrium

1504 — Advancing the guidewire through a mitral valve to adjacent a heart wall of a left ventricle 1505 — Advancing a needle catheter over the guidewire and through an endocardium and into a myocardium of the heart wall 1506 — Advancing the guidewire through the needle catheter through the myocardium and through an epicardium and into a pericardial space 1507 — Withdrawing the needle catheter from the guidewire 1508 — Advancing a catheter over the guidewire and into the pericardial space 1509 — Inflating and separating a pericardium from the heart wall so as to enlarge the pericardial space 1510 — Advancing an anchoring system either over the guidewire or through the catheter, an anchor portion of which placed into the pericardial space 1511 — Deploying an anchor of the anchoring system within the pericardial space and placing the anchor so as to oppose the epicardium 1512 — Removing the guidewire and/or catheter from a patient leaving a tether that is coupled to the anchor in a heart chamber

FIG. 15

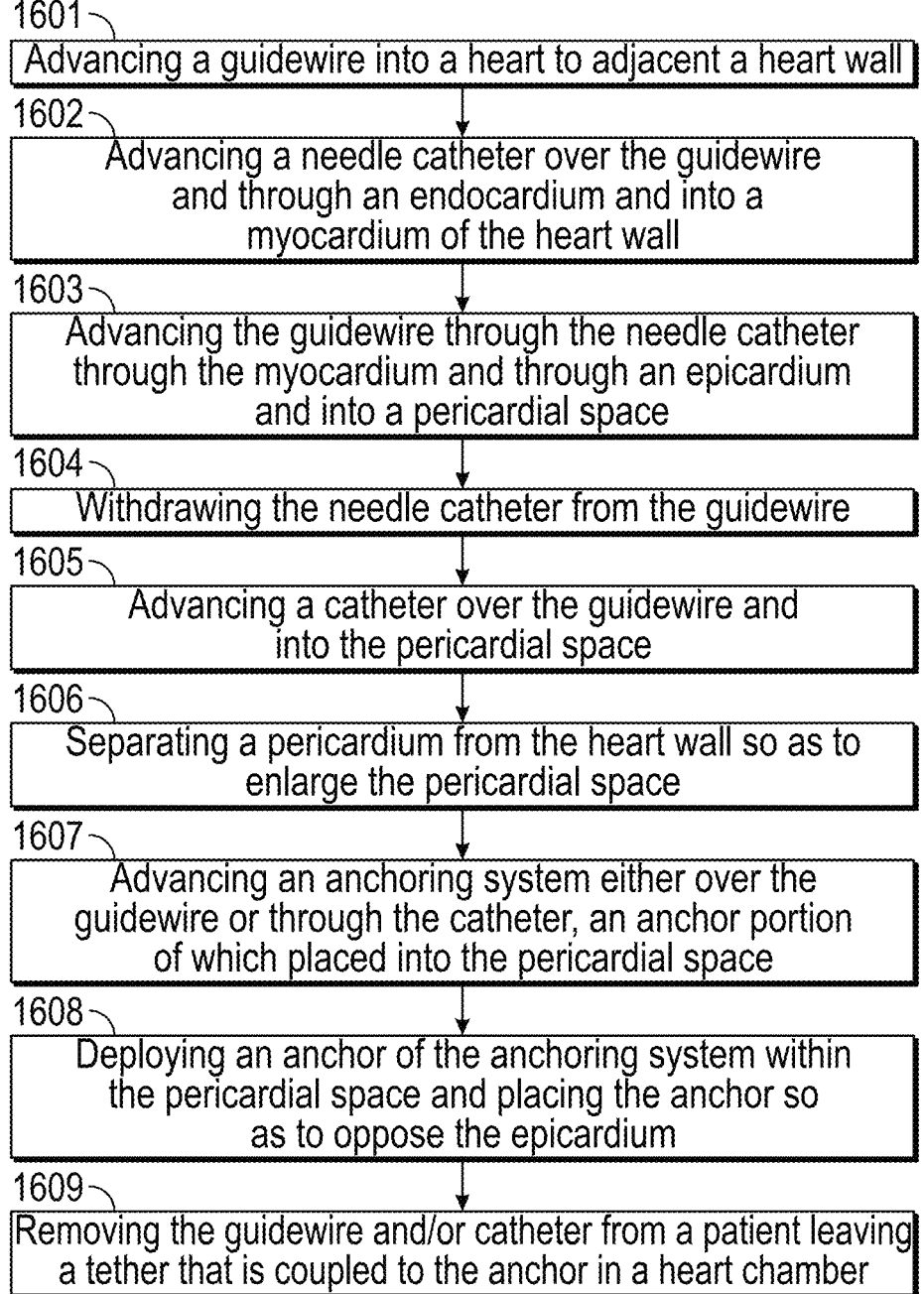

1601 — Advancing a guidewire into a heart to adjacent a heart wall

1602 — Advancing a needle catheter over the guidewire and through an endocardium and into a myocardium of the heart wall 1603 — Advancing the guidewire through the needle catheter through the myocardium and through an epicardium and into a pericardial space 1604 — Withdrawing the needle catheter from the guidewire 1605 — Advancing a catheter over the guidewire and into the pericardial space 1606 — Separating a pericardium from the heart wall so as to enlarge the pericardial space 1607 — Advancing an anchoring system either over the guidewire or through the catheter, an anchor portion of which placed into the pericardial space 1608 — Deploying an anchor of the anchoring system within the pericardial space and placing the anchor so as to oppose the epicardium 1609 — Removing the guidewire and/or catheter from a patient leaving a tether that is coupled to the anchor in a heart chamber

FIG. 16

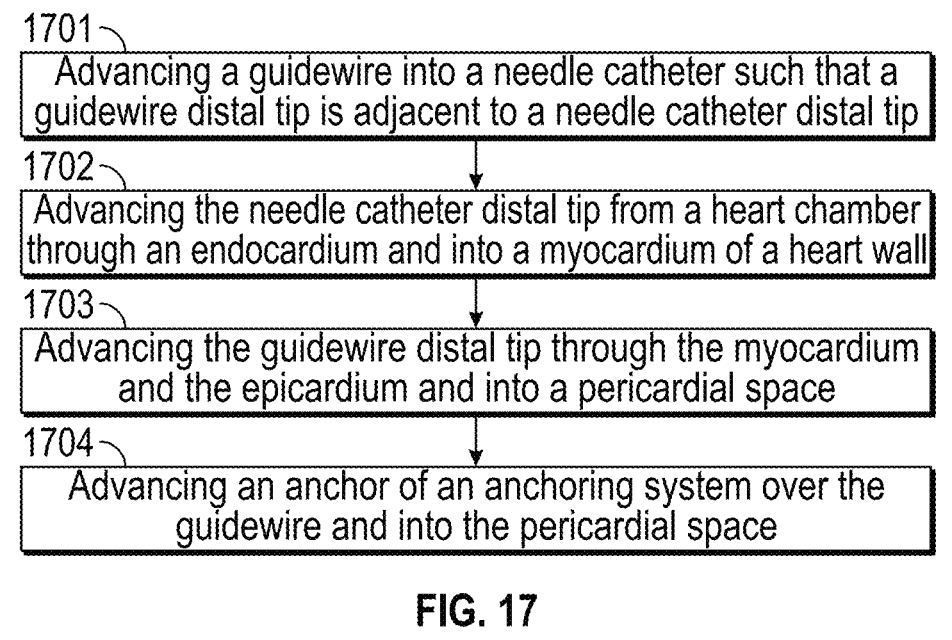

1701
```
Advancing a guidewire into a needle catheter such that a
guidewire distal tip is adjacent to a needle catheter distal tip
```

1702
```
Advancing the needle catheter distal tip from a heart chamber
through an endocardium and into a myocardium of a heart wall
```

1703
```
Advancing the guidewire distal tip through the myocardium
and the epicardium and into a pericardial space
```

1704
```
Advancing an anchor of an anchoring system over the
guidewire and into the pericardial space
```

FIG. 17

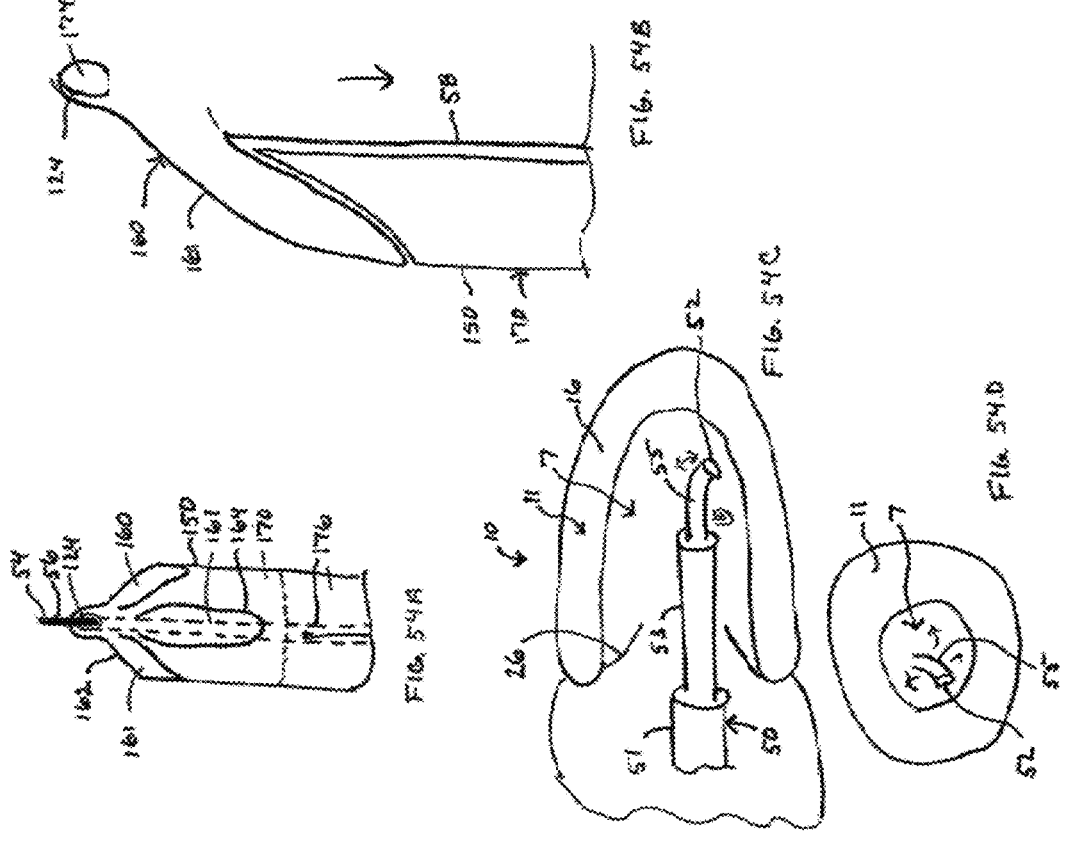

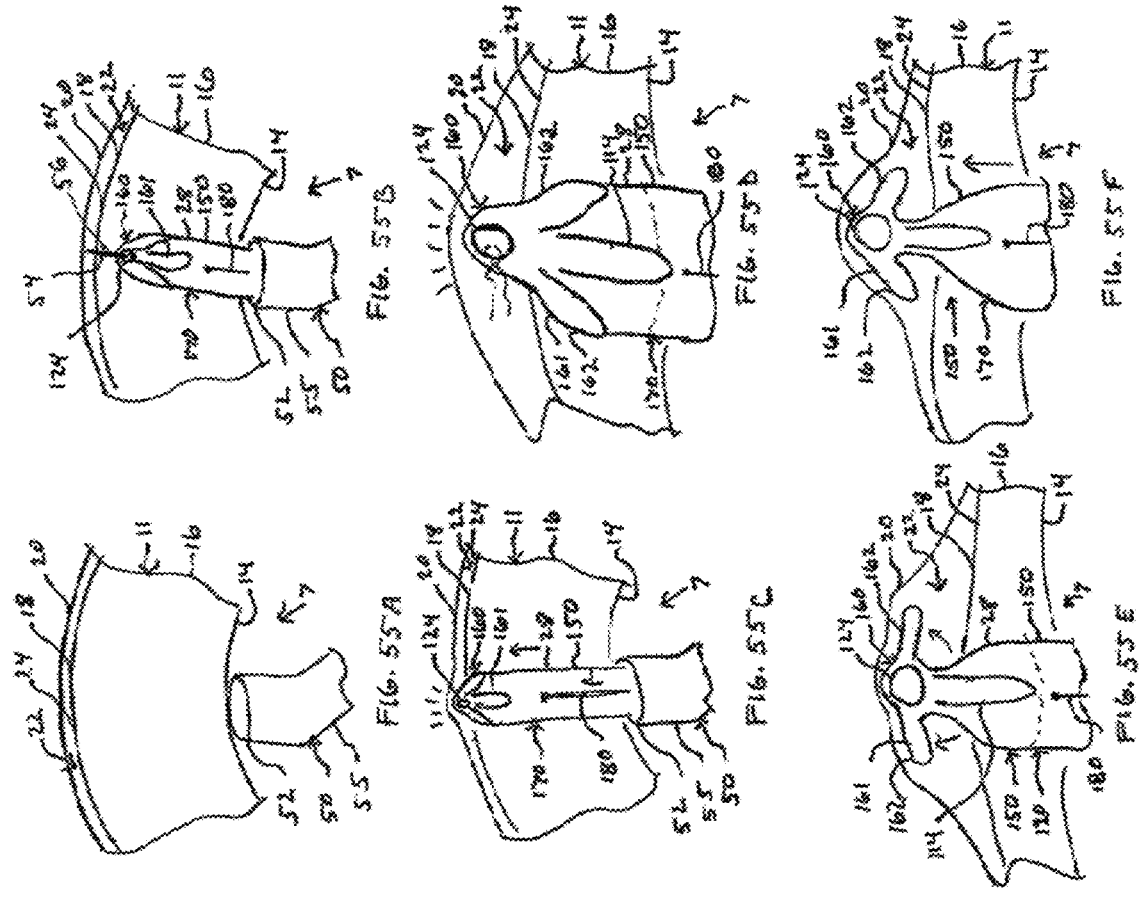

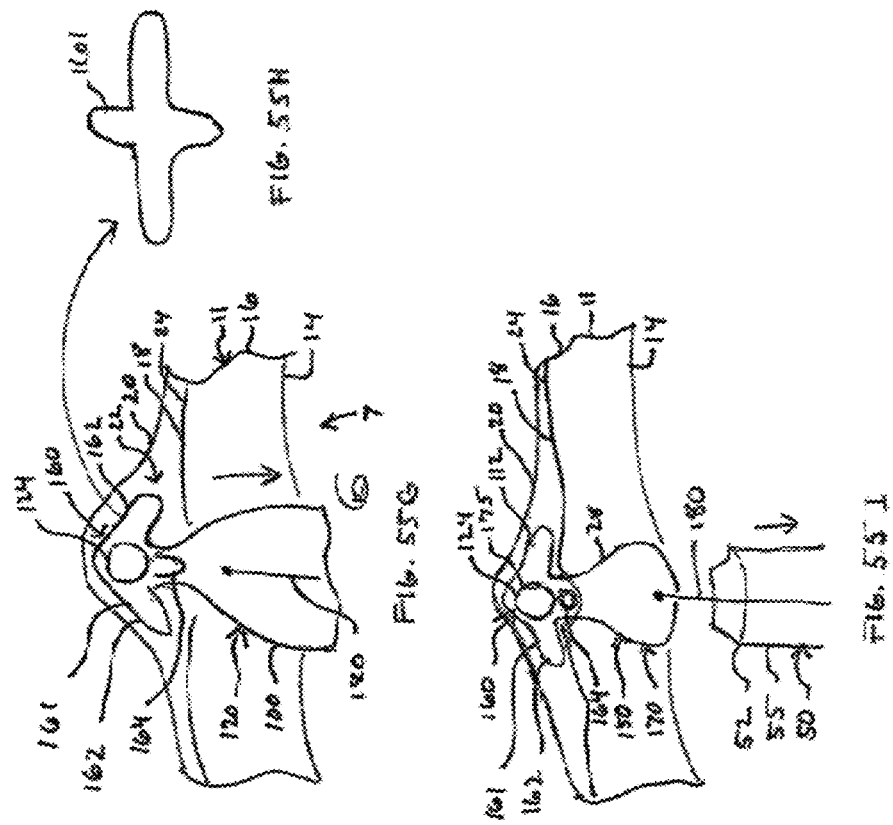

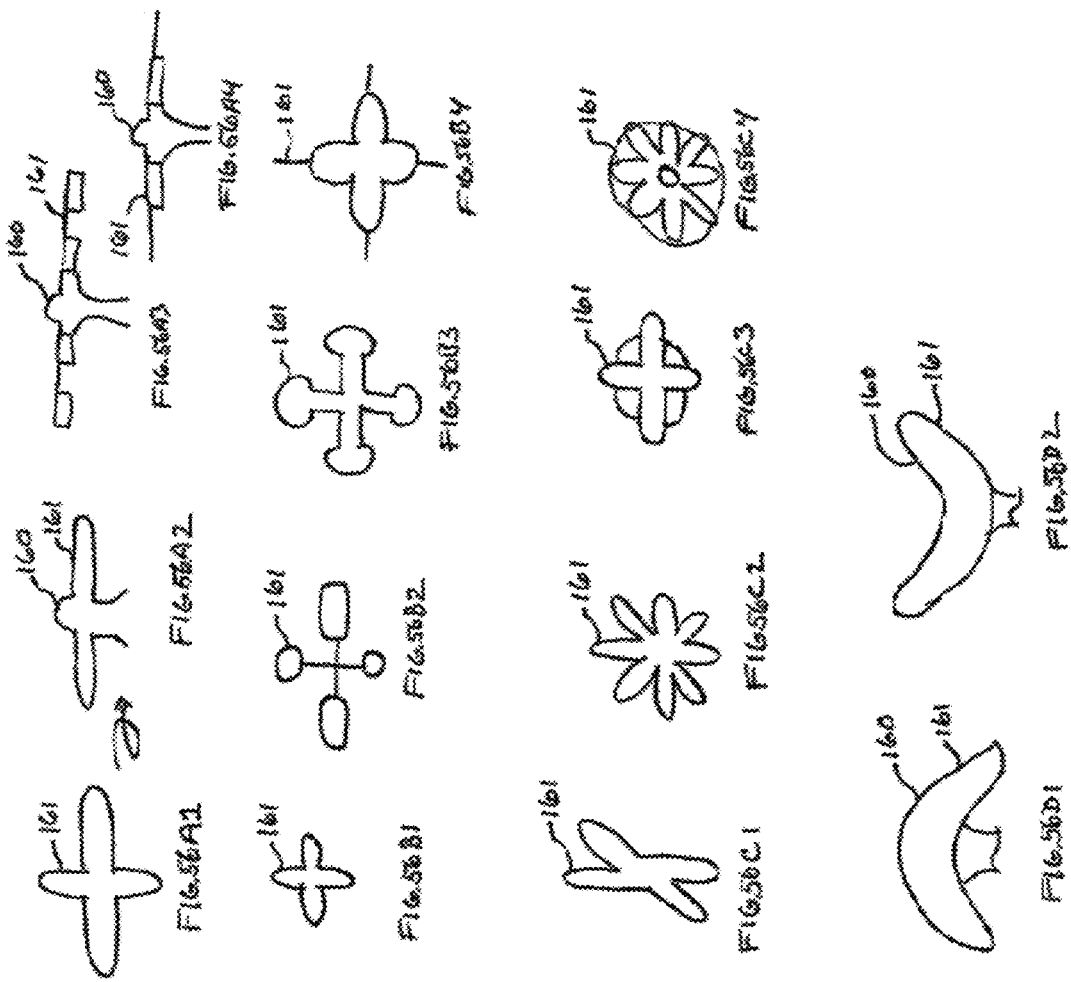

PERICARDIAL ANCHORING SYSTEM

INCORPORATION BY REFERENCE TO ANY PRIORITY APPLICATIONS

This application claims priority to U.S. Provisional Application No. 63/182,727, filed Apr. 30, 2021, and U.S. Provisional Application No. 63/179,490, filed Apr. 25, 2021, the entireties of each of these application are hereby incorporated by reference herein for all purposes.

Any and all applications for which a foreign or domestic priority claim is identified in the Application Data Sheet as filed with the present application are hereby incorporated by reference under 37 CFR 1.57.

FIELD

The present disclosure relates generally to cardiac device anchoring and more specifically to apparatuses, systems, and methods that include accessing and anchoring in the pericardial space.

BACKGROUND

There is a need for anchoring medical devices in the chambers of the heart. Commonly, these devices may have an anchor that is imbedded in the myocardium. There remains a need for a more secure anchoring system for such devices.

SUMMARY

Described embodiments are directed to apparatus, system, and methods for pericardial anchoring.

According to one example ("Example 1"), an anchoring system, comprises an anchor and a tether coupled to the anchor, the anchor operable to have a low profile in a first position and a larger profile in a second position. The anchor is operable to be advanced into a pericardial space from a heart chamber of a heart through a narrow access channel in a heart wall in the first position and expand to the second position in the pericardial space to a size greater than the narrow access channel.

According to another example ("Example 2"), a method of anchoring comprises advancing a guidewire into a heart up to and adjacent a heart wall; advancing a needle catheter over the guidewire and through an endocardium and into a myocardium of the heart wall; advancing the guidewire through the needle catheter through the myocardium and through the epicardium (visceral layer of serous pericardium) and into a pericardial space; withdrawing the needle catheter from the guidewire; advancing a catheter over the guidewire and into the pericardial space; separating the pericardium from the heart wall so as to enlarge the pericardial space; advancing an anchoring system either over the guidewire or through the catheter, an anchor portion of which placed into the pericardial space; deploying an anchor of the anchoring system within the pericardial space and placing the anchor so as to oppose the epicardium; and removing the guidewire and/or catheter from a patient leaving a tether that is coupled to the anchor in a heart chamber.

According to another example ("Example 3"), a method of anchoring comprises advancing a guidewire into a femoral vein; advancing the guidewire through the femoral vein and into the right atrium; advancing the guidewire through a septum and into a left atrium; advancing the guidewire through the mitral valve up to and adjacent a heart wall of a left ventricle; advancing a needle catheter over the guidewire and through an endocardium and into a myocardium of the heart wall; advancing the guidewire through the needle catheter through the myocardium and through an epicardium and into a pericardial space; withdrawing the needle catheter from the guidewire; advancing a catheter over the guidewire and into the pericardial space; inflating and separating the pericardium from the heart wall so as to enlarge the pericardial space; advancing an anchoring system either over the guidewire or through the catheter, an anchor portion of which placed into the pericardial space; deploying an anchor of the anchoring system within the pericardial space and placing the anchor so as to oppose the epicardium; and removing the guidewire and/or catheter from a patient leaving a tether that is coupled to the anchor in a heart chamber.

According to another example ("Example 4"), a method of anchoring comprises advancing a guidewire into a needle catheter such that a guidewire distal tip is adjacent to a needle catheter distal tip; advancing the needle catheter distal tip from a heart chamber through an endocardium and into a myocardium of a heart wall; advancing the guidewire distal tip through the myocardium and the epicardium and into a pericardial space; and advancing an anchor of an anchoring system over the guidewire and into the pericardial space.

In accordance with another example ("Example 5"), a method of anchoring comprises optionally advancing an optional support catheter into a heart up to and adjacent to or against a heart wall; advancing an anchoring catheter singularly or through the optional support catheter and placing in urging engagement against the heart wall, or in close proximity of the heart wall; advancing a guidewire through the anchor catheter through an endocardium through a myocardium and through an epicardium (visceral layer of serous pericardium) of the heart wall and into a pericardial space; advancing the anchor catheter over the guidewire and through the endocardium through the myocardium and through the epicardium (visceral layer of serous pericardium) of the heart wall and into the pericardial space; optionally withdrawing the guidewire from the pericardial space; optionally separating the pericardium from the epicardium so as to enlarge the pericardial space; advancing or exposing an anchor of an anchoring system through or at or near a distal end of the anchor catheter which is in the pericardial space, wherein the anchor is placed into the pericardial space; deploying the anchor of the anchoring system within the pericardial space and placing the anchor so as to oppose the epicardium; and removing the guidewire and/or anchor catheter and/or support catheter from a patient leaving a tether that is coupled to the anchor in a heart chamber.

In accordance with another example ("Example 6"), a method of anchoring comprises advancing an anchor catheter near or up to and against a heart wall in a heart chamber; advancing a guidewire through the anchoring catheter such that a guidewire distal tip advances through an endocardium and into a myocardium through the epicardium and into a pericardial space; and advancing a distal tip of the anchor catheter along or over the guidewire and into or adjacent to the pericardial space; advancing or exposing an anchor of an anchoring system through or at a distal end of the anchor catheter which is in the pericardial space, wherein the anchor is placed in the pericardial space; deploying the anchor of the anchoring system within the pericardial space and placing the anchor so as to oppose the epicardium; and removing the guidewire and/or anchor catheter from a patient leaving a tether that is coupled to the anchor in a heart chamber of an anchoring system over the guidewire and into the pericardial space.

In accordance with another example ("Example 7"), a mitral valve chord repair system, comprises a pericardial anchoring system, including an epicardial anchor comprising a skirt, a transmyocardial pledget, a pericardial anchoring suture coupled to the epicardial anchor and the transmyocardial pledget, a suture lock, and an anchor socket configured to constrain and dock the suture lock, wherein the epicardial anchor is configured to be transformable between a predeployed configuration and a deployed configuration, further including at least one leaflet anchor coupled to a leaflet anchor suture, wherein the suture lock is configured to secure the pericardial anchoring suture and the leaflet anchor suture.

In accordance with another example ("Example 8"), the mitral valve chord repair system of Example 7, wherein the epicardial anchor is configured to form a disc shape in the deployed configuration.

In accordance with another example ("Example 9"), the mitral valve chord repair system of Example 7, wherein the epicardial anchor is configured to form a curved shape, a compressed shape, a bunch, a wad, or a knot in the deployed configuration.

In accordance with another example ("Example 10"), the mitral valve chord repair system of Example 7, wherein the predeployed configuration comprises an elongate configuration, and wherein the deployed configuration comprises a compressed configuration.

In accordance with another example ("Example 11"), the mitral valve chord repair system of Example 7, wherein the predeployed configuration comprises an elongate configuration, and wherein the deployed configuration comprises a coiled configuration.

In accordance with another example ("Example 12"), the mitral valve chord repair system of Example 7, wherein the epicardial anchor has a free end in the predeployed configuration, wherein the epicardial anchor is configured to coil beginning from the free end of the epicardial anchor to form the deployed configuration.

In accordance with another example ("Example 13"), the mitral valve chord repair system of Example 7, wherein the epicardial anchor further comprises a wire frame, wherein the wire frame is covered with the skirt.

In accordance with another example ("Example 14"), the mitral valve chord repair system of Example 13, wherein the wire frame of the epicardial anchor has a shape memory property that is shape-set to the deployed configuration.

In accordance with another example ("Example 15"), the mitral valve chord repair system of Example 13, wherein the skirt is configured to slidingly receive the pericardial anchoring suture, and wherein the pericardial anchoring suture is operable to be tensioned so as to cinch the skirt into the deployed configuration.

In accordance with another example ("Example 16"), the mitral valve chord repair system of Example 13, wherein the skirt of the epicardial anchor is coupled to the wire frame along an edge defining a length, wherein the skirt comprises a plurality of apertures along an edge of the skirt opposite the wire frame, wherein the pericardial anchoring suture is alternately weaved through the plurality of apertures, and wherein the pericardial anchoring suture is operable to be tensioned so as to cinch the skirt into the deployed configuration.

In accordance with another example ("Example 17"), the mitral valve chord repair system of Example 13, wherein the wire frame of the epicardial anchor further comprises a proximal leg, wherein the proximal leg is configured to remain straight and positioned in a center of the epicardial anchor in the deployed configuration.

In accordance with another example ("Example 18"), the mitral valve chord repair system of Example 17, wherein the transmyocardial pledget extends from the proximal leg of the epicardial anchor.

In accordance with another example ("Example 19"), the mitral valve chord repair system of Example 17, wherein the proximal leg includes two portions of the same wire that is doubled up, such that the two portions are parallel to each other.

In accordance with another example ("Example 20"), the mitral valve chord repair system of Example 7, wherein the epicardial anchor is transformable between the predeployed configuration to the deployed configuration at least partially due to proximal retraction of the pericardial anchoring suture.

T In accordance with another example ("Example 21"), the mitral valve chord repair system of Example 13, wherein the epicardial anchor is transformable between the predeployed configuration to the deployed configuration at least partially due to a shape memory property of the wire frame that is shape-set to the deployed configuration.

In accordance with another example ("Example 22"), the mitral valve chord repair system of Example 7, wherein a first end of the wire frame and a second end of the wire frame each comprises a nontraumatic end.

In accordance with another example ("Example 23"), the mitral valve chord repair system of Example 7, wherein the transmyocardial pledget comprises a film with a tubular structure.

In accordance with another example ("Example 24"), the mitral valve chord repair system of Example 23, wherein the pericardial anchoring suture is weaved through a plurality of apertures through the film of the transmyocardial pledget.

In accordance with another example ("Example 25"), the mitral valve chord repair system of Example 7, wherein the anchor socket comprises a self-expanding frame covered with a film.

In accordance with another example ("Example 26"), a pericardial anchoring system, comprises an epicardial anchor comprising a skirt; a transmyocardial pledget extending from a proximal portion of the epicardial anchor; a pericardial anchoring suture coupled to the epicardial anchor and the transmyocardial pledget, a suture lock configured to secure the pericardial anchoring suture; and an anchor socket configured to constrain and dock the suture lock, wherein the epicardial anchor is configured to be transformable between a predeployed configuration and a deployed configuration.

In accordance with another example ("Example 27"), the pericardial anchoring system of Example 26, wherein the epicardial anchor is configured to form a disc shape in the deployed configuration.

In accordance with another example ("Example 28"), the pericardial anchoring system of Example 26, wherein the epicardial anchor is configured to form a curved shape, a compressed shape, a bunch, a wad, or a knot in the deployed configuration.

In accordance with another example ("Example 29"), the pericardial anchoring system of Example 26, wherein the predeployed configuration comprises an elongate configuration, and wherein the deployed configuration comprises a compressed configuration.

In accordance with another example ("Example 30"), the pericardial anchoring system of Example 26, wherein the predeployed configuration comprises an elongate configuration, and wherein the deployed configuration comprises a coiled configuration.

In accordance with another example ("Example 31"), the pericardial anchoring system of Example 26, wherein the epicardial anchor has a free end in the predeployed configuration, wherein the epicardial anchor is configured to coil beginning from the free end of the epicardial anchor to form the deployed configuration.

In accordance with another example ("Example 32"), the pericardial anchoring system of Example 26, wherein the epicardial anchor further comprises a wire frame, wherein the wire frame is covered with the skirt.

In accordance with another example ("Example 33"), the pericardial anchoring system of Example 32, wherein the wire frame of the epicardial anchor has a shape memory property that is shape-set to the deployed configuration.

In accordance with another example ("Example 34"), the pericardial anchoring system of Example 26, wherein the skirt is configured to slidingly receive the pericardial anchoring suture, and wherein the pericardial anchoring suture is operable to be tensioned so as to cinch the skirt into the deployed configuration.

In accordance with another example ("Example 35"), the pericardial anchoring system of Example 32, wherein the skirt of the epicardial anchor is coupled to the wire frame along an edge defining a length, wherein the skirt comprises a plurality of apertures along an edge of the skirt opposite the wire frame, wherein the pericardial anchoring suture is alternately weaved through the plurality of apertures, and wherein the pericardial anchoring suture is operable to be tensioned so as to cinch the skirt into the deployed configuration.

In accordance with another example ("Example 36"), the pericardial anchoring system of Example 32, wherein the wire frame of the epicardial anchor further comprises a proximal leg, wherein the proximal leg is configured to remain straight and positioned in a center of the epicardial anchor in the deployed configuration.

In accordance with another example ("Example 37"), the pericardial anchoring system of Example 36, wherein the transmyocardial pledget extends from the proximal leg of the epicardial anchor.

In accordance with another example ("Example 38"), the pericardial anchoring system of Example 36, wherein the proximal leg includes two portions of the same wire that is doubled up, such that the two portions are parallel to each other.

In accordance with another example ("Example 39"), the pericardial anchoring system of Example 36, wherein the epicardial anchor is transformable between the predeployed configuration to the deployed configuration at least partially due to proximal retraction of the pericardial anchoring suture.

In accordance with another example ("Example 40"), the pericardial anchoring system of Example 32, wherein the epicardial anchor is transformable between the predeployed configuration to the deployed configuration at least partially due to a shape memory property of the wire frame that is shape-set to the deployed configuration.

In accordance with another example ("Example41"), the pericardial anchoring system of Example 3, wherein a first end of the wire frame and a second end of the wire frame each comprises a nontraumatic end.

In accordance with another example ("Example 42"), the pericardial anchoring system of Example 41, wherein the nontraumatic end of each of the first end of the wire frame and the second end of the wire frame comprises an eyelet.

In accordance with another example ("Example 43"), the pericardial anchoring system of Example 26, wherein the transmyocardial pledget comprises a film with a tubular structure.

In accordance with another example ("Example 44"), the pericardial anchoring system of Example 43, wherein the pericardial anchoring suture is weaved through a plurality of apertures through the film of the transmyocardial pledget.

In accordance with another example ("Example 45"), an epicardial anchor, comprises: a skirt; and a pericardial anchoring suture coupled to the skirt, wherein the epicardial anchor is configured to be transformable between a predeployed configuration and a deployed configuration.

In accordance with another example ("Example 46"), the epicardial anchor of Example 45, wherein the epicardial anchor is configured to form a disc shape in the deployed configuration.

In accordance with another example ("Example 47"), the epicardial anchor of Example 45, wherein the epicardial anchor is configured to form a curved shape, a compressed shape, a bunch, a wad, or a knot in the deployed configuration.

In accordance with another example ("Example 48"), the epicardial anchor of Example 45, wherein the predeployed configuration comprises an elongate configuration, and wherein the deployed configuration comprises a compressed configuration.

In accordance with another example ("Example 49"), the epicardial anchor of Example 45, wherein the predeployed configuration comprises an elongate configuration, and wherein the deployed configuration comprises a coiled configuration.

In accordance with another example ("Example 50"), the epicardial anchor of Example 45, wherein the epicardial anchor has a free end in the predeployed configuration, wherein the epicardial anchor is configured to coil beginning from the free end of the epicardial anchor to form the deployed configuration.

In accordance with another example ("Example 51"), the epicardial anchor of Example 45, wherein the epicardial anchor further comprises a wire frame, wherein the wire frame is covered with the skirt.

In accordance with another example ("Example 52"), the epicardial anchor of Example 45, wherein the wire frame of the epicardial anchor has a shape memory property that is shape-set to the deployed configuration.

In accordance with another example ("Example 53"), the epicardial anchor of Example 51, wherein the skirt is configured to slidingly receive the pericardial anchoring suture, and wherein the pericardial anchoring suture is operable to be tensioned so as to cinch the skirt into the deployed configuration.

In accordance with another example ("Example 54"), the epicardial anchor of Example 51, wherein the skirt of the epicardial anchor is coupled to the wire frame along an edge defining a length, wherein the skirt comprises a plurality of apertures along an edge of the skirt opposite the wire frame, wherein the pericardial anchoring suture is alternately weaved through the plurality of apertures, and wherein the pericardial anchoring suture is operable to be tensioned so as to cinch the skirt into the deployed configuration.

In accordance with another example ("Example 55"), the epicardial anchor of Example 51, wherein the wire frame of the epicardial anchor further comprises a proximal leg, wherein the proximal leg is configured to remain straight and positioned in a center of the epicardial anchor in the deployed configuration.

In accordance with another example ("Example 56"), the epicardial anchor of Example 55, wherein the proximal leg includes two portions of the same wire that is doubled up, such that the two portions are parallel to each other.

In accordance with another example ("Example 57"), the epicardial anchor of Example 55, wherein the epicardial anchor is transformable between the predeployed configuration to the deployed configuration at least partially due to proximal retraction of the pericardial anchoring suture.

In accordance with another example ("Example 58"), the epicardial anchor of Example 51, wherein the epicardial anchor is transformable between the predeployed configuration to the deployed configuration at least partially due to a shape memory property of the wire frame that is shape-set to the deployed configuration.

In accordance with another example ("Example 59"), the epicardial anchor of Example 51, wherein a first end of the wire frame and a second end of the wire frame each comprises a nontraumatic end.

In accordance with another example ("Example 60"), the epicardial anchor of Example 64, wherein the nontraumatic end of each of the first end of the wire frame and the second end of the wire frame comprises an eyelet.

In accordance with another example ("Example 61"), a method of anchoring a pericardial anchor system, comprises: advancing an epicardial anchor in a predeployed configuration constrained within an anchor catheter into a pericardial space of a heart; advancing the anchor catheter tangentially in the pericardial space a predetermined distance to allow for unsheathing of the epicardial anchor in the predeployed configuration; and retracting the anchor catheter to at least partially deploy the epicardial anchor in a deployed configuration in the pericardial space.

In accordance with another example ("Example 62"), the method of anchoring a pericardial anchor system of Example 61, wherein the predetermined distance comprises at least 10 cm.

In accordance with another example ("Example 63"), the method of anchoring a pericardial anchor system of Example 61, wherein the anchor catheter is configured to travel in a medial-lateral direction and/or in an inferior-superior direction in the pericardial space.

In accordance with another example ("Example 64"), the method of anchoring a pericardial anchor system of Example 61, further comprising positioning a proximal leg of the epicardial anchor between an epicardium and a distal tip of the anchor catheter to maintain a position of the epicardial anchor within the pericardial space.

In accordance with another example ("Example 65"), the method of anchoring a pericardial anchor system of Example 61, further comprising applying tension to a pericardial anchoring suture of the pericardial anchor system to at least partially transform the epicardial anchor to the deployed configuration.

In accordance with another example ("Example 66"), the method of anchoring a pericardial anchor system of Example 61, wherein the epicardial anchor is further transformed to the deployed configuration at least partially due to a shape memory property of a wire frame of the epicardial anchor that is shape-set to the deployed configuration.

In accordance with another example ("Example 67"), a method of anchoring a pericardial anchor system, comprises: advancing a support sheath up to and against a heart wall in a heart chamber; advancing a guidewire through the support sheath such that a guidewire distal tip advances through an endocardium, a myocardium, and an epicardium, and into a pericardial space; advancing an anchor sheath and a guidewire sheath together through the support sheath and over the guidewire and into the pericardial space to form a puncture through the endocardium, the myocardium, and the epicardium; maintaining a position of the guidewire sheath while retracting the anchor sheath and the support sheath together to deploy an epicardial anchor of a pericardial anchoring system in the pericardial space, wherein the epicardial anchor is in a predeployed configuration while positioned within the anchor sheath; maintaining a position of the anchor sheath while retracting the guidewire sheath to form a t-bar between a proximal leg of a wire frame of the epicardial anchor and a distal tip of the anchor sheath; retracting the support sheath, the anchor sheath, and the guidewire sheath together until the proximal leg is positioned against the puncture of the epicardium; maintain a position of the guidewire sheath and retract the anchor sheath and the support sheath together to deploy the epicardial anchor; and apply tension to a pericardial anchoring suture of the pericardial anchor system to at least partially transform the epicardial anchor to a deployed configuration.

In accordance with another example ("Example 68"), the method of anchoring a pericardial anchor system of Example 67, wherein the epicardial anchor is further transformed to the deployed configuration at least partially due to a shape memory property of the wire frame that is shape-set to the deployed configuration.

In accordance with another example ("Example 69"), the method of anchoring a pericardial anchor system of Example 67, further comprising maintaining a position of the guidewire sheath and retracting the support sheath and the anchor sheath to deploy a transmyocardial pledget and an anchor socket of the pericardial anchoring system, wherein a first portion of the transmyocardial pledget is positioned within the puncture of the epicardium, the myocardium, and the endocardium and a second portion of the transmyocardial pledget extends proximally from the puncture of the endocardium.

In accordance with another example ("Example 70"), the method of anchoring a pericardial anchor system of Example 67, further comprising folding the second portion of the transmyocardial pledget against the puncture of the endocardium.

In accordance with another example ("Example 71"), the method of anchoring a pericardial anchor system of Example 67, further comprising advancing a suture lock into the anchor socket and advancing the suture lock positioned within the anchor socket towards the endocardium to fold the second portion of the transmyocardial pledget.

In accordance with another example ("Example 72"), the method of anchoring a pericardial anchor system of Example 68, wherein the proximal leg of the epicardial anchor covered with a film is configured to seal the puncture of the epicardium, wherein the first portion of the transmyocardial pledget is configured to seal the puncture of the myocardium, and wherein the folded second portion of the transmyocardial pledget is configured to seal the puncture of the endocardium. In accordance with an embodiment, a pericardial access and fixation tool, referred herein as a tool, is provided operable for deployment into the myocardium and extending into the pericardial space from the ventricular side of the heart.

In accordance with another example ("Example 73"), a tool for placement in a heart wall and pericardial space operable to provide access to the pericardial space from a chamber of a heart and/or operable to be an anchor for devices coupled thereto, comprises a body defining a lumen operable to extend through the heart wall, a head at a distal end of the body operable to extend into the pericardial space, the head including movable elements operable to move from a low profile predeployed configuration to a high profile deployed configuration, the head defining an eyelet that is in fluid communication with the lumen so as to define and access channel operable to provide a fluid passage between the chamber of the heart and the pericardial space, and the base further comprises a retention member operable to retain the base in the heart wall.

In accordance with another example ("Example 74"), the tool of Example 73, wherein the movable elements are operable to buttress a parietal pericardium when the movable members attain a high profile in the deployed configuration and wherein the retention member cooperates to engage the movable elements into abutment with the parietal pericardium.

In accordance with another example ("Example 75"), the tool of Examples 73 and 74, the tool of examples 1 and 2, wherein the movable elements include expander members operable to abut the pericardium so as to enlarge a pericardial space.

In accordance with another example ("Example 76"), the tool of Examples 73 and 74, wherein the eyelet is operable to expel or withdraw fluid or gas from a pericardial space using a device in communication with the lumen.

In accordance with another example ("Example 77"), the tool of Example 73, wherein the eyelet is operable to be a pressure port operable to measure pressure with a pressure sensing device.

In accordance with another example ("Example 78"), the tool of any of Examples 73-77, wherein the access channel is operable for receiving and allowing the passage of devices therethrough between a ventricular side of the heart to the pericardial space.

In accordance with another example ("Example 79"), the tool of any of Examples 73-77, wherein the eyelet is operable to resiliently deform between open and closed configurations, wherein in the closed configuration the access channel is occluded to prevent fluid passage through the access channel.

In accordance with another example ("Example 80"), the tool of any of Examples 73-77, wherein the head further includes an occluding element operable to resiliently move between open and closed positions, wherein in the closed position the access channel is occluded to prevent fluid passage through the access channel.

In accordance with another example ("Example 81"), the tool of any of Examples 73-77, further comprises an occluding plug operable to be placed in the access channel so as to occlude the access channel to prevent fluid passage through the access channel.

In accordance with another example ("Example 82"), the tool of any of Examples 73-77, wherein the tool is operable to couple with other devices or tissues of the heart.

In accordance with another example ("Example 83"), a method of implanting the tool of any one of examples 69-82, includes providing a delivery system operable for endovascular epicardial access, the delivery system including a steerable catheter and a delivery catheter, inserting the delivery system into the patient using a transvenous, transarterial, transseptal, transatrial, or transaortic approach, advancing the delivery catheter, onto which the tool is coupled, into the myocardium and extending the head of the tool into the pericardial space.

In accordance with another example ("Example 84"), the method of implanting the tool of Example 83, wherein the delivery system further includes a guidewire and/or needle, the method including advancing the guidewire or needle through the delivery catheter and extending through the tool into the myocardium and into the pericardial space and advancing the tool over the guidewire or needle.

The foregoing Examples are just that and should not be read to limit or otherwise narrow the scope of any of the inventive concepts otherwise provided by the instant disclosure.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 15 is a flow diagram of an embodiment of a method of providing a pericardial anchoring system;

FIG. 16 is a flow diagram of an embodiment of a method of providing a pericardial anchoring system;

FIG. 17 is a flow diagram of an embodiment of a method of providing a pericardial anchoring system;

FIGS. 54A and 54B are side and cross-sectional views, respectively, of the tool, in accordance with an embodiment.

FIG. 54C is a cross-sectional view of the left ventricle and mitral valve leaflets, illustrating the steerable guide catheter for placement of the tool.

FIG. 54D is a cross-sectional view of the left ventricle illustrating the steerable guide catheter distal end.

FIG. 55A is a cross-sectional view of the heart illustrating the delivery system located adjacent to the endocardium, in accordance with an embodiment.

FIG. 55B is a cross-sectional view of the heart illustrating the tool traversing the endocardium and myocardium with the assistance of a needle for placement in the myocardium and pericardial space during a deployment process, in accordance with an embodiment.

FIG. 55C is a cross-sectional view of the heart illustrating the tool traversing the epicardium for placement in the myocardium and pericardial space during a deployment process, in accordance with an embodiment.

FIG. 55D is a cross-sectional view of the heart illustrating the tool enlarging the pericardial space during a deployment process, in accordance with an embodiment.

FIG. 55E is a cross-sectional view of the heart illustrating the movable elements of the tool enlarging the pericardial space during a deployment process, in accordance with an embodiment.

FIG. 55F is a cross-sectional view of the heart illustrating the movable elements of the tool engaging the epicardium and/or the pericardium so as to anchor the tool in the pericardial space, in accordance with an embodiment.

FIG. 55G is a cross-sectional view of the heart illustrating the movable elements of the tool engaging the epicardium and/or the pericardium so as to anchor the tool in the pericardial space, in accordance with an embodiment.

FIG. 55H is a top view of the head illustrating the placement of the movable elements in the deployed configuration, in accordance with an embodiment.

FIG. 55I is a cross-sectional view of the heart illustrating the tool in the deployed configuration placement in the myocardium and pericardial space, in accordance with an embodiment.

FIGS. 56A1 and 56A2 are top and side views, respectively, of a tool head with movable elements, in accordance with an embodiment.

FIG. 56A3 is a side view of a tool head with movable elements, in accordance with an embodiment.

FIG. 56A4 is a side view of a tool head with movable elements, in accordance with an embodiment.

FIG. 56B1 is a top view of a tool head with movable elements, in accordance with an embodiment.

FIG. 56B2 is a top view of a tool head with movable elements, in accordance with an embodiment.

FIG. 56B3 is a top view of a tool head with movable elements, in accordance with an embodiment.

FIG. 56B4 is a top view of a tool head with movable elements, in accordance with an embodiment.

FIG. 56C1 is a top view of a tool head with movable elements, in accordance with an embodiment.

FIG. 56C2 is a top view of a tool head with movable elements, in accordance with an embodiment.

FIG. 56C3 is a top view of a tool head with movable elements, in accordance with an embodiment.

FIG. 56C4 is a top view of a tool head with movable elements, in accordance with an embodiment.

FIG. 56D1 is a side view of a tool head with movable elements, in accordance with an embodiment.

FIG. 56D2 is a side view of a tool head with movable elements, in accordance with an embodiment.

DETAILED DESCRIPTION

Figure 1A:
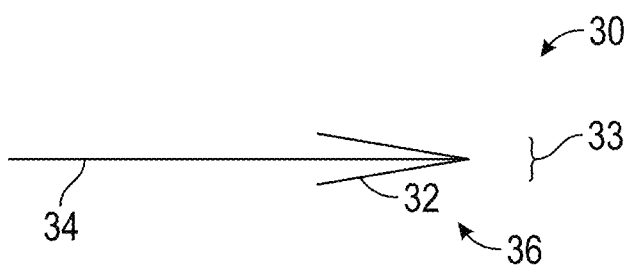
FIG. 1A is a side view of an anchor system, in accordance with an embodiment.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with mitral valve leaflet prolapse prevention by way of an anchoring system that is contained within the pericardial space. However, embodiments within the scope of this disclosure can be applied toward any prosthesis or mechanism of similar structure and/or function that requires anchoring within the chambers of the heart.

Embodiments herein include various apparatuses, systems, and methods for a suture or other tether mechanism having an anchor that lies within the pericardial space, with the suture extending through the myocardium and endocardium for use to couple with a biological element, such as a mitral valve leaflet, or to a prosthesis, such as, but not limited to, a sensor or support structure. The anchor that lies within and adjacent to the epicardium (visceral layer of serous pericardium) may be of any suitable structure, such as, but not limited to, an umbrella-like element, a pledget, a multi-legged support structure, and the like. The anchor is operable to have a low profile so as to be able to pass through a narrow access channel in the heart wall and expand or deploy to a larger diameter or surface area within the pericardial space and not pass through the narrow access channel in the heart structure. The present disclosure relates to mitral valve repair or replacement and more generally to methods and devices for mitral valve reshaping, repair and/or replacement of mitral chords, also referred to as chordae tendineae, to restore proper functioning of the mitral valve from a state of malfunction, such as, but not limited mitral valve regurgitation.

The term "heart wall", as used herein, is defined as the endocardium, myocardium and epicardium.

The terms "pericardial space" and "pericardial cavity", as used herein, is that space defined by the heart wall and the pericardium, therebetween, or the space between the visceral pericardium and the parietal pericardium.

The term "coupled", as used herein, means joined, connected, attached, adhered, affixed, or bonded, whether directly or indirectly, and whether permanently or temporarily.

In accordance with embodiments, and as provided in FIG. 17, pericardial anchoring is provided by way of a small hollow needle catheter (e.g., 20-25 gauge) and a compatible guidewire (e.g., 0.010"-0.018", operable to fit through the lumen of the needle catheter). Heart wall crossing from within a heart chamber is initiated by the needle catheter passing through the endocardium and into the myocardium, and completed by a guidewire passing through the remainder of the myocardium and through the epicardium. The guidewire is placed into the pericardial space so that an anchor of an anchor system can subsequently be delivered over the guidewire and into the pericardial space.

Due to extremely small profile the risk of adverse events may be lowered, such as, unlikely to cause pericardial effusion/tamponade.

Crossing the epicardium with a guidewire instead of a needle catheter results in an increase in safety and also procedural ease-of-use by, for example, taking out guesswork/ambiguity of getting into the pericardial space for being not too short or too far, since imaging of this space and/or knowing placement in the pericardial space is challenging. The selection of guidewire stiffness, for example, is optimized, both at distal tip and along entire length, such that, but not limited to, the distal tip being stiff enough that it may cross the remainder of the heart wall and into the pericardial space, but soft enough so as to deflect and not puncture the pericardium (parietal layer of serous pericardium and fibrous pericardium). The guidewire is operable to coil up within the pericardial space and track within the pericardial space. Advancement of the guidewire distal end within the pericardial space and adjacent to the heart wall may provide the clinician evidence that the distal end of the guidewire is in the pericardial space.

Wherein the guidewire outer diameter is just slightly less than needle inner diameter, potential coring out of the heart wall is mitigated or minimize so as to reduce tissue trauma. The needle catheter and guidewire may be introduced together with the guidewire distal tip just slightly pulled back relative to needle catheter distal tip, i.e., nested or in tandem. Subsequent to the needle catheter puncturing the endocardium, the guidewire may be advanced beyond needle catheter distal tip with the needle catheter providing support for the guidewire.

It is appreciated that there are different ways to advance the small hollow needle catheter and subsequently the nested guidewire to a target location. In one embodiment, the needle catheter may be advanced over a previously placed guidewire, in an over-the-wire procedure, such as, but not limited to, from an access port in the femoral vein. In other embodiments, the needle catheter with or without a nested guidewire, may be advanced through a lumen of a previously-placed steerable or non-steerable sheath, support/ guide catheters, and the like.

It is appreciated that subsequent to the guidewire crossing into the pericardial space, there may be some additional steps required to be performed prior to advancement of the anchoring system. By way of example, but not limited thereto, utilization of contrast agents, CO2, microcatheters, various guidewires, support/guide catheters, and other devices, agents, and therapeutics may be used for a particular purpose. Such devices, agents and therapeutics may be provided so as, but not limited to, creating physical space in the pericardial space at the target location, visualizing the pericardial space and/or heart/pericardium structures at the target location, ensuring adequate purchase of a suitability stiff and correct diameter guidewire in the pericardium to deliver the anchoring system.

In accordance with embodiments, diagnostic modalities may be employed so as to provide evidence of guidewire crossing the heart wall and into the pericardial space. By way of example, such diagnostic modalities may include, but not limited thereto, a guidewire attached to an ECG lead (such as a guidewire having a non-electrically conductive coating except for a proximal and distal tip), and a pressure-sensing guidewire with a sensing element at the distal tip. Data gathered from these modalities may provide evidence of guidewire crossing the heart wall and into the pericardial space.

Figure 1B:
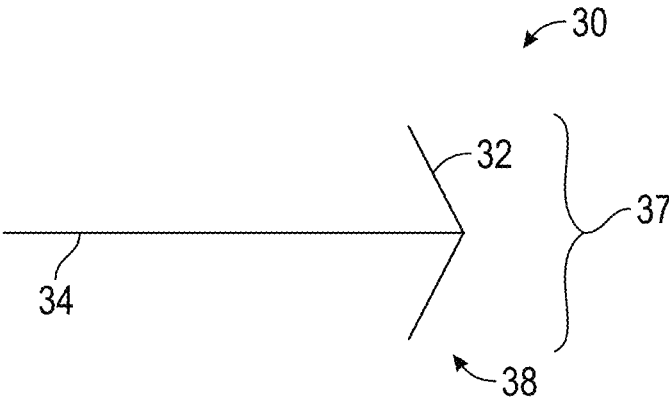
FIG. 1B is a side view of the anchor system of FIG. 1A.

FIGS. 1A and 1B are side views of an anchoring system 30, that includes an anchor 32 and a tether 34 coupled to the anchor 32. The anchor 32 is operable to have a low profile 33 in a first position 36 and a larger profile 37 in a second position 38. The anchor 32 is operable to be advanced into a pericardial space 10 from a heart chamber 6 of a heart 2 through a narrow access channel 12 in a heart wall 41 in the first position 36 and expand to the second position 38 in the pericardial space 10 to a size greater than the narrow access channel 12.

Figure 2B:
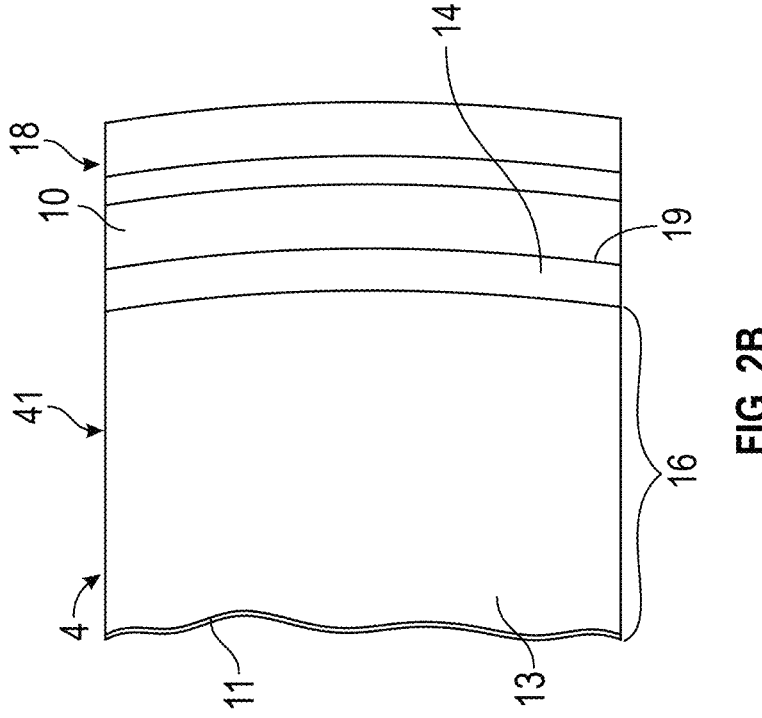
FIG. 2B is a close-up cross-sectional view of the heart of FIG. 2A.
Figure 2A:
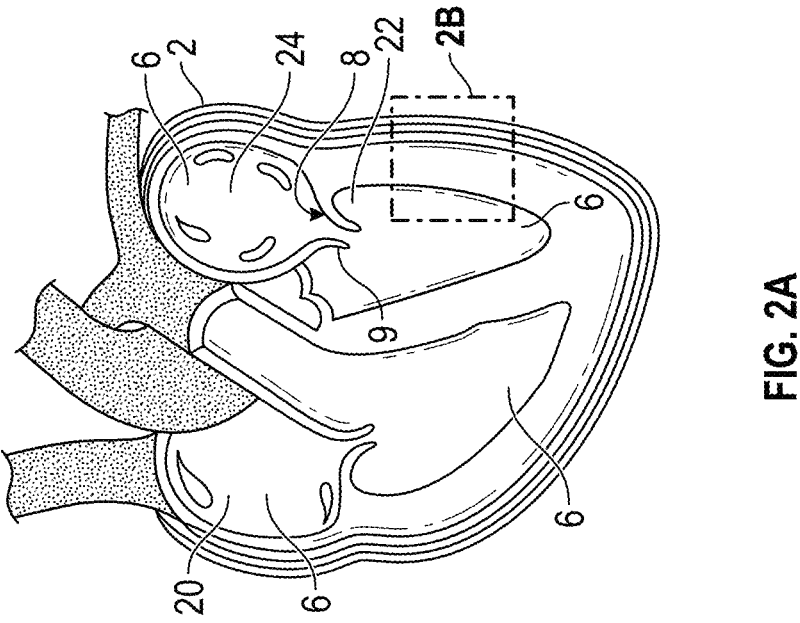
FIG. 2A is a cross-sectional view of a heart.
Figure 3:
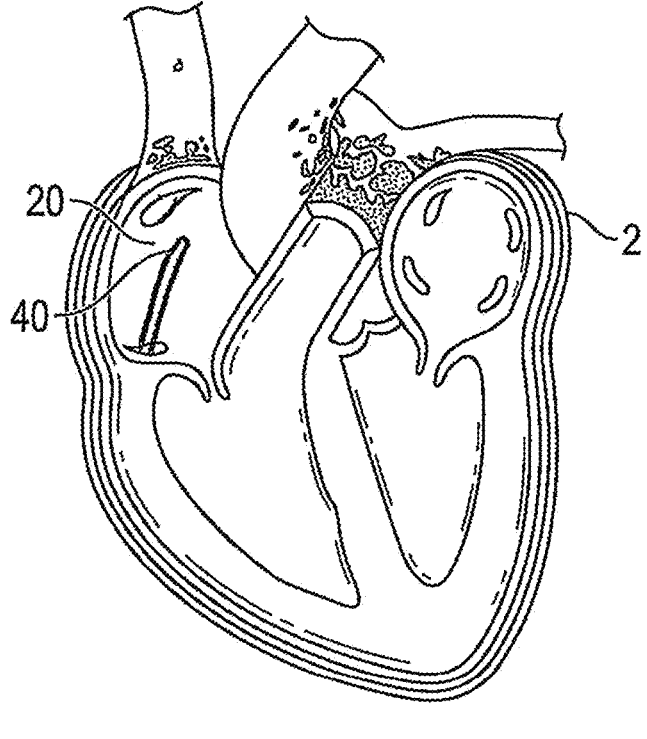
FIG. 3 is a cross-sectional view of a heart with a guidewire in accordance with an embodiment of the method of providing a pericardial anchoring system.
Figure 4:
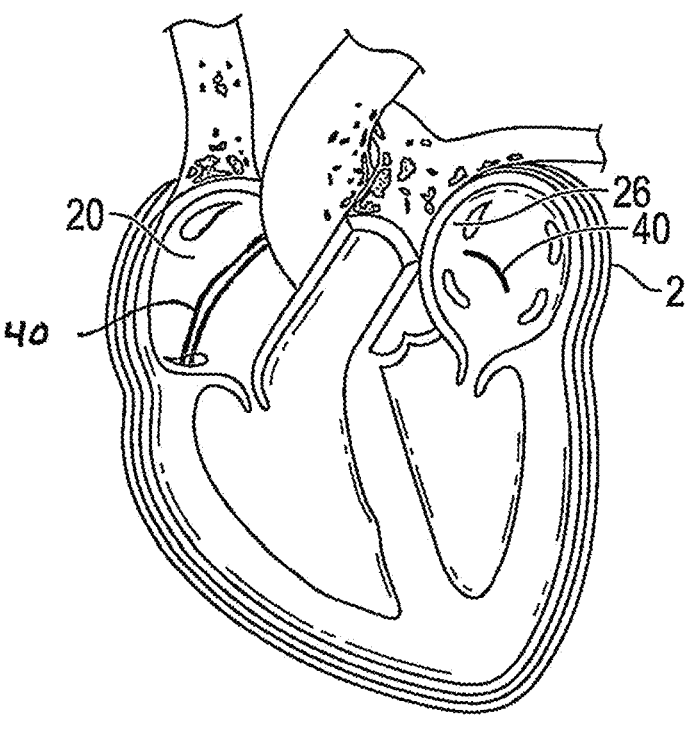
FIG. 4 is a cross-sectional view of a heart with a guidewire in accordance with an embodiment of the method of providing a pericardial anchoring system.
Figure 5B:
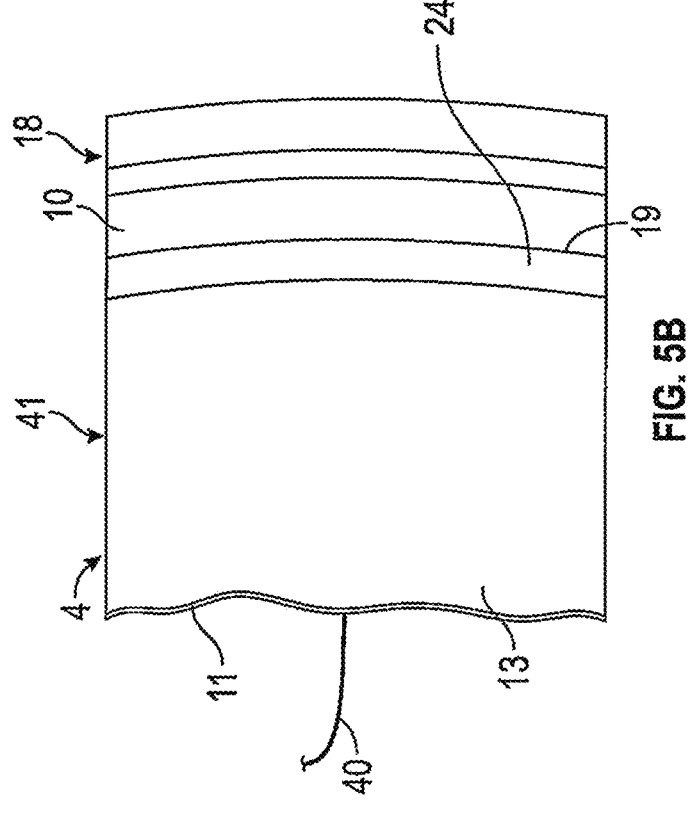
FIG. 5B is a cross-sectional view of a heart with a guidewire in accordance with an embodiment of the method of providing a pericardial anchoring system.
Figure 5A:
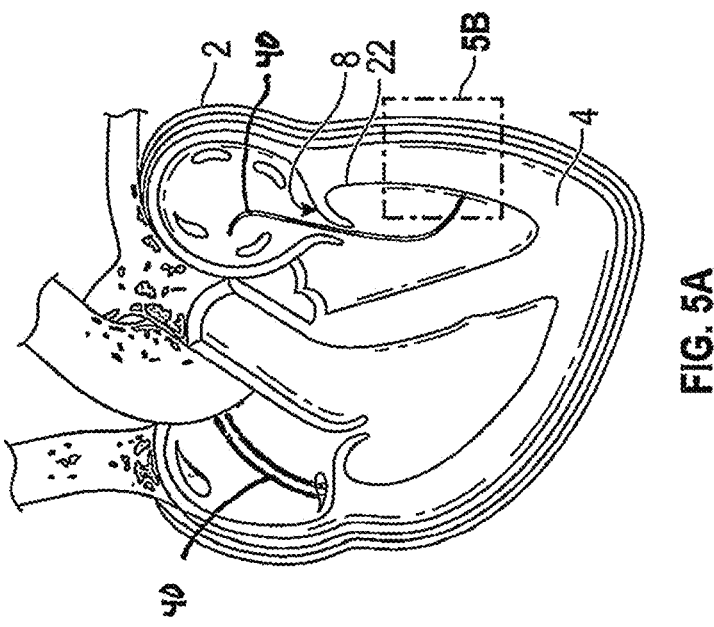
FIG. 5A is a cross-sectional view of a heart with a guidewire in accordance with an embodiment of the method of providing a pericardial anchoring system.
Figure 6:
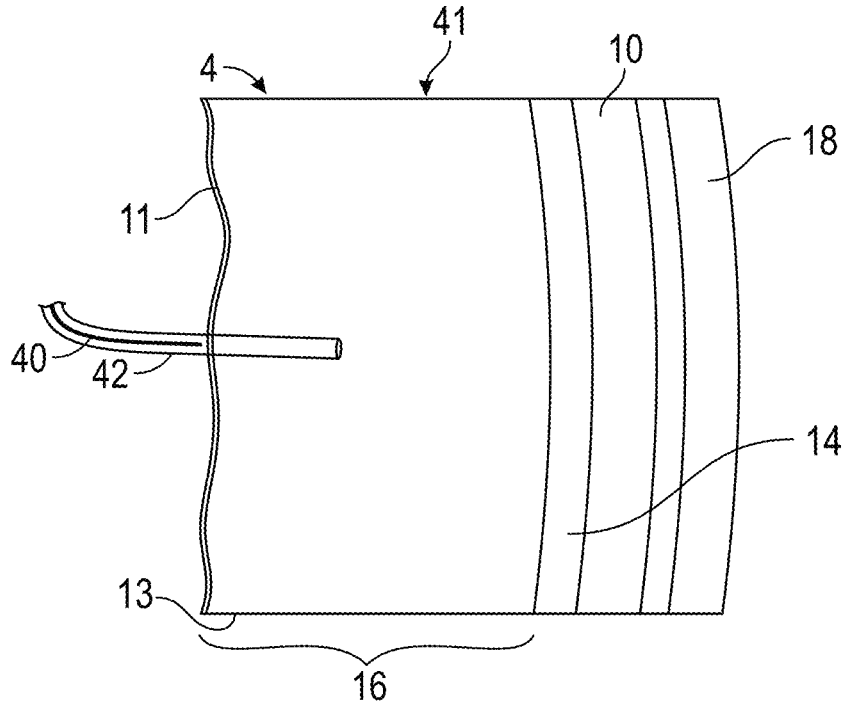
FIG. 6 is a cross-sectional view of a heart with a guidewire and needle catheter in accordance with an embodiment of the method of providing a pericardial anchoring system.
Figure 7:
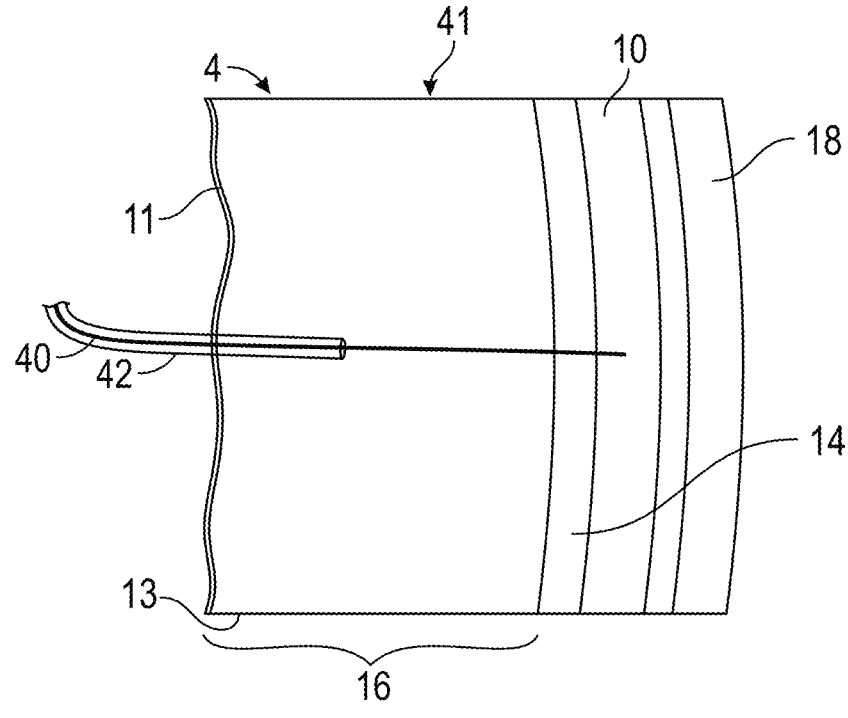
FIG. 7 is a cross-sectional view of a heart with a guidewire and needle catheter in accordance with an embodiment of the method of providing a pericardial anchoring system.
Figure 8:
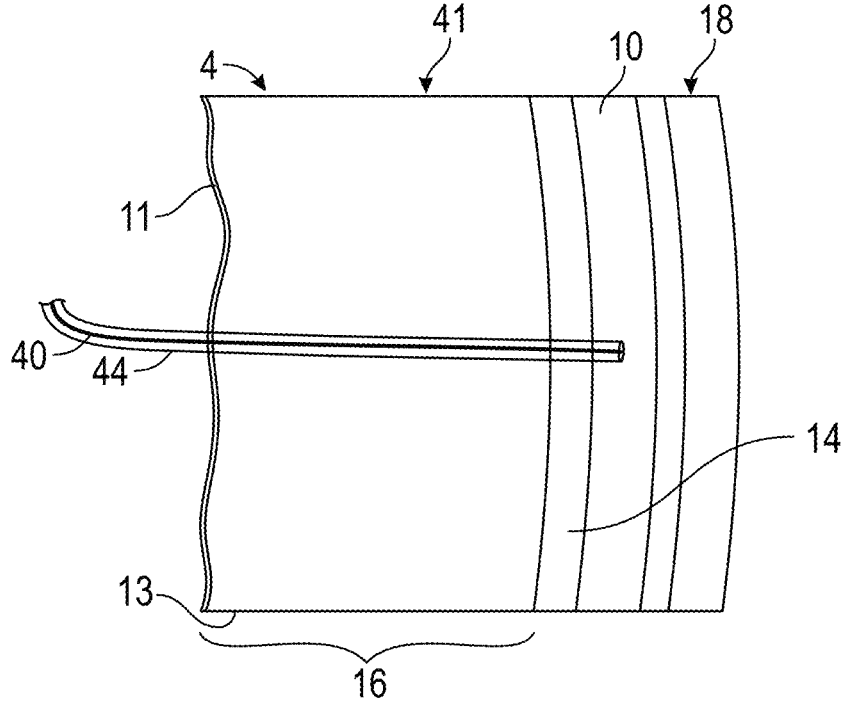
FIG. 8 is a cross-sectional view of a heart with a guidewire and catheter in accordance with an embodiment of the method of providing a pericardial anchoring system.
Figure 9:
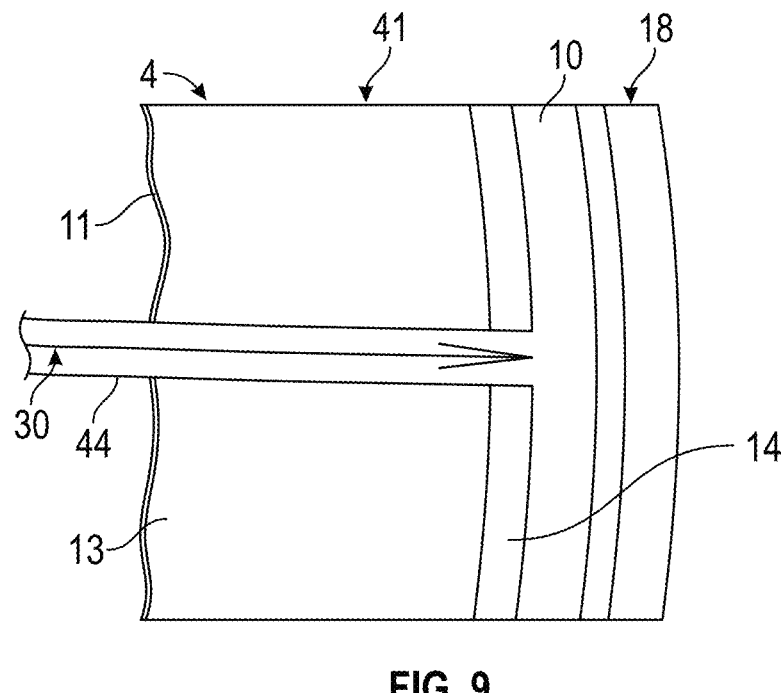
FIG. 9 is a cross-sectional view of a heart with a catheter and an anchoring system in accordance with an embodiment of the method of providing a pericardial anchoring system.
Figure 10:
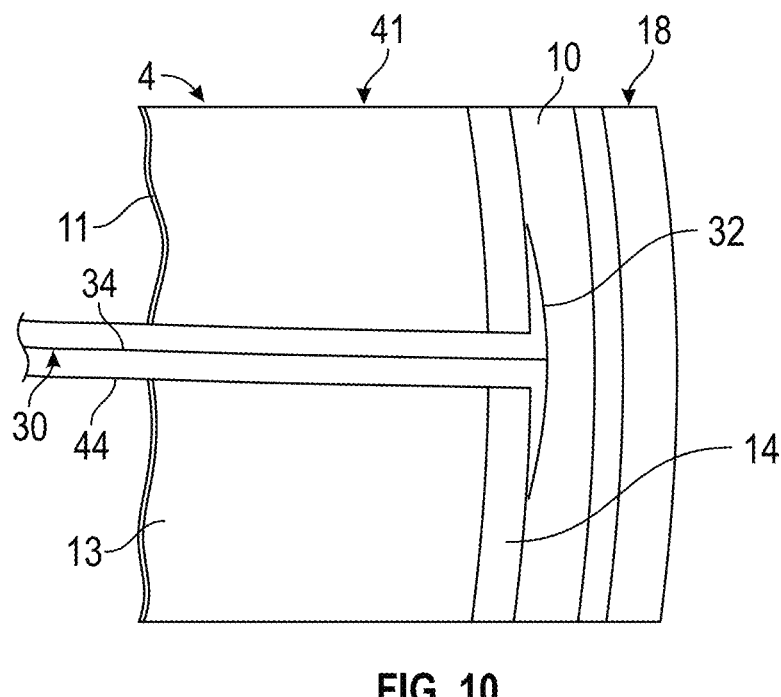
FIG. 10 is a cross-sectional view of a heart with a catheter and an anchoring system that has been deployed in accordance with an embodiment of the method of providing a pericardial anchoring system.
Figure 11:
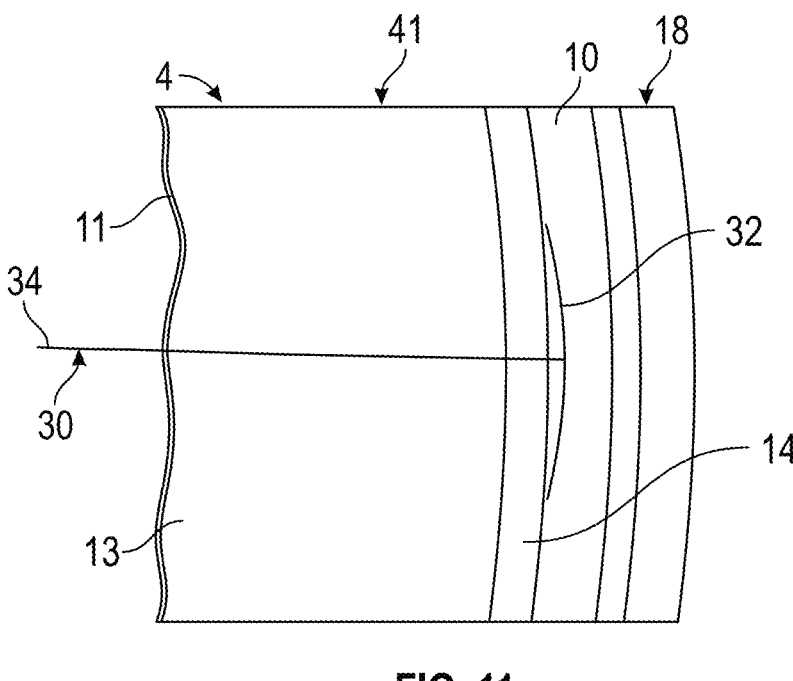
FIG. 11 is a cross-sectional view of a heart with an anchoring system that has been deployed in accordance with an embodiment of the method of providing a pericardial anchoring system.
Figure 12:
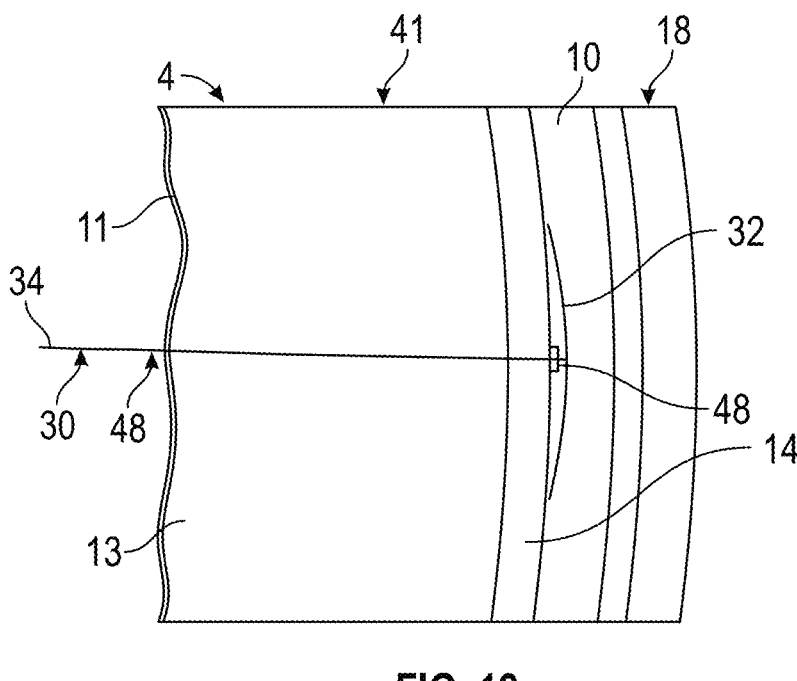
FIG. 12 is a cross-sectional view of a heart with an anchoring system that has been deployed with a sealing means, in accordance with an embodiment of the method of providing a pericardial anchoring system.

FIGS. 2A and 2B are cross-sectional views of the heart 2 and its corresponding anatomical features.

FIGS. 3-14 are a series of illustrations, and FIG. 15 a flow diagram, of a method of providing an anchor 32 in a heart chamber 6, in accordance with an embodiment. A femoral vein is accessed and a guidewire 40 is advance therein. The guidewire 40 is advanced through the femoral vein, and into the right atrium 20, FIG. 3. The guidewire 40 is advanced through the septum 26 and into the left atrium 24, FIG. 4. The guidewire 40 is advanced through the mitral valve 8 and advanced up to and adjacent the heart wall 41 of the left ventricle 22, FIGS. 5A and 5B. A needle catheter 42 is advanced over the guidewire 40 and into about half of the thickness 16 of the myocardium 13, FIG. 6. The guidewire 40 having a stiff distal tip is advanced through the needle catheter 42 through the epicardium 14 and into the pericardial space 10, FIG. 7. A catheter 44 is advanced over the guidewire 40 and into the pericardial space 10, FIG. 8. A gas, such as carbon dioxide, is used to inflate and separate the pericardium 18 from the heart wall 41, enlarging the pericardial space 10. An anchoring system 30 can be advanced over the guidewire 40 after removing the catheter 44, and/or it can be advanced through the catheter 44 after removing the guidewire 40, FIG. 9. The anchoring system 30 may be facilitated by an anchoring system delivery catheter operable to deliver and deploy the anchoring system. An anchor is deployed within the pericardial space 10 and placed so as to oppose the epicardium 14, FIG. 10. The anchoring system 30 includes a suture or tether 34 that is coupled to the anchor 32 with the suture or tether 34 remaining in the heart chamber 6, FIG. 11.

It is anticipated that once the delivery system, that is, any guidewire 40 and/or catheter 44 is removed from the heart 2, the heart wall 41 will seal around the suture or tether 34 such that no additional material is needed to prevent bleeding from the access channel 12. It is anticipated that optionally, a sealing means 48 may be provided to reduce or eliminate potential bleeding. Such sealing means 48 may include, but not limited to, a surface texture on the tether 34 so as to induce a healing response between the tether 34 and the heart wall 41, a pledget along the tether 34 that may be used to plug the access channel 12, an expandable portion or element about the tether 34 and/or the anchor 32 that is operable to close the access channel 12 about the tether 34 and/or anchor, FIG. 12.

Figure 13:
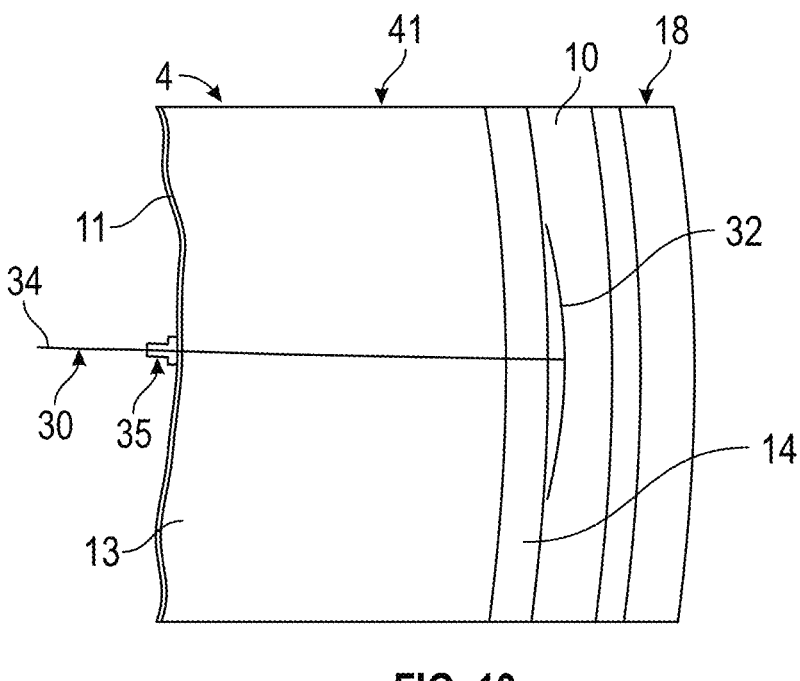
FIG. 13 is a cross-sectional view of a heart with an anchoring system that has been deployed with a tether lock, in accordance with an embodiment of the method of providing a pericardial anchoring system.
Figure 14:
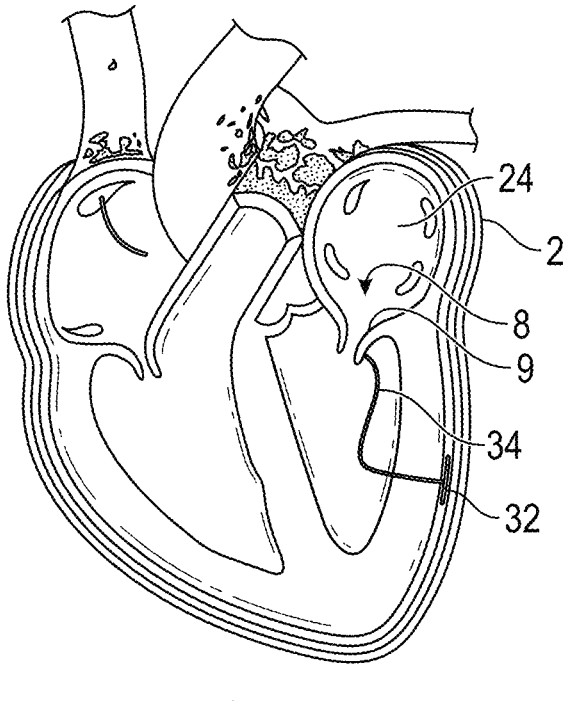
FIG. 14 is a cross-sectional view of a heart with an anchoring system that has been deployed and coupled to a mitral valve leaflet to prevent prolapse, in accordance with an embodiment of the method of providing a pericardial anchoring system.

In another embodiment, illustrated in FIG. 13, a tether lock 35 is advanced over the tether 34 and in abutment with the endocardium 11 operable to engage the tether 34 and hold fast so as to capture the heart wall 41 between the tether lock 35 and the anchor. Such a tether lock 35 may be operable to ensure urging engagement of the anchor 32 with the endocardium 11 so as to prevent movement thereof, so as to, for example, prevent any subsequent irritation to the pericardium 18.

As provided before, the suture or tether 34 may be used for a particular purpose. In accordance with an embodiment, the suture or tether 34 is coupled to a mitral valve leaflet 9 so as to prevent the leaflet from prolapsing, illustrated in FIG. 14.

In accordance with another embodiment, the suture or tether 34 may be coupled to a device, such as a prosthetic valve.

In accordance with another embodiment, the suture or tether 34 may be coupled to a device, such as a sensor.

In accordance with another embodiment, as provided in the flow diagram of FIG. 16, and referring to FIGS. 1-14 for reference, a method of anchoring includes advancing a guidewire 40 into a heart 2 up to and adjacent a heart wall 41. A needle catheter 42 is advanced over the guidewire 40 and into about half of a thickness 16 of the heart wall 41. The guidewire 40 is advanced through the needle catheter 42 through an epicardium 14 and into a pericardial space 10. The needle catheter 42 is withdrawn from the guidewire 40. A catheter 44 is advanced over the guidewire 40 and into the pericardial space 10. The pericardium 18 is separated from the heart wall 41 so as to enlarge the pericardial space 10. An anchoring system 30 is advanced either over the guidewire 40 or through the catheter 44, an anchor portion 39 of which placed into the pericardial space 10. An anchor 32 of the anchoring system 30 is deployed within the pericardial space 10 and placed so as to oppose the epicardium 14. The guidewire 40 and/or catheter 44 is removed from a patient leaving a tether 34 that is coupled to the anchor 32 in a heart chamber 6.

In accordance with another embodiment, a method of anchoring includes optionally advancing a support catheter into a heart near or up to and adjacent to or against a heart wall. An anchoring catheter is advanced singularly or through the optional support catheter and placed near or in urging engagement against the heart wall. A guidewire is advanced through the anchor catheter through an endocardium through a myocardium and through an epicardium (visceral layer of serous pericardium) of the heart wall and into a pericardial space. The anchor catheter is advanced over the guidewire and through the endocardium through the myocardium and through the epicardium (visceral layer of serous pericardium) of the heart wall and into the pericardial space. Optionally, the guidewire is withdrawn from the pericardial space. Optionally the pericardium is separated from the epicardium so as to enlarge the pericardial space. An anchor of an anchoring system is advanced or exposed through or at or near a distal end of the anchor catheter which is in the pericardial space, wherein the anchor is placed into the pericardial space. The anchor of the anchoring system is deployed within the pericardial space and the anchor is placed so as to oppose the epicardium. The guidewire and/or anchor catheter and/or support catheter are removed from a patient leaving a tether that is coupled to the anchor in a heart chamber.

In accordance with another embodiment of a method of anchoring includes advancing an anchor catheter near or up to and against a heart wall in a heart chamber. A guidewire is advanced through the anchoring catheter such that a guidewire distal tip advances through an endocardium and into a myocardium through the epicardium and into a pericardial space. A distal tip of the anchor catheter is advanced along or over the guidewire and into or adjacent to the pericardial space. An anchor of an anchoring system is advanced or exposed through or at a distal end of the anchor catheter which is in the pericardial space, wherein the anchor is placed in the pericardial space. The anchor of the anchoring system is deployed within the pericardial space and the anchor is placed so as to oppose the epicardium. The guidewire and/or anchor catheter are removed from a patient leaving a tether that is coupled to the anchor in a heart chamber of an anchoring system over the guidewire and into the pericardial space.

Figure 18:
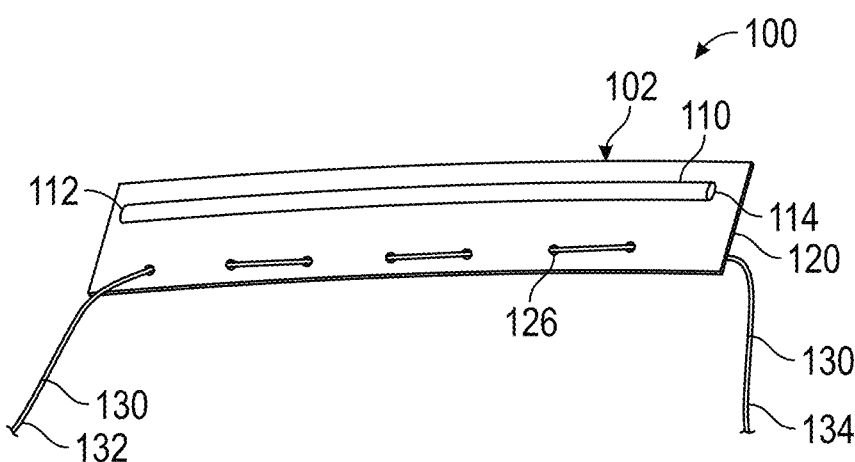
FIG. 18 is a plan view of the anchor system in a pre-deployment configuration wherein the wire and the skirt are in a straight configuration, in accordance with an embodiment.
Figure 19:
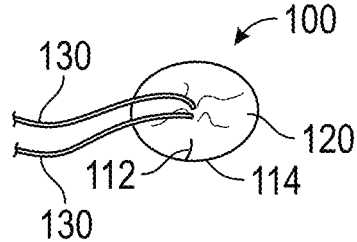
FIG. 19 is a plan view of the anchor system in the deployed configuration wherein the wire and the skirt are in a ring configuration, in accordance with the embodiment of FIG. 18.
Figure 20:
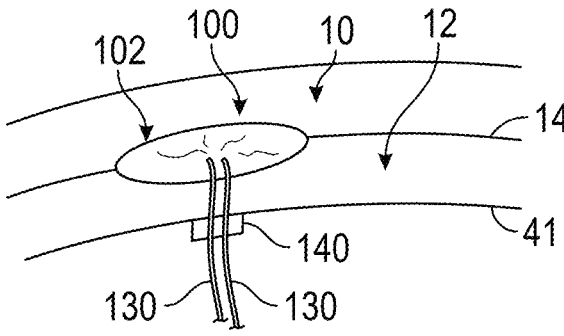
FIG. 20 is a perspective cross-sectional view of the anchor system deployed in the pericardial space with the anchor placed against the epicardium, with the tethers passing through the endocardium and further including an optional tether lock on the opposite side of the endocardium, in accordance with the embodiment of FIGS. 18 and 19.

In accordance with an embodiment, an anchor system 100 includes an anchor 102. FIG. 18 is a plan view of the anchor system 100 in a pre-deployment configuration wherein the wire 110 and the skirt 120 are in a straight configuration. FIG. 19 is a plan view of the anchor system 100 in the deployed configuration wherein the wire 110 and the skirt 120 are in a ring configuration. FIG. 20 is a perspective cross-sectional view of the anchor system 100 deployed in the pericardial space 10 with the anchor 102 placed against the epicardium 14, with the tethers 130 passing through the endocardium 11 and further including an optional tether lock 140 on the opposite side of the endocardium 11.

The anchor 102 includes a wire 110 having a wire first end 112 and a wire second end 114. The wire 110 has a shape memory property that is shape-set to a ring configuration wherein the wire first end 112 opposes the wire second end 114. A skirt 120 is coupled to the wire 110 along an edge defining a length. A plurality of apertures 126 are along an edge of the skirt 120 opposite the wire 110. The tether 130 is alternately weaved through the plurality of apertures 126, wherein the tether 130 defines a tether first end 132 and a tether second end 134. The tether first end 132 and the tether second end 134 are operable to be tensioned so as to cinch the skirt 120 into a disc-like shape when the wire 110 is in the ring configuration in a deployed configuration, and wherein the tether first end 132 and tether second end 134 may be tensioned so as to straighten the wire 110 into a straight configuration in a pre-deployment configuration.

The anchoring system 100, in accordance with another embodiment, is configured such that the wire first end 112 and the wire second end 114 are operable to fixedly couple together when in the ring configuration.

The anchoring system 100, in accordance with another embodiment, is configured such that the wire first end 112 and the wire second end 114 are operable to engage so as to prevent overlap of the wire first end 112 and the wire second end 114 beyond a complete loop of the wire 110 when in the ring configuration.

The anchoring system 100, in accordance with another embodiment, is configured such that the skirt 120 has tissue ingrowth properties on one side and tissue adhesion-prevention properties on the other side.

The anchoring system 100, in accordance with another embodiment, further includes a tether lock 140 slidingly coupled to the tether 130 being operable to slide along the tether 130 and lock in place so as to capture the heart wall between the tether lock 140 and the anchor 102.

A method of anchoring, in accordance with an embodiment, comprises providing the anchoring system as described above, advancing a guidewire into a femoral vein, advancing the guidewire through the femoral vein and into a right atrium, advancing the guidewire through a septum and into a left atrium, advancing the guidewire through a mitral valve up to and adjacent a heart wall of a left ventricle, advancing a needle catheter over the guidewire and through an endocardium and into a myocardium of the heart wall, advancing the guidewire through the needle catheter through the myocardium and through an epicardium and into a pericardial space, withdrawing the needle catheter from the guidewire, advancing a catheter over the guidewire and into the pericardial space, inflating and separating a pericardium from the heart wall so as to enlarge the pericardial space, advancing the anchoring system either over the guidewire or through the catheter, the anchor of which is placed into the pericardial space, deploying an anchor of the anchoring system within the pericardial space and placing the anchor so as to oppose the epicardium, wherein the anchor is in a straight configuration in a pre-deployment configuration via tension on the tether first end and tether second end, and wherein the anchor is in a ring configuration in a deployed configuration via tension on the tether first end and tether second end, and removing the guidewire and/or catheter from a patient leaving a tether that is coupled to the anchor in a heart chamber.

A method of anchoring, in accordance with an embodiment, comprises providing the anchoring system as described above, advancing a guidewire into a needle catheter such that a guidewire distal tip is adjacent to a needle catheter distal tip, advancing the needle catheter distal tip from a heart chamber through an endocardium and into a myocardium of a heart wall, advancing the guidewire distal tip through the myocardium and the epicardium and into a pericardial space, and advancing the anchor of the anchoring system over the guidewire and into the pericardial space, and deploying the anchor in the pericardial space, wherein the anchor is in a straight configuration in a pre-deployment configuration via tension on the tether first end and tether second end, and wherein the anchor is in a ring configuration in a deployed configuration via tension on the tether first end and tether second end.

A method of anchoring, in accordance with an embodiment, comprises providing the anchoring system as described above, advancing a support catheter into a heart up to and adjacent to or against a heart wall, advancing an anchoring catheter singularly or through the support catheter and placing in urging engagement against the heart wall, advancing a guidewire along or through the anchor catheter through an endocardium through a myocardium and through an epicardium (visceral layer of serous pericardium) of the heart wall and into a pericardial space, advancing the anchor catheter along or over the guidewire and through the endocardium through the myocardium and through the epicardium (visceral layer of serous pericardium) of the heart wall and into the pericardial space, advancing or exposing the anchor of the anchoring system through or at a distal end of the anchor catheter which is in the pericardial space, wherein the anchor is placed into the pericardial space, deploying the anchor of the anchoring system within the pericardial space and placing the anchor so as to oppose the epicardium, wherein the anchor is in a straight configuration in a pre-deployment configuration via tension on the tether first end and tether second end, and wherein the anchor is in a ring configuration in a deployed configuration via tension on the tether first end and tether second end, and removing the guidewire and anchor catheter from a patient leaving a tether that is coupled to the anchor in a heart chamber.

A method of anchoring, in accordance with an embodiment, comprises providing the anchoring system as described above advancing an anchor catheter up to and against a heart wall in a heart chamber, advancing a guidewire through the anchoring catheter such that a guidewire distal tip advances through an endocardium and into a myocardium through the epicardium and into a pericardial space, advancing a distal tip of the anchor catheter along or over the guidewire and into or adjacent to the pericardial space, advancing or exposing the anchor of the anchoring system through or at a distal end of the anchor catheter which is in the pericardial space, wherein the anchor is placed in the pericardial space, deploying the anchor of the anchoring system within the pericardial space and placing the anchor so as to oppose the epicardium, wherein the anchor is in a straight configuration in a pre-deployment configuration via tension on the tether first end and tether second end, and wherein the anchor is in a ring configuration in a deployed configuration via tension on the tether first end and tether second end, and removing the guidewire and anchor catheter from a patient leaving a tether that is coupled to the anchor in a heart chamber of an anchoring system over the guidewire and into the pericardial space.

Figure 21:
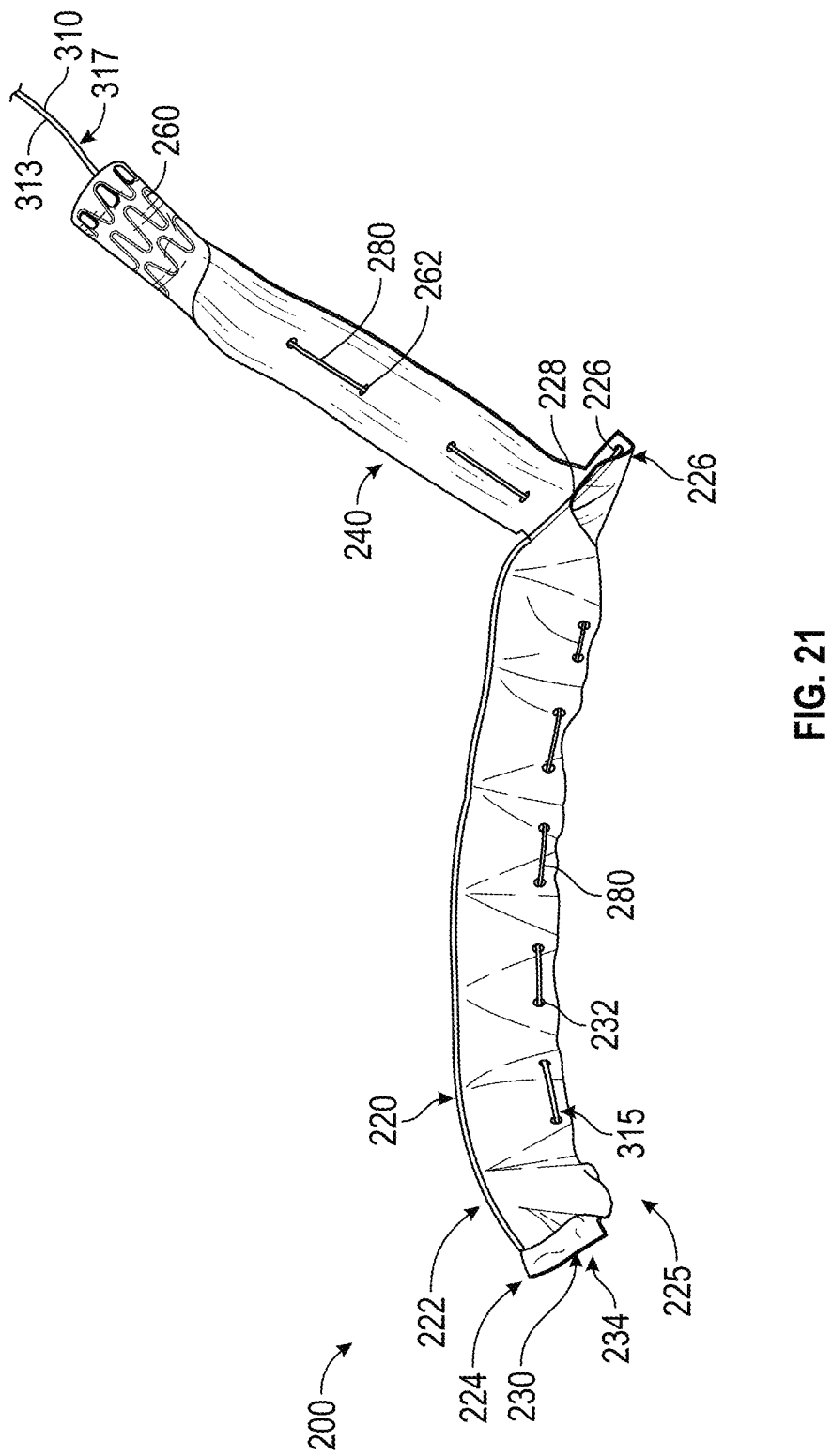
FIG. 21 is an example of a pericardial anchoring system in a laid open configuration, in accordance with an embodiment.
Figure 22:
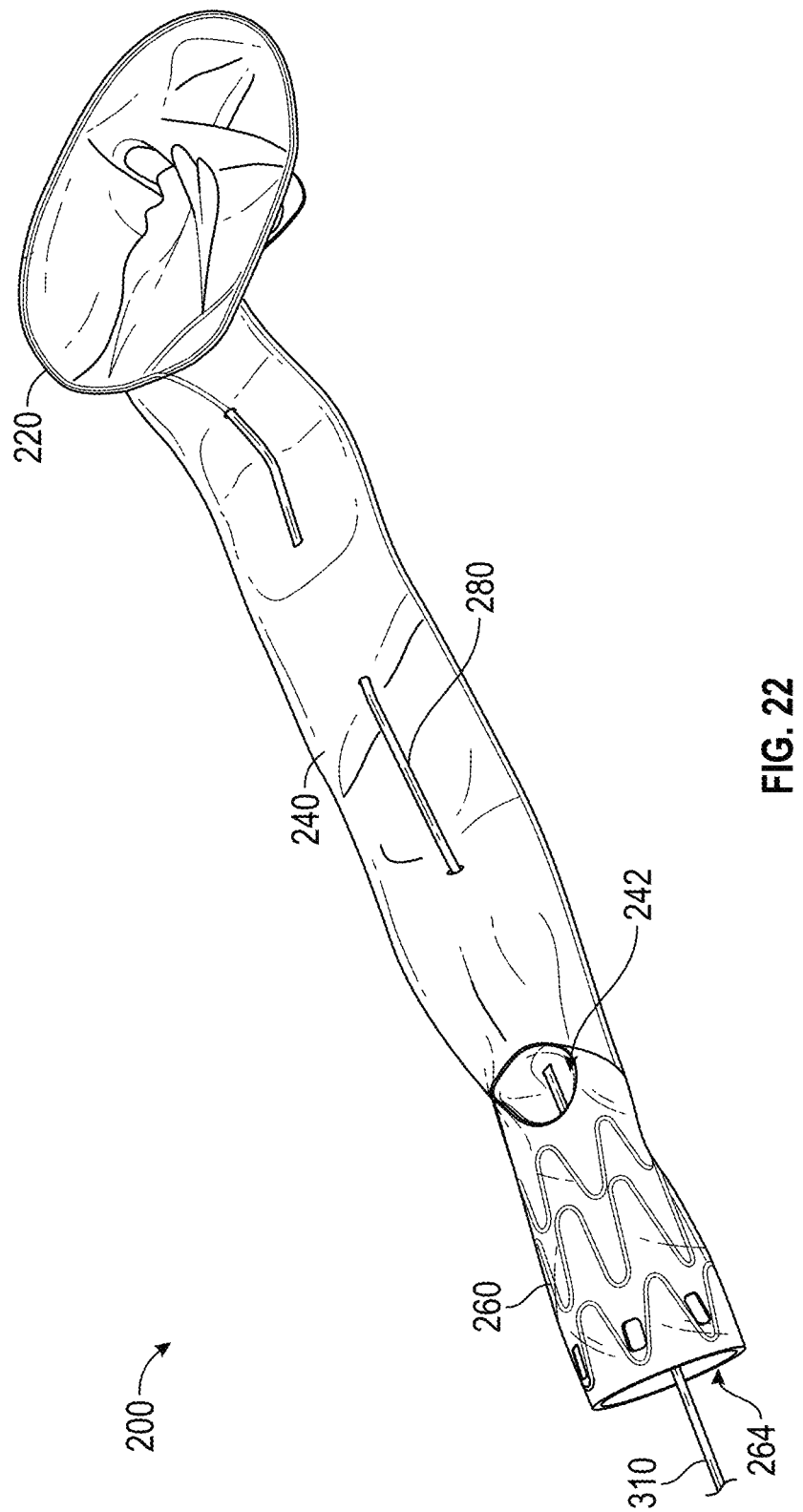
FIG. 22 is an example of the pericardial anchoring system of FIG. 21 wherein the epicardial anchor is in the deployed configuration and the transmyocardial pledget in a predeployed configuration.
Figure 23:
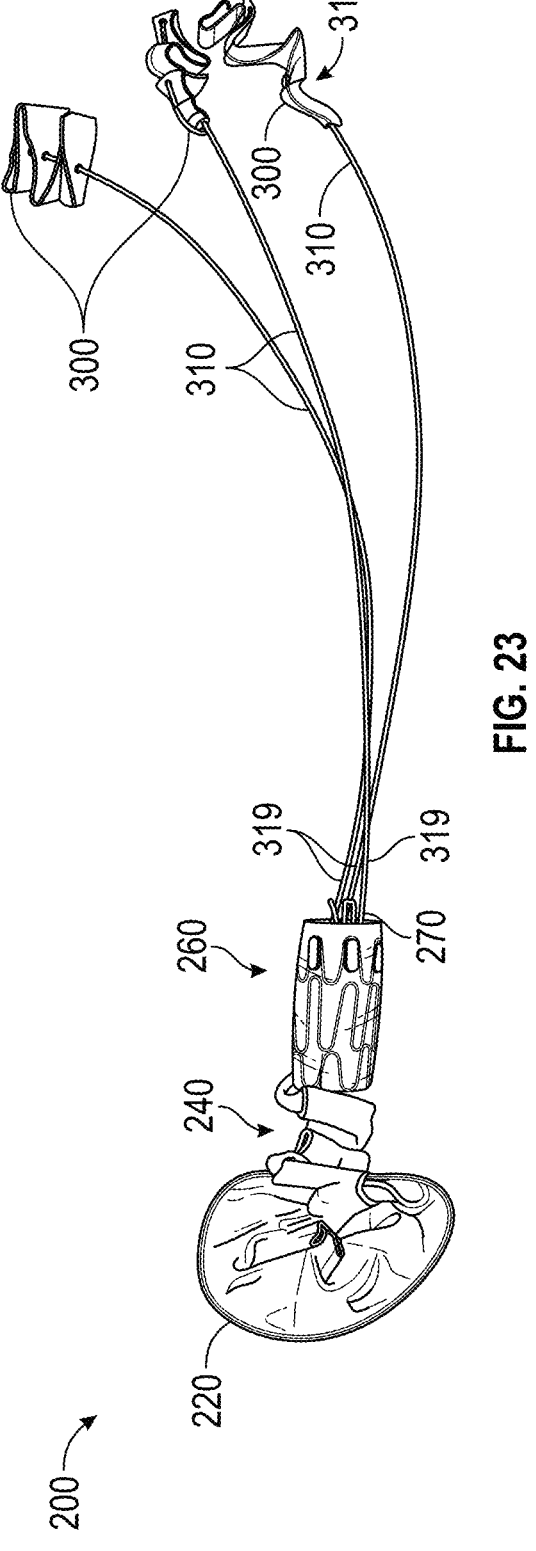
FIG. 23 is an example of the pericardial anchoring system of FIGS. 21 and 22 in a fully deployed configuration.
Figures 29, 30:
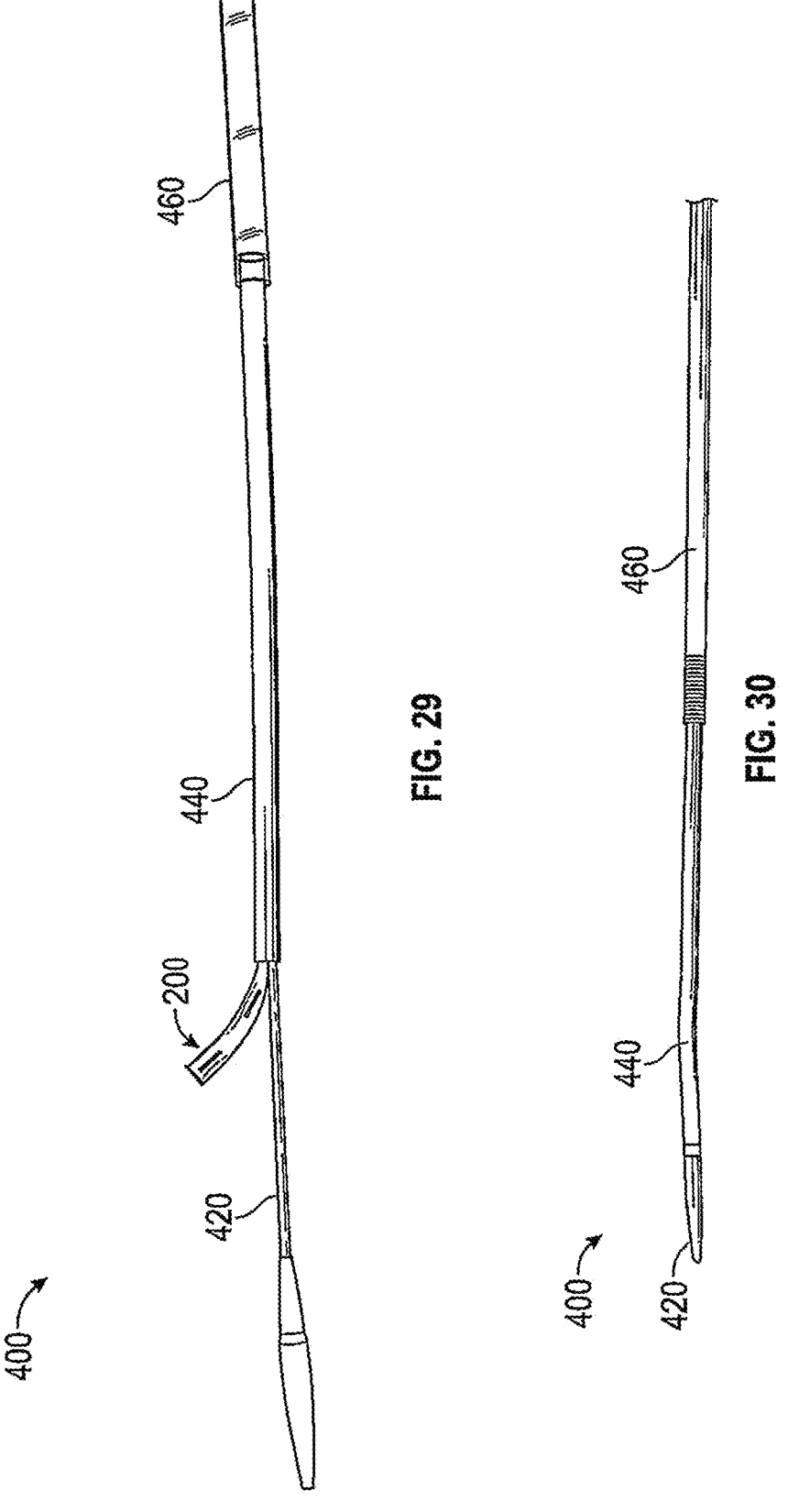
FIG. 29 is an example of a delivery subsystem for a pericardial anchoring system in a first configuration, in accordance with an embodiment.
FIG. 30 is an example of the delivery subsystem for a pericardial anchoring system of FIG. 29 in a second configuration.

FIG. 21 is a side view of an example of a ventricular anchor system or a pericardial anchoring system 200 in a laid open configuration prior to being loaded onto a delivery system. The pericardial anchoring system 200 can be configured to be loaded onto a delivery system and delivered through a catheter. The pericardial anchoring system 200 can include each of the epicardial anchor 220 and the transmyocardial pledget 240 in a straight or elongate configuration. The pericardial anchoring system 200 can be in the elongate configuration as it is loaded and delivered in a catheter presenting a low profile suitable for advancing though a lumen of a catheter such as shown in FIG. 29. FIG. 22 is an example of the pericardial anchoring system 200 wherein the epicardial anchor 220 is in the deployed configuration and the transmyocardial pledget 240 in a predeployed configuration. As shown, the epicardial anchor 220 can be in a deployed configuration. The epicardial anchor 220 in the deployed configuration can be compressed, coiled, wadded, bunched, curled, curved. FIG. 23 is an example of the pericardial anchoring system 200 in a deployed configuration. As shown, the epicardial anchor 220 can be in a coiled configuration and the transmyocardial pledget 240 is in a folded configuration. FIG. 23 further shows the leaflet anchor and the leaflet anchor suture coupled to the pericardial anchoring system 200.

In accordance with an embodiment, the pericardial anchoring system 200 includes an epicardial anchor 220, a transmyocardial pledget 240, an anchor socket 260, and a suture lock 270. The epicardial anchor 220 can be an anchor where at least a portion of the anchor is configured to be positioned in the pericardial space, such that the anchor can resist being pulled through a puncture in the heart wall. At least a portion of the epicardial anchor 220 can be embedded in or in contact with tissue of the heart, such as the epicardium of the heart wall. The epicardial anchor 220 can be an epicardial anchor 220, such that it can achieve a disc, ring, or annular configuration in a deployed configuration. The disc, ring, or annular configuration can be planar or nonplanar (such as a helix or biased shape). The epicardial anchor 220 can also take on a variety of other shapes in the deployed configuration, such as a curved shape, a compressed shape, a bunch, a wad, or a knot. As will be discussed further below, the epicardial anchor 220 can include a wire frame or can be wireless.

Figure 24:
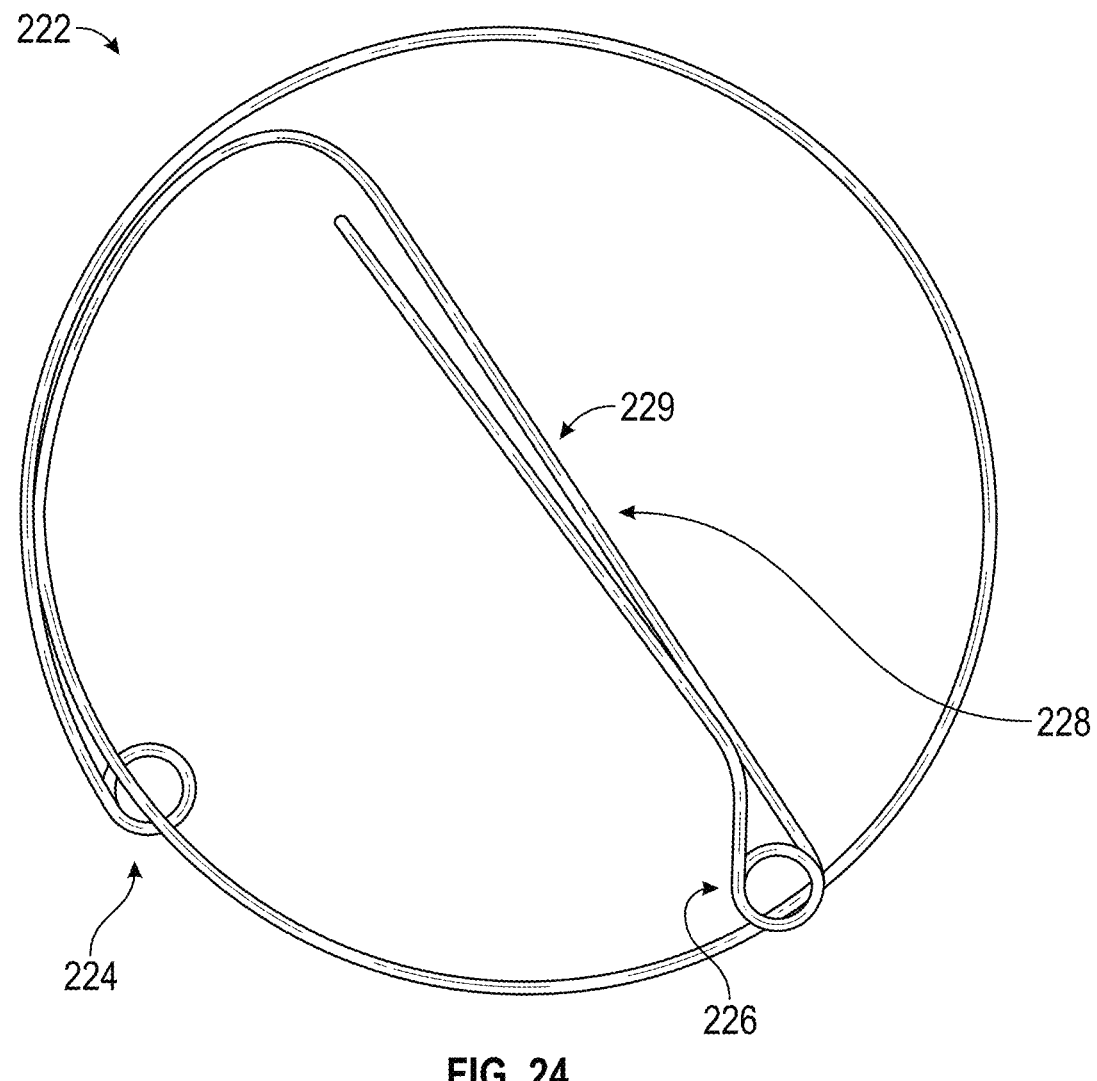
FIG. 24 is an example of the wire frame of the epicardial anchor in a deployed configuration, in accordance with an embodiment.

The epicardial anchor 220 can include a wire or wire frame 222 that is coupled to a skirt 230. FIG. 24 is a plan view of a wire frame 222 that is in an unrestrained curved configuration in accordance with an embodiment. The wire or wire frame 222 can be made of nitinol, such as platinum filled nitinol. The skirt 230 or film, as shown in FIG. 21, can be any suitable biocompatible material, such as, but not limited to, a fluoropolymer film such as expanded polytetrafluoroethylene (ePTFE) and expanded polyethylene (ePE). The skirt 230 can have properties operable to facilitate tissue ingrowth. The wire frame 222 can have a wire first end with a distal eyelet 224 and a wire second end with a proximal eyelet 226. The distal eyelet 224 and the proximal eyelet 226 can be the terminal ends of the wire frame 222. The wire frame 222 can have a proximal leg or t-bar proximal leg 228 at a proximal portion of the wire frame 222 in the straight configuration. The proximal leg 228 can be positioned distal of the proximal eyelet 226 of the wire frame 222 in the straight configuration. The proximal leg 228 can be a straight portion of the wire frame 222 that remains straight in both the straight configuration and the curved configuration, wherein in this embodiment is in a shape of a ring.

The proximal leg 228 can be reinforced, such as to resist a tensile or bearing force, compared the remainder of the wire frame 222. In accordance with an embodiment, the proximal leg 228 can include two portions of the same wire that is doubled up, such that they are parallel to each other and can be touching one another, and can be coupled together. In some embodiments, the proximal leg 228 can have a material property that is stiffer than a remainder of the wire. This advantageously allows the proximal leg 228 to resist bending and remain straight during deployment of the epicardial anchor 220, for example while bearing against a distal end of a delivery catheter, while the remainder of the wire frame 222 can be deployed to form a curved configuration. The proximal leg 228 is configured to remain straight and to seat the epicardial anchor 220 against the delivery catheter distal end 502 and the puncture in the epicardium to retain the epicardial anchor 220 in the pericardial space and to prevent the passage of the proximal leg 228 through the epicardium once in the pericardial space. The proximal leg 228 is operable to prevent the epicardial anchor 220 from being pulled proximally through the puncture in the epicardium.

In accordance with an embodiment, the proximal leg 228 is configured to maintain a straight configuration such that in combination with a curved bias of the remaining portion of the wire frame 222, presents an urging engagement with the delivery catheter so as to assist in deployment of the epicardial anchor 220. In accordance with another embodiment, the proximal leg 228 is configured to maintain a straight configuration such that in combination with the curved bias of the remaining portion of the wire frame 222, presents a profile operable to prevent the anchor from passing through the puncture in the epicardium once deployed.

The skirt 230 can be coupled to the wire frame 222 along an edge defining a length. The wire frame 222 can be positioned on one end or edge of the skirt 230. In one embodiment, a tether or pericardial anchor suture 280 is coupled to an opposite edge of the skirt 230. In accordance with another embodiment, a plurality of anchor apertures 232 are positioned along an edge of the skirt 230 opposite the wire frame 222. The tether or pericardial anchor suture 280 is alternately weaved through the plurality of anchor apertures 232 and slidably received therethrough. A first end of the pericardial anchor suture 280 is configured to be fixedly coupled to a first end of the skirt 230 at a suture attachment 234. The suture attachment 234 can be a reinforced portion of the skirt 230 wherein the reinforced portion is reinforced with additional material or a secondary material added to facilitate and strength the coupling, in accordance with an embodiment. In another embodiment, the reinforced portion may have a different material property, such as, but not limited to, pressure and/or heat densification, such as with a porous material. The suture attachment 234 can be at a distal end or portion of the skirt 230. This can advantageously improve deployment of the epicardial anchor 220 and in retaining tension of the pericardial anchor suture 280. In accordance with an embodiment the suture attachment 234 at a distal end or portion of the skirt 230 in cooperative engagement with the anchor apertures 232 in the skirt 230 results in a predetermined amount of force distribution along the skirt 230 as compared with a more concentrated load at the attachment point located at a more proximal location on the skirt 230, The entire wire frame 222 may be coupled to the skirt 230. In an embodiment, the skirt 230 covers the entire wire frame 222, such as, for example, by being within a fold or hem of the film or embedded within layers of the film, which can improve stability of the epicardial anchor 220 in the event of a fracture or damage of the wire frame 222. The skirt 230 covering the wire frame 222 can additionally prevent the pericardial anchor suture 280 from being misrouted or becoming entangled with the wire frame 222, in particular during transition between the predeployed configuration (such as the elongate configuration) to the deployed configuration (such as a curved configuration) of the epicardial anchor 220.

In other embodiments, instead of weaving the pericardial anchor suture 280 through a plurality of anchor apertures 232, the pericardial anchor suture 280 can be incorporated into the skirt 230 in other ways, such as by being integrated into the skirt 230 itself or by being fixedly attached or slidingly received within a portion of the skirt 230. In some examples, the skirt 230 can include a tunnel or channel that slidingly receives the pericardial anchor suture 280.

In other embodiments, instead of a wire frame 222, a biasing element can be integrated or incorporated into the skirt 230. The biasing element is operable to bias the skirt 230 into a curved configuration. In accordance with an embodiment, the biasing element can be a densified, embossed, or treated portion of the skirt 230 that is operable to have a bias so as to transform the epicardial anchor 220 from a predeployed configuration to a deployed configuration, such as from an elongate configuration to a curved configuration.

The epicardial anchor 220 can be maintained in the straightened configuration against the bias of the wire frame 222 in the predeployed configuration by applying tension to a suture distal end 315 of the pericardial anchor suture 280 and/or a suture proximal end 317 of the pericardial anchor suture 280 that extends through the skirt 230, as shown in FIG. 21. The pericardial anchor suture 280 can be operable to be tensioned so as to cinch the skirt 230 into a curve, disk, or annular shape when the wire frame 222 is in a deployed configuration. The pericardial anchor suture 280 may be operable to cinch the skirt 230 such that the skirt 230 extends across the curvature of the wire frame 222 to completely cover the central portion defined by the wire frame 222.

Whether the skirt 240 has a biasing member, such as a wire frame 222, or not, the deployed configuration may attain a coiled, wadded, bunched, ring, annular, knotted, among other configurations. The deployed configurations are operable to provide one or more functions, such as, but not limited to, prevent pull-through the puncture in the heart wall. And/or to distribute loading caused by tension on the suture to a broader area of the vessel wall. And/or to provide a suitable surface for tissue ingrowth and/or overgrowth in a healing response.

In some examples, the suture proximal end 317 of the pericardial anchor suture 280 is tensioned, such as in a proximal direction, to cinch the skirt 230 into a deployed configuration (such as a compressed, coiled, curved, curled, ring, annular, knotted, bunched, or wadded shape) when the epicardial anchor 220 is in the deployed configuration. The biasing force of the biasing member, which is biased to pull the skirt into a curved configuration. Tension on the pericardial anchor suture 280 may assist in the curvature of the biasing member and/or assist in ensuring a complete deployed configuration (such as a curved or ring configuration). The epicardial anchor 220 can be transitioned between the predeployed configuration (such as an elongate configuration), such as shown in FIG. 21, to the deployed configuration (such as a coiled configuration), such as shown in FIGS. 22 and 23. This transition can be at least partially facilitated by tension being applied to the pericardial anchor suture 280 or the bias of the biasing element, such as the wire frame 222, or both.

In accordance with an embodiment, the wire frame 222 has a shape memory property that is shape-set to a curved or a ring or annular configuration, as shown in FIG. 24. As shown in FIG. 24, when the epicardial anchor 220 is in a deployed state, the t-bar or proximal leg 228 remains straight and the remainder of the wire frame 222 is biased to conform to a curved configuration in the deployed, that is, unconstrained, configuration. The t-bar proximal leg 228 can be positioned in the center of the epicardial anchor 220 in the deployed configuration in the curved configuration. The t-bar proximal leg 228 can be positioned to overlay the center of the curve defined by the epicardial anchor 220 such that, in accordance with an embodiment, it extends across the diameter of the epicardial anchor 220 when in the ring configuration. The wire frame 222 can be configured such that a portion of the wire frame 222 overlaps with another portion of the wire frame 222. For example, a distal portion of the wire frame 222 which includes the distal eyelet overlaps with another portion of the wire frame 222, such as around a circumference of the epicardial anchor 220 in the deployed state. The distal eyelet 224 can be positioned to overlay the circumference of the epicardial anchor 220 in the deployed configuration. The proximal eyelet 226 can be positioned at or near the end of the t-bar proximal leg 228 or at a double-back portion 229 and overlay or lie adjacent to the circumference of the epicardial anchor 220 in the deployed configuration. The distal eyelet 224 and the proximal eyelet 226 can provide atraumatic ends of the wire frame 222 that prevent damage to the delivery system and/or adjacent tissue, such as during deployment of the epicardial anchor 220 or once the epicardial anchor 220 is implanted in the pericardial space. In other examples, the epicardial anchor 220 can have other types of atraumatic ends instead of eyelets, such as rounded or blunt ends. The atraumatic ends can advantageously prevent damage to the tissue during implantation or to the other portions of the anchor system, such as to the skirt 230.

In some configurations, the wire frame 222 can be biased to form a helix when in the curved configuration in the deployed configuration. This bias towards a helix can advantageously prevent the wire frame 222 from becoming entangled with itself, other components of the anchor system or the area of implantation. The helix configuration can assist in allowing the epicardial anchor 220 to transform to a coiled configuration. In some configurations, the wire frame 222 has a bias to conform the epicardial anchor 220 so as to define a substantially planar disk when in the deployed configuration.

In other embodiments, instead of a coiled configuration as shown in FIGS. 22 and 23, the epicardial anchor 220 can transition from a predeployed configuration (such as an elongate configuration) suitable for pre-deployed configuration such as within a catheter to a deployed configuration (such as a ring, coiled, curved, compressed, bunched, or wadded configuration) in a variety of ways. For example, the epicardial anchor 220 can begin to curve or coil beginning or initiating from a free end of the epicardial anchor 220 to form a deployed shape, such a disc-like shape. The free end can be a distal end of the epicardial anchor 220, which can be the distal terminal end of both the epicardial anchor 220 and the pericardial anchoring system 200. The coiling that can occur can be partial to form a partial disc shape, complete to form a full disc shape, overlapping to form a full disc shape. The disc-like shape may have a low profile so as to not significantly abut the visceral pericardium or otherwise significantly interfere with the pericardium. The size of the disc-like shape may be configured operable to prevent the epicardial anchor 220 from pulling through the heart wall through the puncture or channel in the myocardium from the delivery subsystem 400 or the pericardial anchor suture 280. The size of the disc-like shape may be configured operable to atraumatically distribute the forces that are on the epicardial anchor 220 and surrounding tissue onto which is in abutment caused by the tension on the remaining portions of the pericardial anchoring system 200. In accordance with an embodiment, the disc shape is ideal as it avoids stress concentrations, such as associated with sharp bends for example, in the wire frame 222 that can result in fracture when fatigued. In accordance with other embodiments, the shape of the anchor may define other shapes, such as, but not limited to, square, cross, and diamond shapes. The wire frame 222 of the epicardial anchor 220 is operable to straighten out and return to a low profile, high surface area shape which is advantageous for delivery and deployment of the epicardial anchor 220. The epicardial anchor 220 defining a surface area within the disc-like shape also promotes tissue ingrowth and/or distributes loading on the pericardial anchoring system 200 over a larger area of the heart surface.

In some embodiments, the epicardial anchor 220 can be bunched or wadded to achieve a deployed configuration. For example, the epicardial anchor 220 in the elongate configuration can be folded, compressed, bunched, curled, or wadded to form a deployed configuration.

As described above, the pericardial anchoring system 200 can also include a pericardial anchor suture 280. The pericardial anchor suture 280 can extend through each of the epicardial anchor 220 and a transmyocardial pledget 240. The pericardial anchor suture 280 can be coupled to the skirt 230, such as, but not limited, by weaving through or integrated with the skirt 230 of the epicardial anchor 220. As shown in FIG. 21, the pericardial anchor suture 280 can be weaved through a plurality of anchor apertures 232 through the skirt 230. The pericardial anchor suture 280 can extend from the skirt 230 of the epicardial anchor 220 to then be weaved through the transmyocardial pledget 240. The transmyocardial pledget 240 can also include a plurality of pledget apertures 262 and the pericardial anchor suture 280 can be weaved through the plurality of pledget apertures 262. The pericardial anchor suture 280 can be made of any suitable biocompatible material, such as, but not limited to fluoropolymer fibers.

The pericardial anchoring system 200 can include a pledget as disclosed in International Application No. PCT/US2020/032054 or International Application No. PCT/US2020/032168 (the entireties of which are incorporated by reference herein) and the various embodiments of pledgets disclosed therein. The transmyocardial pledget 240 can include a film. The film can be a fluoropolymer, which can have tissue ingrowth properties. The film of the transmyocardial pledget 240 can have a tubular structure. The transmyocardial pledget 240 can include a plurality of pledget apertures 262 positioned along the length of the transmyocardial pledget 240. The pericardial anchor suture 280 can be weaved through or integrated in the film of the transmyocardial pledget 240. As shown in FIGS. 21 and 22, the pericardial anchor suture 280 can be weaved through a plurality of pledget apertures 262 through the film of the transmyocardial pledget 240. The pericardial anchor suture 280 can allow the transmyocardial pledget 240 to convert from a straighter configuration, such as shown in FIG. 21, to a curved configuration, such as shown in FIG. 23. For example, tension or retraction of the pericardial anchor suture 280 can compress or fold down the material of the transmyocardial pledget 240 in an accordion-like manner. The transmyocardial pledget 240 may incorporate pleats so as to facilitate folding during the deployment of the transmyocardial pledget 240.

As shown in FIG. 21, the epicardial anchor 220 can be positioned at a distal end of the pericardial anchoring system 200 and the transmyocardial pledget 240 can be positioned proximally from the epicardial anchor 220. The transmyocardial pledget 240 can extend from the proximal leg 228 of the epicardial anchor 220. The transmyocardial pledget 240 can be directly laminated or otherwise coupled to the proximal leg 228 of the wire frame 222 of the epicardial anchor 220. This advantageously allows the proximal leg 228 to be positioned across the puncture in the epicardium while positioning the transmyocardial pledget 240 through the puncture in the epicardium and myocardium. The transmyocardial pledget 240 is operable to seal the puncture in the heart wall. In some configurations, the epicardial anchor 220 and the transmyocardial pledget 240 can extend at an angle from one another in the pre-deployed configuration, as shown in FIG. 21. In some configurations, the epicardial anchor 220 and the transmyocardial pledget 240 can extend linearly with respect to each other.

Figures 35, 36:
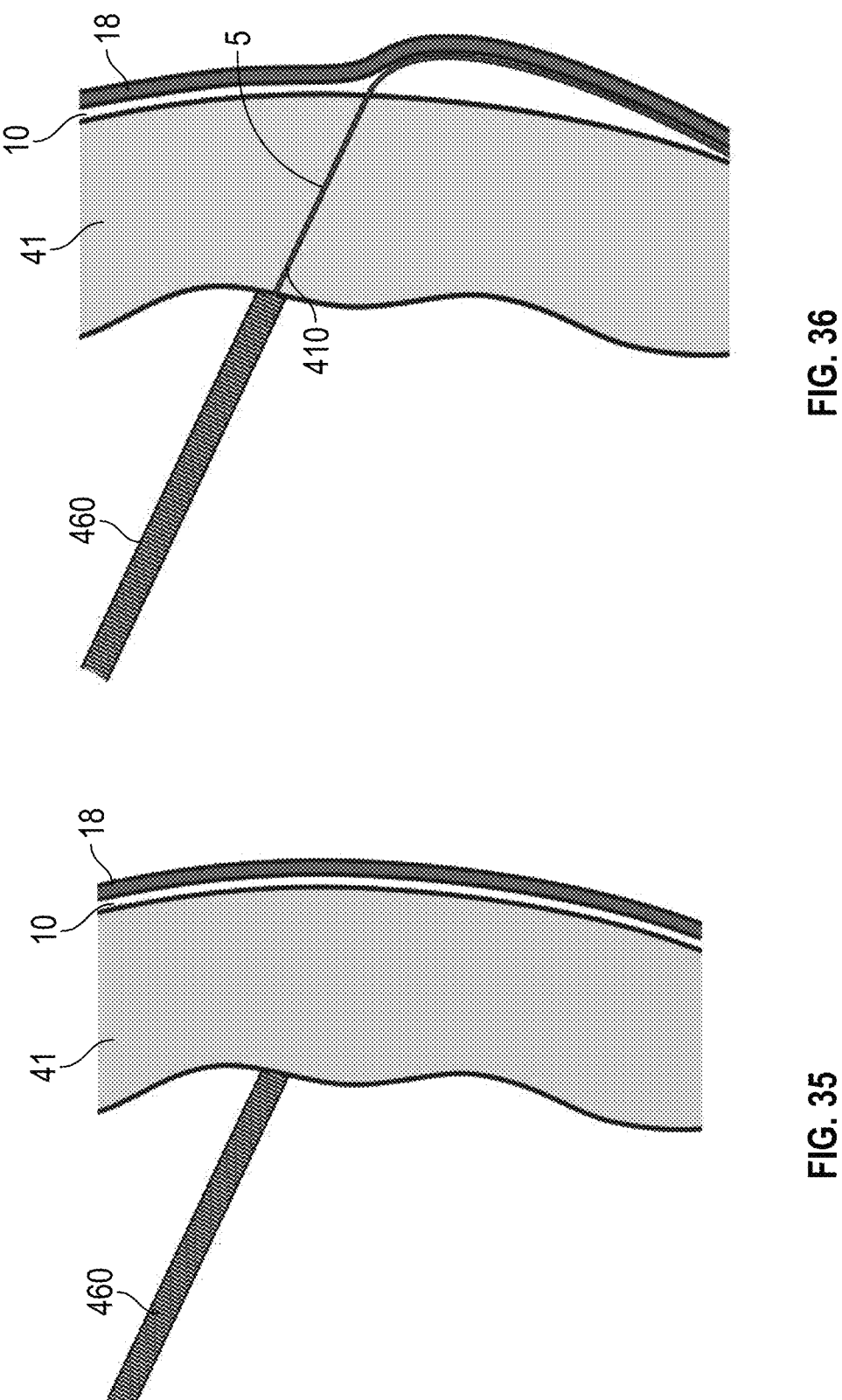
FIG. 35 is a cross-sectional view of the heart wall with the support sheath of the delivery subsystem in accordance with an embodiment of the method of providing a pericardial anchoring system.
FIG. 36 is a cross-sectional view of the heart wall with a guidewire of the delivery subsystem in accordance with an embodiment of the method of providing a pericardial anchoring system.

The transmyocardial pledget 240 is configured to extend from the epicardial anchor 220 and through punctures of the epicardium, myocardium, and endocardium, also referred to as the heart wall channel 5, as shown in FIG. 36. The transmyocardial pledget 240 can fill and seal the heart wall channel 5 defined in the epicardium, myocardium, and endocardium by the delivery system traversing the heart wall to access the pericardial space. The transmyocardial pledget 240 is configured to expand into the puncture in the myocardium to seal the puncture of the myocardium. The portion of the transmyocardial pledget 240 that is positioned through the heart wall channel 5 of the myocardium can be extended in a straightened configuration, while the material of the transmyocardial pledget 240 that is positioned adjacent the endocardium can be collapsed or folded down to seal across the heart wall channel 5 at the endocardium. This advantageously allows the transmyocardial pledget 240 to accommodate different myocardial thicknesses by collapsing down to the endocardium and/or expanding to a diameter that is sufficient to precent leakage through the heart wall channel 5.

The pericardial anchoring system 200 can further include an anchor socket 260 which can hold a suture lock 270. The pericardial anchoring system 200 can include a suture lock as disclosed in U.S. Pat. No. 9,877,833. The pericardial anchoring system 200 can include a suture lock and socket as disclosed in International Application No. PCT/US2021/035423 or U.S. application Ser. No. 16,711,321 (the entireties of which are incorporated by reference herein) and the various embodiments of suture locks or sockets disclosed therein. The pericardial anchoring system 200 can include a socket as disclosed in U.S. application Ser. No. 16/710,637 (the entirety of which is incorporated by reference herein) and the various embodiments of suture locks or sockets disclosed therein. The suture lock 270 can be used to secure each of the pericardial anchor suture 280 and the leaflet anchor sutures 310. The suture lock 270 can also be used to tension and adjust the length of each of the pericardial anchor suture 280 and the leaflet anchor sutures 310. Once the lengths have been optimized to achieve adequate tension for the mitral chord repair, the suture lock 270 can be locked to fix the length of each of the pericardial anchor suture 280 and the leaflet anchor sutures 310.

As used herein, the term "socket" is inclusive of and may be used interchangeably with any of the following terms: covers, receptacles, shrouds, couplers, constrainers, retaining members and the like. In accordance with an embodiment, the anchor socket 260 can have a tubular structure that can receive and at least partially cover the suture lock 270. The anchor socket 260 can include a self-expanding frame that can minimize the profile of the anchor socket 260 when in the predeployed configuration on the delivery system. The self-expanding frame can be a stent frame made of nitinol. The self-expanding frame can be tapered to facilitate docking of the suture lock 270 within the anchor socket 260 and more tightly constrain the anchor socket 260 around the sutures 280, 310. The anchor socket 260 can further include gold marker bands around the circumference of the anchor socket 260 which can provide visual guidance. The self-expanding frame can be covered with fluoropolymer film. In some configurations, the inner surface of the stent frame can be covered with the fluoropolymer film. This film can extend proximally from the film of the transmyocardial pledget 240. The anchor socket 260 can have a length that exceeds the length of the suture lock 270 to ensure full coverage of the suture lock 270 by the anchor socket 260. The anchor socket 260 can be a retaining member to constrain motion of the suture lock relative to the remainder of the pericardial anchoring system 200, as well as motion of the sutures relative to the suture lock 270. The anchor socket 260 can also be called a suture lock guide, socket, or sleeve. The anchor socket 260 can reduce wear on each of the pericardial anchor suture 280 and the leaflet anchor sutures 310 which can ensure the tension in the sutures. The anchor socket 260 can couple the pericardial anchoring system 200 and the suture lock.

As shown in FIGS. 21-23, the anchor socket 260 and suture lock 270 can extend or be positioned proximally from the transmyocardial pledget 240. This position of the anchor socket 260 advantageously facilitates the folding and collapsing of the transmyocardial pledget 240 between the endocardial surface and the anchor socket 260.

Figures 31, 32:
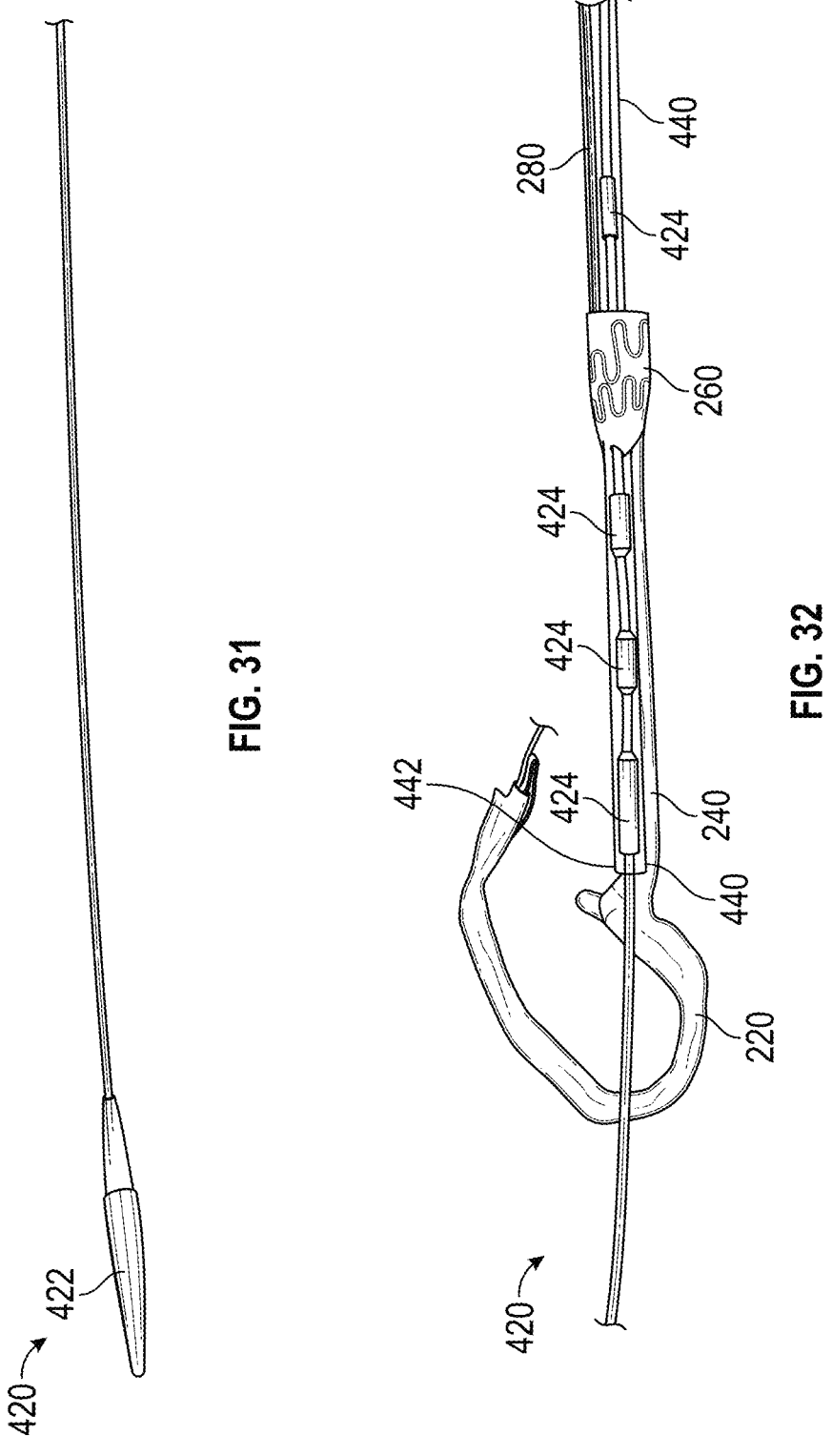
FIG. 31 is an example of the guide wire sheath of the delivery subsystem for a pericardial anchoring system of FIGS. 29 and 30, in accordance with an embodiment.
FIG. 32 is an example of the delivery subsystem with the pericardial anchoring system, in accordance with an embodiment.

As shown in FIG. 22, the transmyocardial pledget 240 can also include a catheter access hole 242 at a proximal end of the transmyocardial pledget 240 and adjacent the anchor socket 260. The catheter access hole 242 in the transmyocardial pledget 240 advantageously allows the egress of catheter components, such as, but not limited to the guidewire sheath 420 and/or the anchor sheath 440 of the delivery subsystem 400, to exit a socket lumen 264 of the anchor socket 260, as shown in FIG. 22, and extend along the transmyocardial pledget 240 and the epicardial anchor 220, as shown in FIG. 32.

Figures 25A, 25B:
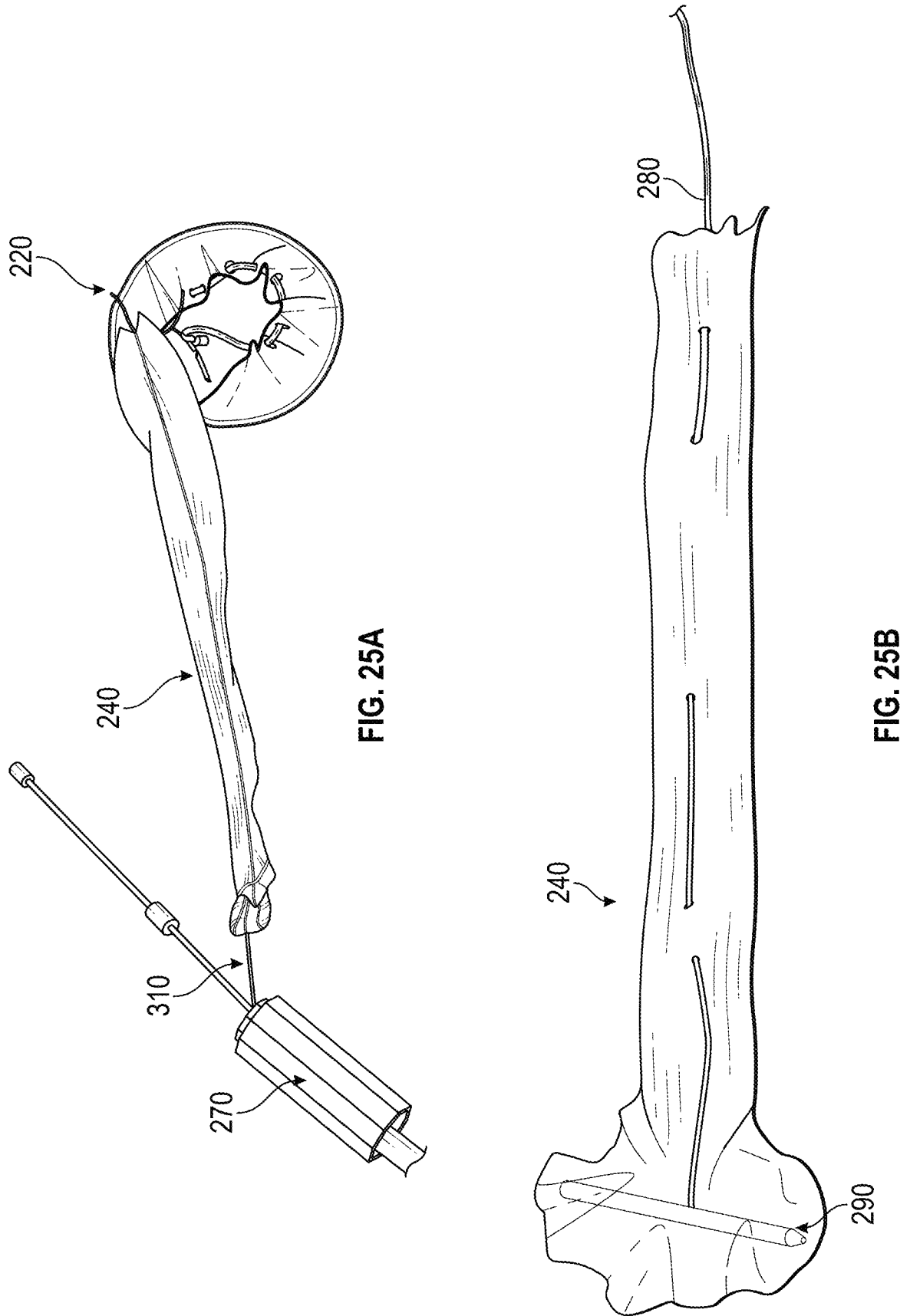
FIG. 25A is an example of a pericardial anchoring system with a suture lock, in accordance with an embodiment.
FIG. 25B is an example of a pericardial anchoring system with a t-bar epicardial anchor in accordance with an embodiment.

FIG. 25A is an example of a ventricular anchor system with a separated socket. The anchor socket 260 can be separate from the remainder of the pericardial anchoring system 200. The anchor socket 260 can be positioned proximally from and connected to the transmyocardial pledget 240, but the anchor socket 260 can be separate in that it is configured to translate relative to the transmyocardial pledget 240.

Instead of the epicardial disc anchor, various types of ventricular anchors or epicardial anchors can assume various shapes besides a disc or annular shape. The ventricular or epicardial anchor can be a pull-string anchor in which a suture can be tensioned or retracted to convert the anchor from a predeployed configuration to a deployed configuration. The predeployed configuration can be an elongate configuration. The deployed configuration can take a variety of shapes, such as a as described above, including a disc, annular, curved, compressed, bunched, wadded, or knotted shape. FIG. 25B is an example of a pericardial anchor system with a t-bar epicardial anchor. The ventricular anchor system in FIG. 25B can be similar to the pericardial anchoring system 200 described above. However, instead of the wire frame 222 and skirt 230 of the epicardial anchor 220, the ventricular anchor system in FIG. 25B can include a t-bar epicardial anchor that includes a t-bar 290 that is covered with a film. The t-bar 290 can function similarly to the t-bar proximal leg 228 of the epicardial anchor 220. The t-bar 290 can be positioned against the puncture in the myocardium in the epicardial cavity. The t-bar 290 covered with a film can be integrated or separated with the transmyocardial pledget 240.

Figure 26A:
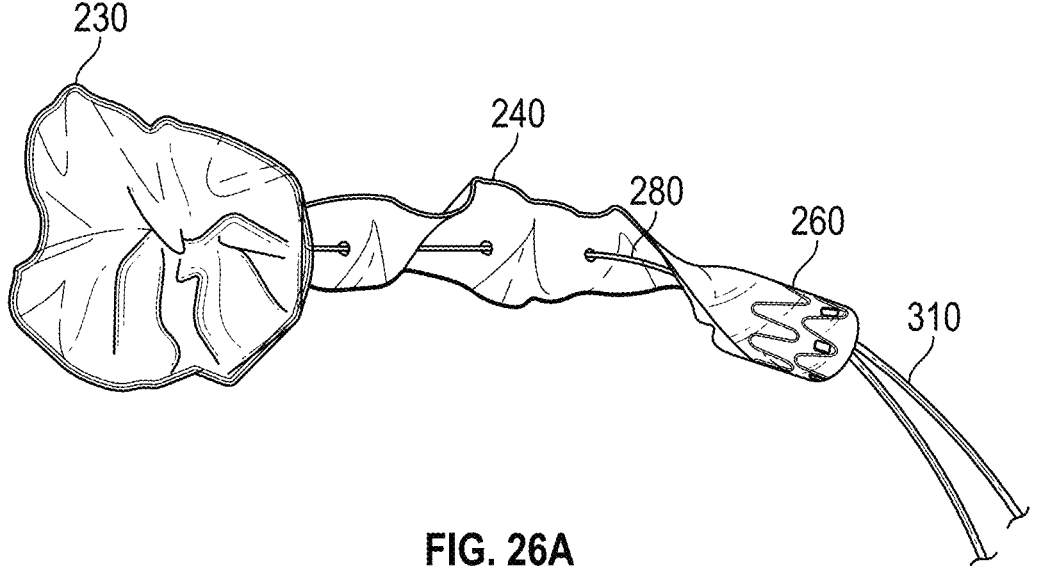
FIG. 26A is an example of a pericardial anchoring system with a frameless epicardial anchor in accordance with an embodiment.

FIG. 26A is an example of a pericardial anchor system with a frameless epicardial anchor. The ventricular anchor system in FIG. 25B can be similar to the pericardial anchoring system 200 described above. However, instead of the wire frame 222 and skirt 230 of the epicardial anchor 220, the ventricular anchor system in FIG. 25B can include a wireless skirt 230 or film. The wireless skirt 230 can function similarly to the skirt 230 of the epicardial anchor 220. The pericardial anchor suture 280 can be integrated or weaved through the wireless skirt 230. The pericardial anchor suture 280 can be tensioned to cinch the wireless skirt 230 into a disc, ring, or bunched wad configuration in a deployed configuration, such as shown in FIG. 26A.

Figure 26B:
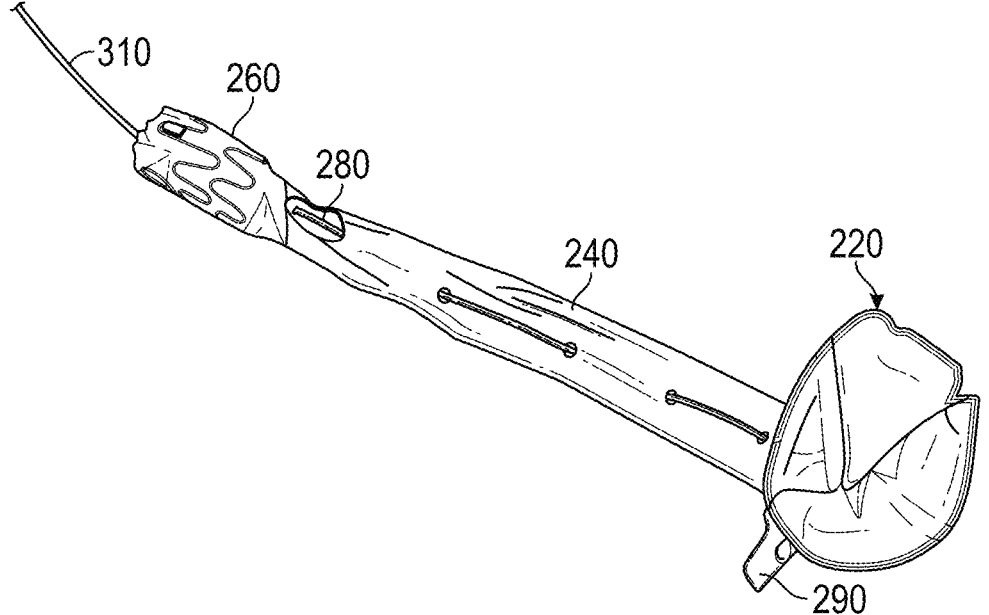
FIG. 26B is an example of a pericardial anchoring system with a t-bar and frameless epicardial anchor in accordance with an embodiment.

FIG. 26B is an example of a pericardial anchor system with a t-bar and frameless epicardial anchor. The ventricular anchor system in FIG. 25B can be similar to the pericardial anchoring system 200 described above. However, instead of the wire frame 222 and skirt 230 of the epicardial anchor 220, the pericardial anchor system in FIG. 25B can include a t-bar proximal leg 228 covered by a film or wireless skirt 230. The t-bar covered by the film/skirt can extend proximally from the wireless skirt 230. The t-bar 290 can function similarly to the t-bar proximal leg 228 of the epicardial anchor 220. The t-bar 290 can be positioned against the puncture in the myocardium in the epicardial cavity. The t-bar 290 covered with a film or skirt can be integrated or separated with the transmyocardial pledget 240. The wireless skirt 230 can function similarly to the skirt 230 of the epicardial anchor 220. The pericardial anchor suture 280 can be integrated or weaved through the wireless skirt 230. The pericardial anchor suture 280 can be tensioned to cinch the wireless skirt 230 into a ring configuration in a deployed configuration, such as shown in FIG. 26A.

The wireless skirt 230 can function similarly to the skirt 230 of the epicardial anchor 220. The pericardial anchor suture 280 can be integrated or weaved through the wireless skirt 230. The pericardial anchor suture 280 can be tensioned to cinch the wireless skirt 230 into a disc, ring, curved, or bunched wad configuration in a deployed configuration, such as shown in FIG. 26A.

Figure 27:
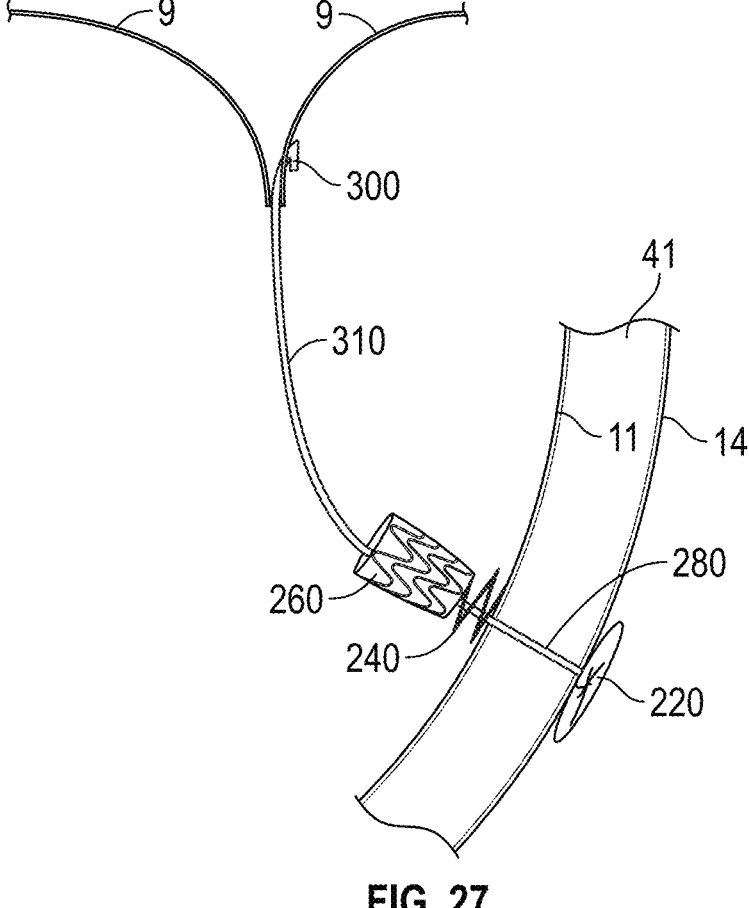
FIG. 27 is an example of the pericardial anchoring system and a leaflet anchoring system deployed and implanted in the heart in accordance with an embodiment.

FIG. 27 is an example of the pericardial anchoring system 200 deployed and partially implanted in position in the ventricle of the heart. As shown, the epicardial anchor 220 in the ring configuration is positioned in the pericardial space. The epicardial anchor 220 can anchor the pericardial anchoring system 200 and act as a mechanical interface to anchor the pericardial anchoring system 200. The epicardial anchor 220 can also act to seal one end of the myocardial puncture. The transmyocardial pledget 240 extends from the epicardial anchor 220 with a portion extending through the heart wall 41 and a portion folded down against the endocardium layer of the heart wall 41. The suture lock 270 positioned within the anchor socket 260 can be positioned against the folded down portion of the transmyocardial pledget 240. The suture lock 270 enclosed by the anchor socket 260 can drive the anchor socket 260 to the endocardial surface, which can also encourage sealing of the puncture on the endocardial surface by the folded down portion of the transmyocardial pledget 240. The pericardial anchor suture 280 can extend through the epicardial anchor 220, through the transmyocardial pledget 240, and into the suture lock 270. The pericardial anchor suture 280 can also act as a tension member for forming the epicardial anchor 220. The pericardial anchor suture 280 can provide a rail to connect the suture lock 270. The transmyocardial pledget 240 can protect the heart wall 41 from damage due to the pericardial anchor suture 280. The transmyocardial pledget 240 adds bulk to the pericardial anchor suture 280 which, by itself, might tend to cut or slice through the myocardium with the application of tension or loading. The transmyocardial pledget 240 prevents the migration of the pericardial anchor suture 280 within the myocardium. The transmyocardial pledget 240 can create the myocardial seal by plugging the channel or puncture through the heart wall 41 and by folding up to seal the opposite end of the puncture on the endocardial surface. The suture lock 270 can also capture the leaflet anchor suture 310. The leaflet anchor suture 310 can extend between the leaflet anchor 300 implanted in a leaflet 9 and the suture lock 270 to repair a mitral chord.

Figures 28A, 28B, 28C:
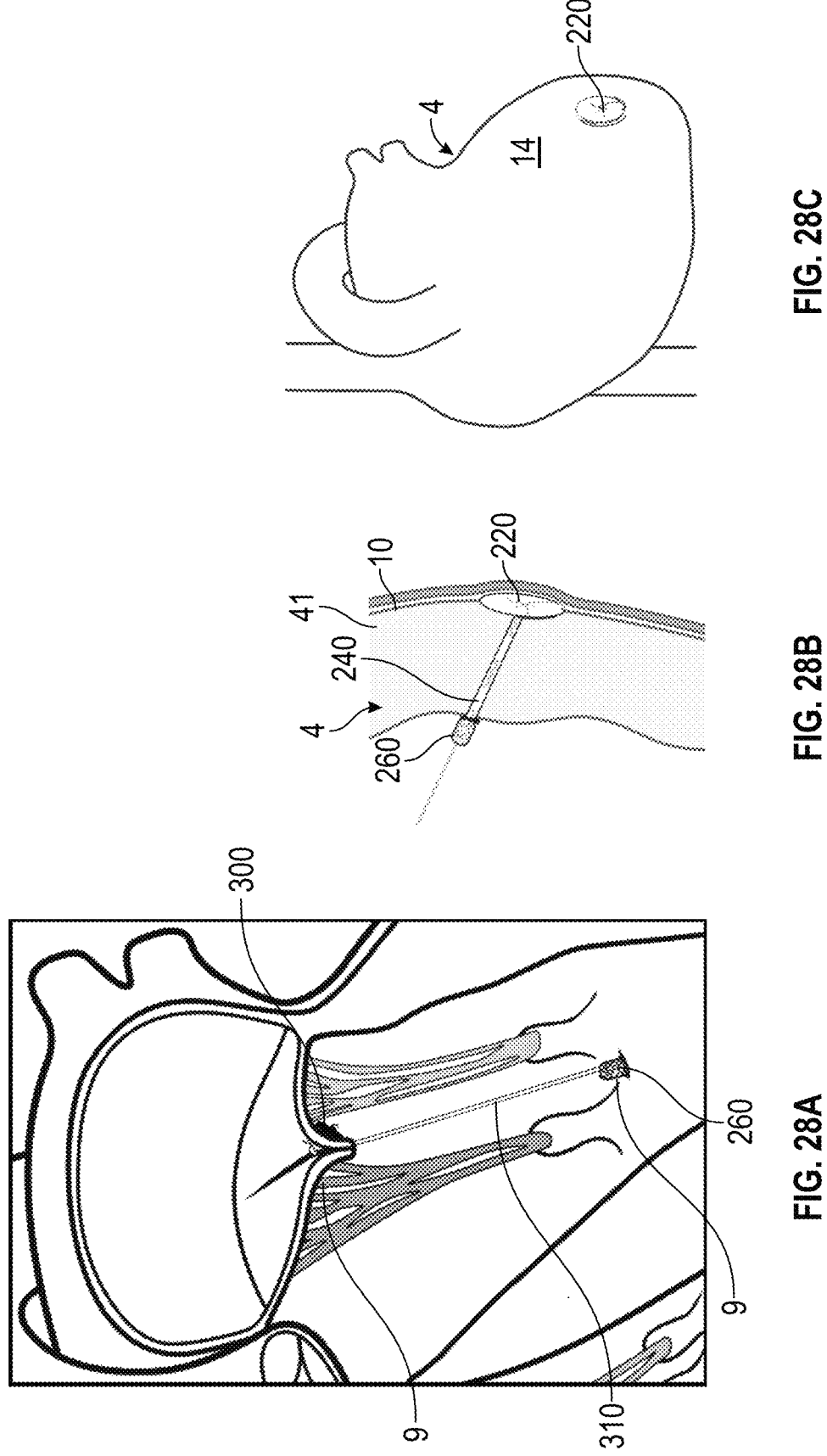
FIG. 28A is an example of the leaflet anchor implanted in the valve leaflet and the leaflet anchor suture extending between the leaflet anchor and the pericardial anchoring system implanted in the ventricular wall, in accordance with an embodiment.
FIG. 28B is a cross sectional view of the ventricular wall with the pericardial anchoring system implanted, in accordance with an embodiment.
FIG. 28C is a view of the epicardial anchor implanted within the pericardial cavity (not showing the pericardium for clarity), in accordance with an embodiment.

FIG. 28A is an example of the leaflet anchor implanted in the valve leaflet and the leaflet anchor suture 310 extending between the leaflet anchor 300 and the pericardial anchoring system 200 implanted at least in the ventricle wall. As shown, the pericardial anchoring system 200 is implanted in the ventricle wall, such that the anchor socket 260 is positioned against the endocardial surface of the heart wall 4s. The leaflet anchor 300 can be an anchor where at least a portion of the anchor is configured to be positioned in or on a leaflet. At least a portion of the epicardial anchor 220 can be embedded in or in contact with tissue of the leaflet. The leaflet anchor 300 can be a variety of shapes, such as a pledget, a clip, or a hook. The leaflet anchor suture 310 can extend from the suture lock 270 positioned within the anchor socket 260 and extend to the leaflet anchor 300. The leaflet anchor 300 can be an anchor positioned within the mitral valve leaflet 9. The leaflet anchor 300 can be a pledget.

FIG. 28B is a cross sectional view of the ventricular wall with the ventricular anchor system implanted. As shown, the epicardial anchor 220 can be positioned within the pericardial space 10. The transmyocardial pledget 240 can extend from the epicardial anchor 220, and through the puncture of the endocardium, myocardium, and epicardium. The transmyocardial pledget 240 can also be folded down against the endocardial surface of the heart wall 41. The anchor socket 260 can be positioned against the endocardium of the heart wall 41.

FIG. 28C is a view of the epicardial anchor 220 implanted within the pericardial space.

FIG. 29 is an example of a delivery system or delivery subsystem 400 in a first configuration. FIG. 30 is an example of the delivery subsystem 400 of FIG. 29 in a second configuration. FIG. 31 is an example of the guide wire sheath of the delivery subsystem 400 of FIGS. 29 and 30.

The delivery subsystem 400 can be delivered through a delivery catheter. The delivery subsystem 400 can include three catheters or sheaths, including a support sheath 460, an anchor sheath 440, and a guidewire sheath 420. The delivery subsystem can further include a guidewire 410 configured to be delivered through the guidewire sheath 420. The sheaths 420, 440, 460 can be configured to fit within each other or nested within one another. The support sheath 460 can be an outer sheath that receives the anchor sheath 440. The anchor sheath 440 can be an intermediate sheath that is received by the support sheath 460 and receives the guidewire sheath 420. The guidewire sheath 420 can be received be received by the anchor sheath 440 and receives the guidewire 410. FIG. 29 shows the guidewire sheath 420 pulled farther out distally from the anchor sheath 440 than as shown in FIG. 30. The guidewire 410 can be positioned within an inner circumference of the guidewire sheath 420. This allows delivery of the guidewire 410 through the guidewire sheath 420. The pericardial anchoring system 200 can be positioned between the outer circumference of the guidewire sheath 420 and the inner circumference of the anchor sheath 440. This allows delivery of the pericardial anchoring system 200 by retraction of the anchor sheath 440.

FIG. 32 is an example of the guidewire sheath 420 with the pericardial anchoring system 200. The anchor sheath 440 has been retracted. As shown in FIG. 32, the pericardial anchoring system 200 can be positioned on an outer surface of the guidewire sheath 420. The guidewire sheath 420 can include a plurality of sleeves 424 on the outer surface of the guidewire sheath 420 and between portions of the pericardial anchoring system 200 to constrain portions of the pericardial anchoring system 200. For example, the sleeves 424 can be positioned on either side of the anchor socket 260 of the pericardial anchoring system 200. The sleeves 424 can aid in advancing or positioning various portions of the ventricular anchor system. For example, a sleeve 424 can be positioned proximal to the epicardial anchor 220 and can enable advancement of the epicardial anchor 220 with advancement of the guidewire sheath 420. For example, a sleeve 424 can be positioned proximal to the epicardial anchor 220 and can enable positioning of the t-bar proximal leg 228 of the epicardial anchor 220 during implantation. The sleeves 424 can be made of plastic. The guidewire sheath 420 can additionally include a fluoroscopic marker. The anchor sheath 440 can be positioned over the pericardial anchoring system 200 to constrain the pericardial anchoring system 200 until ready for deployment. The anchor sheath distal end 442 of the anchor sheath 440 can be used to engage the t-bar after deployment so as to provide abutment or leverage against the wire frame 222 during the cinching of the pericardial anchor suture 280.

The support sheath 460 can provide control to direct the delivery subsystem 400 to a target location, such as to the left ventricle or the ventricle wall of the left ventricle. The support sheath 460 can provide support, while the pericardial anchoring system is advanced through the ventricle wall, such as advancement of the guidewire 410 or the anchor sheath 440. The support sheath 460 can have at least a distal portion that is compliant. The distal portion of the anchor sheath 440 is operable to advance through the heart wall 41, including the endocardium, the myocardium, and epicardium of the heart wall 41. The anchor sheath 440 can have at least a proximal portion that is more rigid relative to the compliant distal portion, which can provide more control during delivery. The anchor sheath 440 can include a radiopaque marker at the distal end or tip of the anchor sheath 440.

The guidewire sheath 420 can be a thin-walled catheter. The guidewire sheath 420 can include a dilator tip 422 at a distal end of the guidewire sheath 420. The dilator tip 422 can be smooth and tapered to minimize trauma when crossing the heart wall 41. The proximal end of the dilator tip 422 can be tapered to allow the dilator tip 422 to be withdrawn smoothly and minimize trauma during withdrawal of the dilator tip 422 through the heart wall 41.

FIGS. 33-41 are a series of illustrations of a method of providing a pericardial anchor system 200, in accordance with an embodiment.

Figure 33:
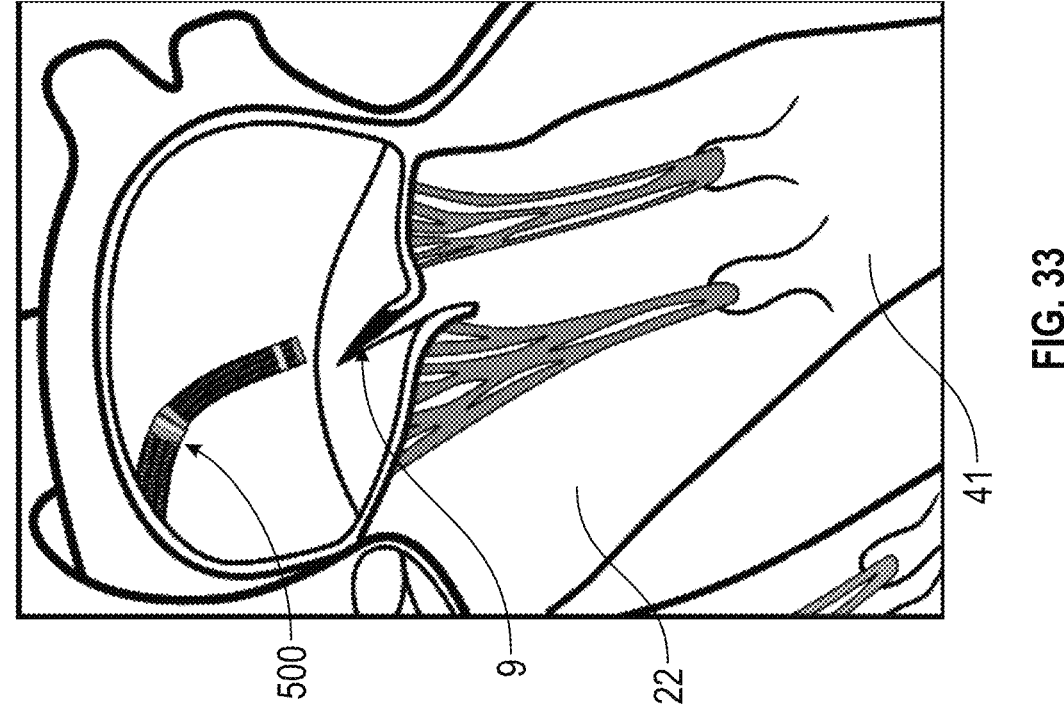
FIG. 33 is a cross-sectional view of a heart with a delivery catheter in accordance with an embodiment of the method of providing a pericardial anchoring system.

FIG. 33 is a cross-sectional view of a heart with a delivery catheter 500 in accordance with an embodiment of the method of providing a pericardial anchoring system 200. A delivery catheter 500 can be positioned in the left atrium. The delivery catheter 500 can be delivered with a transfemoral, transseptal approach.

Figure 34:
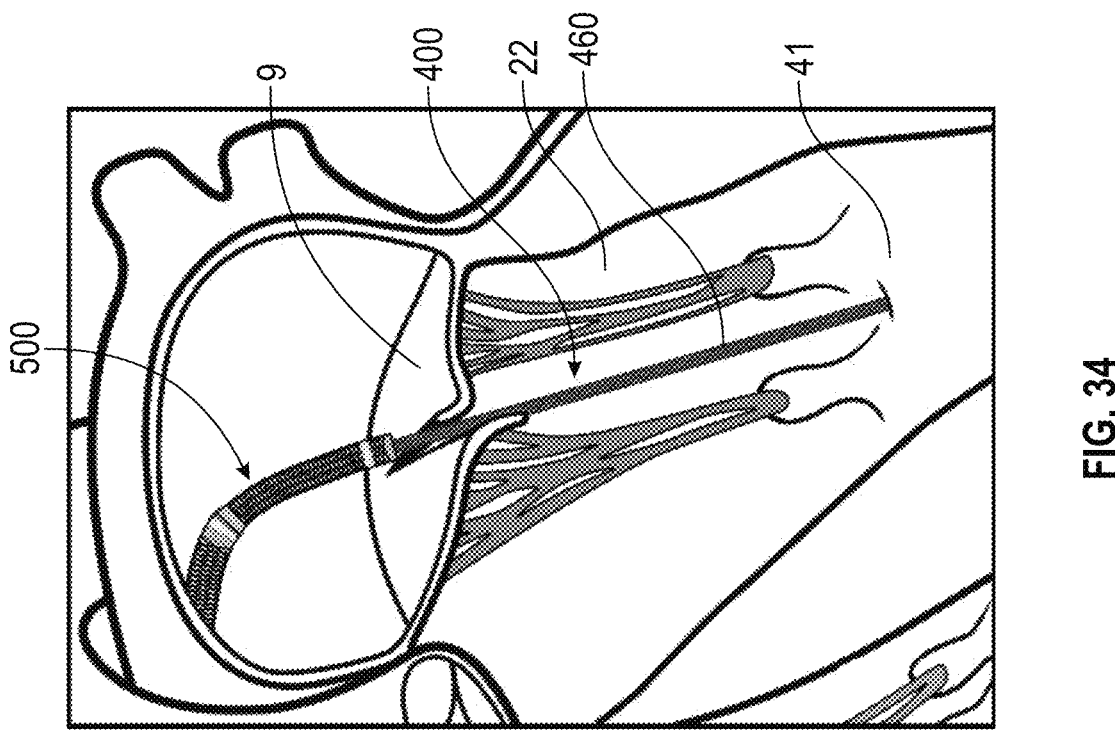
FIG. 34 is a cross-sectional view of the heart with a delivery subsystem for a pericardial anchoring system in accordance with an embodiment of the method of providing a pericardial anchoring system.

FIG. 34 is a cross-sectional view of the heart with a delivery subsystem 400 for a pericardial anchoring system 200 in accordance with an embodiment of the method of providing a pericardial anchoring system 200. The delivery subsystem 400 for the pericardial anchoring system 200 can be delivered through the delivery catheter 500. The delivery subsystem 400 can then be advanced to the target location, such as through the mitral valve and down to the target location at the heart wall 41 between the base of the papillary muscles in the left ventricle. FIG. 35 is a cross-sectional view of the heart wall 41 with the support sheath 460 of the delivery subsystem 400 in accordance with an embodiment of the method of providing a pericardial anchoring system 200. The support sheath 460 of the delivery subsystem 400 for the pericardial anchoring system 200 can be advanced to the heart wall 41 of the left ventricle, as shown in FIGS. 34 and 35.

FIG. 36 is a cross-sectional view of the heart wall 41 with a guidewire 410 of the delivery subsystem 400 in accordance with an embodiment of the method of providing a pericardial anchoring system 200. The guidewire 410 of the of the delivery subsystem 400 can be advanced distally from the distal end of the support sheath 460. The guidewire 410 can puncture the heart wall 41 to be advanced through the heart wall 41, including the endocardium, the myocardium and the epicardium, and be directed into the pericardial space 10. The guidewire 410 is positioned in the pericardial space 10 so that an anchor can subsequently be delivered over the guidewire 410 and into the pericardial space 10. The selection of guidewire stiffness can be optimized, both at distal tip and along entire length, such that, but not limited to, at least the distal tip being stiff enough that it may cross the heart wall 41 and into the pericardial space 10, but soft enough so as to deflect into the pericardial space 10 and not puncture the pericardium (the parietal layer of serous pericardium and fibrous pericardium). The guidewire 410 is operable to turn within the pericardial space 10 and track within the pericardial space 10. Advancement of the distal end of the guidewire 410 within the pericardial space 10 and adjacent to the heart wall 41 may provide the clinician evidence that the distal end of the guidewire 410 is in the pericardial space 10. The deflection of the guidewire 410 into the pericardial space 10 can advantageously provide tactile feedback due to the guidewire 410 popping across the epicardium and subsequent free movement of the guidewire 410 within the pericardial space 10.

Figure 37B:
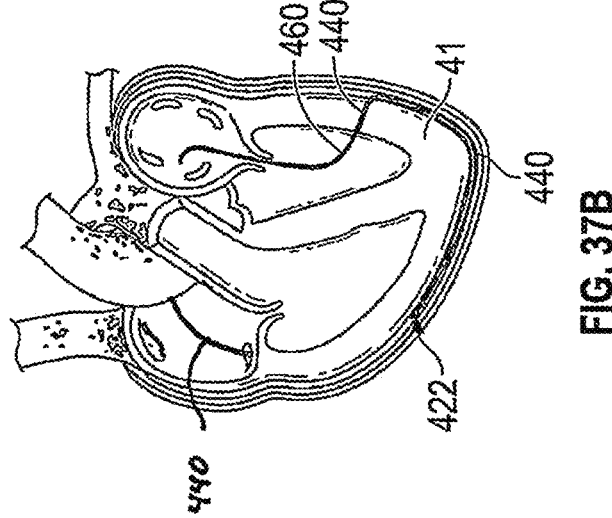
FIG. 37B is a cross-sectional view of the heart with the anchor sheath in accordance with an embodiment of the method of providing a pericardial anchoring system.
Figure 37A:
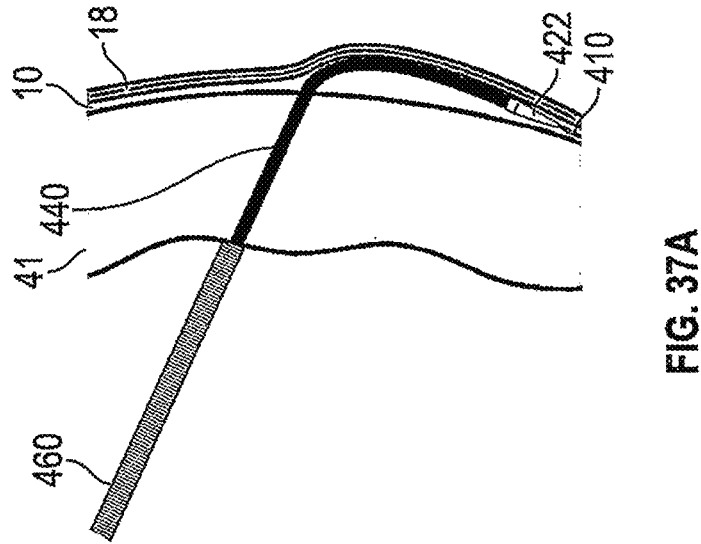
FIG. 37A is a cross-sectional view of the heart wall with an anchor sheath in accordance with an embodiment of the method of providing a pericardial anchoring system.

FIG. 37A is a cross-sectional view of the heart wall 41 with an anchor sheath 440 in accordance with an embodiment of the method of providing a pericardial anchoring system 200. The anchor sheath 440 and the guidewire sheath 420 with the dilator tip 422 can be advanced together distally from the support sheath 460 and over the guidewire 410, through the heart wall 41, including the endocardium, myocardium, and epicardium, and into the pericardial space 10.

FIG. 37B is a cross-sectional view of the heart with the anchor sheath 440 in accordance with an embodiment of the method of providing a pericardial anchoring system 200. The anchor sheath 440 and the guidewire sheath 420 with the dilator tip 422 can be advanced far into the pericardial space 10. The anchor sheath 440 and guidewire sheath 420 can be advanced for a predetermined distance to allow for unsheathing of the epicardial anchor in the predeployed configuration. For example, as shown in FIG. 37B, the anchor sheath 440 and guidewire sheath 420 can be advanced at least 10 cm into the pericardial space 10, and in some embodiments between at least 15 cm or 16 cm into the pericardial space 10. As shown, the anchor sheath 440 and the guidewire sheath 420 can be deployed tangentially in the pericardial space and alongside the heart wall 41. In some examples, the anchor sheath 440 and guidewire sheath 420 can be extended until it is adjacent to the right atrium. The anchor sheath 440 and guidewire sheath 420 can be advanced in a medial/lateral direction or an inferior/superior direction, or a combination thereof. This advantageously does not require extensive or additional expanding or extending the pericardial space itself, as the anchor sheath 440 and guidewire sheath 420 can travel tangentially within the pericardial space 10. The anchor sheath 440 and guidewire sheath 420 are extended at an adequate length to allow for unsheathing of the epicardial anchor 220 in the elongate configuration.

Figure 38:
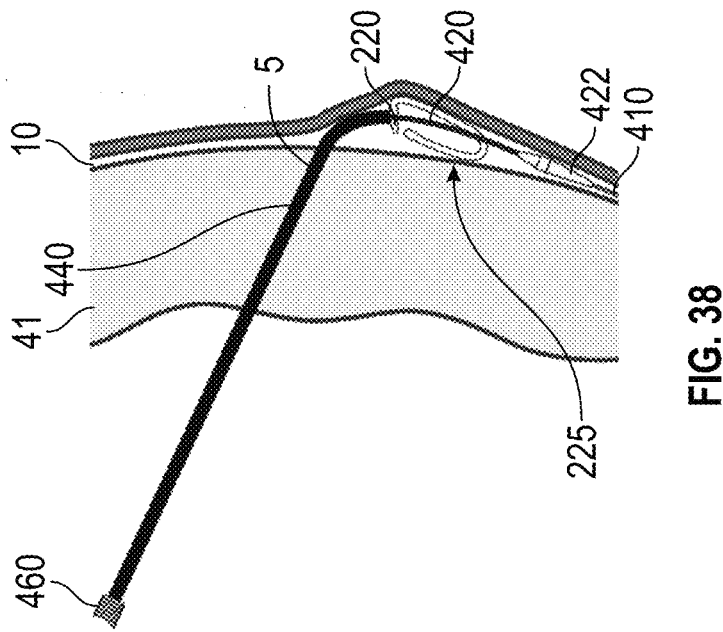
FIG. 38 is a cross-sectional view of the heart wall with the anchor sheath partially retracted to deliver the pericardial anchoring system in accordance with an embodiment of the method of providing a pericardial anchoring system.

FIG. 38 is a cross-sectional view of the heart wall 41 with the anchor sheath 440 partially retracted to deliver the epicardial anchor 220 of the pericardial anchoring system 200 in accordance with an embodiment of the method of providing a pericardial anchoring system 200. With the guidewire sheath 420 maintained in position, the support sheath 460 and the anchor sheath 440 can be retracted together expose the pericardial anchoring system 200, which is positioned between the anchor sheath 440 and the guidewire sheath 420. In some examples, the anchor sheath 440 can be retracted until a marker band on the anchor sheath 440 reaches a marker band on the guidewire sheath 420. This will unsheath the pericardial anchoring system 200. The anchor distal end 225 of the epicardial anchor 220 can be unsheathed initially and begin transitioning (such as curving or coiling) due to the biased or shape memory nature of the biasing element, once it is no longer constrained by the anchor sheath 440. When the epicardial anchor 220 is fully exposed and unsheathed, the proximal leg 228 of the epicardial anchor 220 can be in abutment with the tip of the anchor sheath 440 and the heart wall 41 as the anchor sheath 440 is retracted.

FIG. 38 is a cross-sectional view of the heart wall 41 with the anchor sheath 440 partially retracted to deliver the pericardial anchoring system 200 in accordance with an embodiment of the method of providing a pericardial anchoring system 200. The position of the anchor sheath 440 can then be maintained and the guidewire sheath 420 can be retracted to form a t-bar between the proximal leg 228 of the epicardial anchor 220 and the tip of the anchor sheath 440. Then all sheaths, the support sheath 460, the anchor sheath 440, and the guidewire sheath 420 can be retracted together until the proximal leg 228 is positioned against the puncture in the epicardium. The epicardial anchor 220 can be positioned between the epicardium and the guidewire sheath 420. This can prevent the epicardial anchor 220 from being retracted into the puncture in the epicardium and can maintain the position of the epicardial anchor 220 in the pericardial space.

Figure 39:
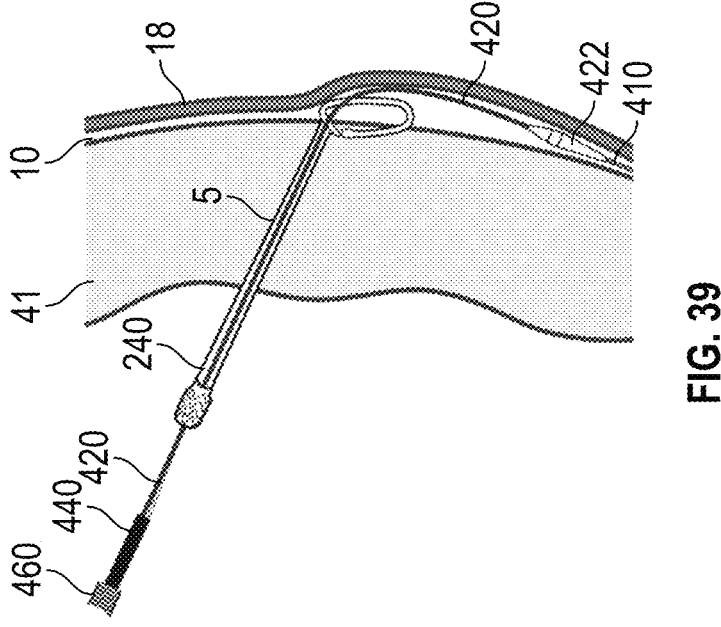
FIG. 39 is a cross-sectional view of the heart wall with the anchor sheath partially retracted to deliver the pericardial anchoring system in accordance with an embodiment of the method of providing a pericardial anchoring system.

FIG. 39 is a cross-sectional view of the heart wall 41 with the anchor sheath 440 partially retracted to deliver the pericardial anchoring system 200 in accordance with an embodiment of the method of providing a pericardial anchoring system 200. The position of the guidewire sheath 420 can then be maintained and the anchor sheath 440 and the support sheath 460 can be retracted together to deploy the transmyocardial pledget 240 and the anchor socket 260. The transmyocardial pledget 240 can be placed in the puncture through the myocardium as the anchor sheath 440 and the support sheath 460. Once the puncture of the myocardium is filled, the remainder or excess length of the transmyocardial pledget 240 can extend proximally from the endocardium, as shown in FIG. 39. The anchor socket 260 can extend proximally from the transmyocardial pledget 240.

Figure 41:
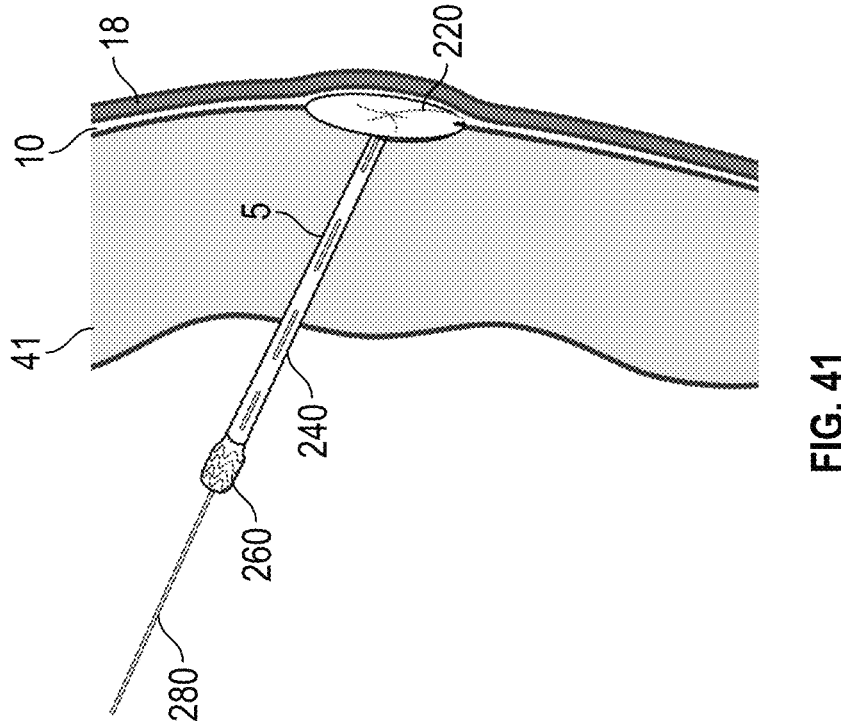
FIG. 41 is a cross-sectional view of the heart wall with the pericardial anchoring system implanted in accordance with an embodiment of the method of providing a pericardial anchoring system.
Figure 40:
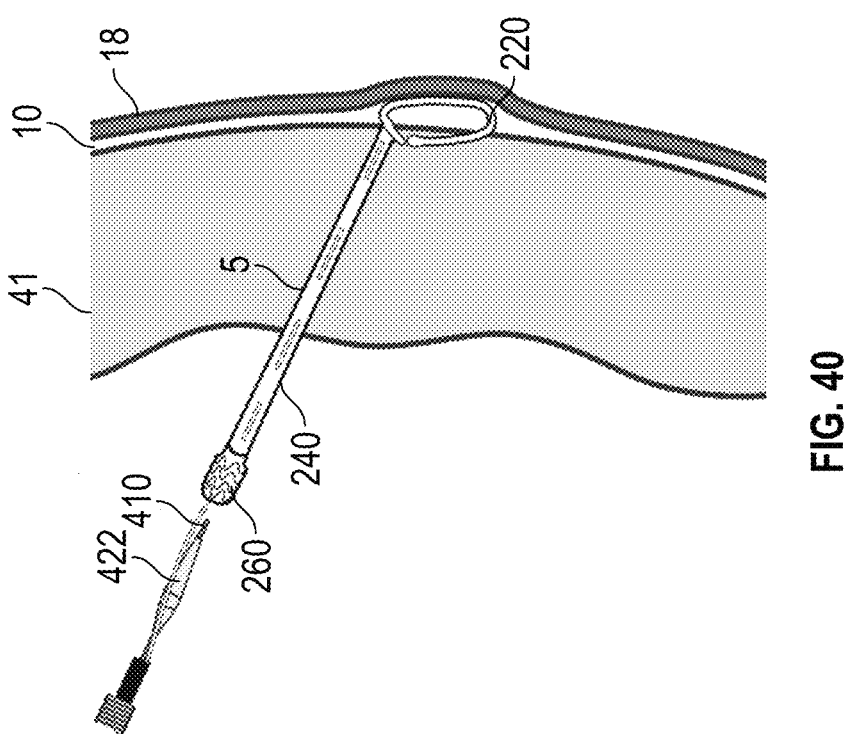
FIG. 40 is a cross-sectional view of the heart wall with the guide wire sheath being retracted to deliver the pericardial anchoring system in accordance with an embodiment of the method of providing a pericardial anchoring system.

FIG. 40 is a cross-sectional view of the heart wall with the guidewire sheath 420 being retracted to deliver the pericardial anchoring system 200 in accordance with an embodiment of the method of providing a pericardial anchoring system 200. The guidewire sheath 420 and guidewire 410 can be retracted to deploy the pericardial anchoring system 200. The guidewire sheath 420, anchor sheath 440, and the support sheath 460 can then all be withdrawn to fully expose the pericardial anchoring system 200. Once the pericardial anchoring system 200 is fully deployed, the pericardial anchor suture 280 can be tensioned to fully coil or curl the epicardial anchor 220. The pericardial anchor suture 280 can also be tensioned to cinch the skirt 230 around the wire frame 222 in the ring configuration, as shown in FIG. 41. This will fully convert the epicardial anchor 220 from the straight configuration in the predeployed state to the coiled configuration in the deployed state.

The epicardial anchor 220 can be constrained in the pre-deployment configuration during delivery, such as by the anchor sheath 440 as shown in FIG. 37A. The epicardial anchor 220 can be delivered and positioned in the pericardial space 10 through the delivery subsystem 400, such as shown in FIGS. 38-39. When the epicardial anchor 220 is positioned in the pericardial space 10 and is released from the anchor sheath 440, the shape memory of the wire frame 222 can begin to convert the epicardial anchor 220 from the elongate configuration in the predeployed state to at least a partially coiled configuration. The distal end of the epicardial anchor 220 with the distal eyelet 224 in the straight configuration is initially released from the anchor sheath 440. The anchor distal end 225, as shown in FIG. 21, is a free end of the epicardial anchor 220 that can begin to transition (such as curl or coil) as it exits from the anchor sheath 440 and is no longer constrained by the anchor sheath 440. However, the limited space of the pericardial space 10 can constrain the epicardial anchor 220 and prevent it from reaching a fully curved or coiled configuration in a deployed configuration. The remainder of the epicardial anchor 220, through the proximal leg 228, is then released from the anchor sheath 440 as the anchor sheath 440 is further retracted from the guidewire sheath 420. The remainder of the pericardial anchor system 200 can be released from the anchor sheath 440, including the transmyocardial pledget 240 and the anchor socket 260. The pericardial anchor suture 280 of the pericardial anchor system 200 can then be tensioned to fully coil the epicardial anchor 220 and cinch the skirt 230 of the epicardial anchor 220, which can fully convert the epicardial anchor 220 to a fully coiled configuration in the deployed state. The epicardial anchor 220 can be positioned against the epicardial puncture.

FIG. 41 is a cross-sectional view of the heart wall 41 with the pericardial anchor system 200 implanted in accordance with an embodiment of the method of providing a pericardial anchor system 200. As shown, the fully coiled epicardial anchor 220 can be positioned in the pericardial space 10 and against the epicardial puncture to seal the epicardial puncture. At least a portion of the transmyocardial pledget 240 can fill the punctures of the endocardium, myocardium, and endocardium. The remainder of the transmyocardial pledget 240 can extend proximally from the epicardial puncture. The anchor socket 260 can extend proximally from the transmyocardial pledget 240. As will be discussed further below, the remainder of the transmyocardial pledget 240 can be collapsed down or folded to be positioned against the puncture of the endocardium to seal the puncture of the endocardium.

Figures 50, 51, 52:
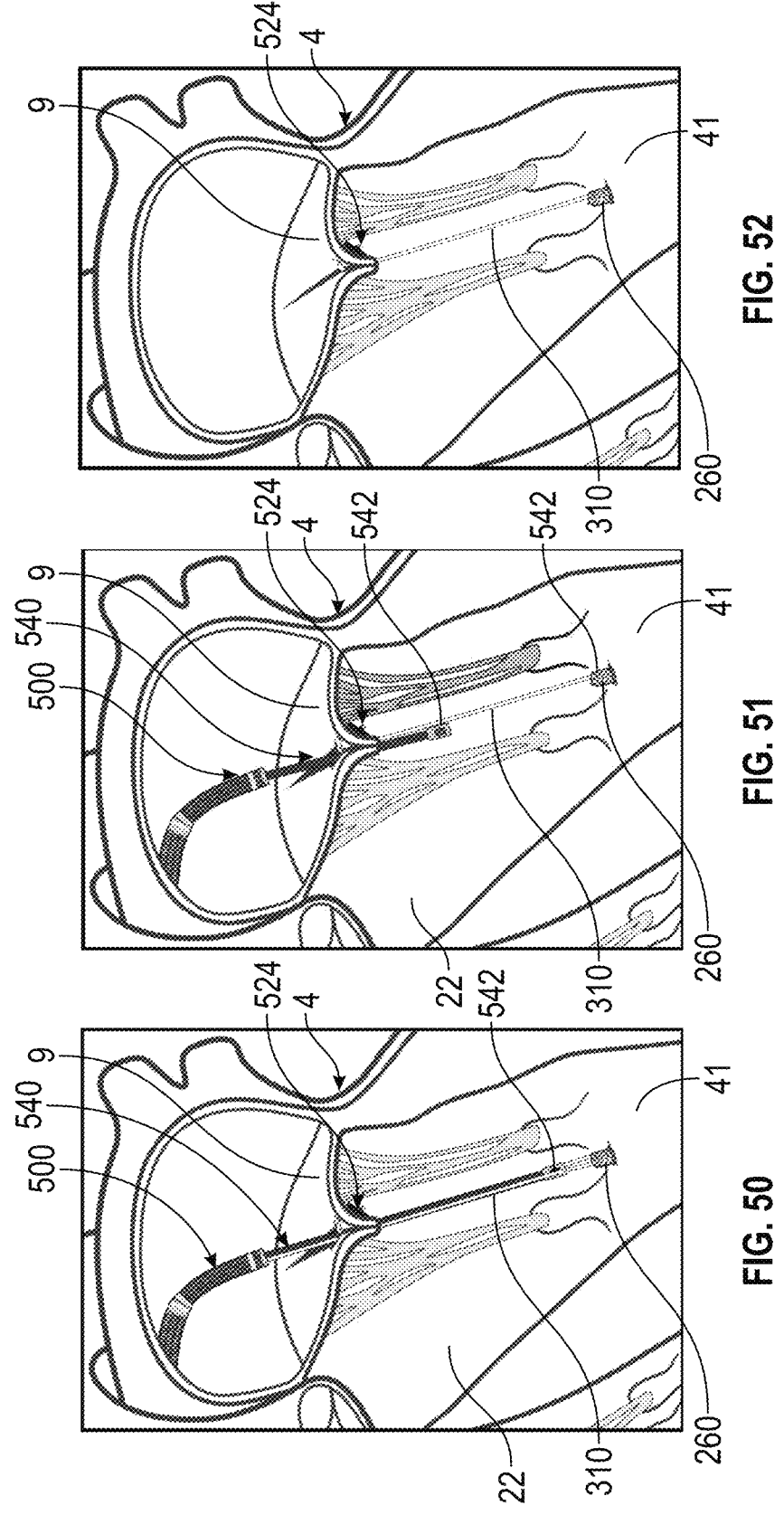
FIG. 50 is a cross-sectional view of the heart with a suture cutter.
FIG. 51 is a cross-sectional view of the heart with a suture cutter being withdrawn.
FIG. 52 is a cross-sectional view of the heart with the delivery catheter being withdrawn.

In accordance with an embodiment, the pericardial anchoring system 200 may be used to control the motion of a mitral valve leaflet by coupling the pericardial anchor suture 280 to one or more leaflet anchor sutures 310, also referred to as tethers, that are themselves coupled to the mitral valve leaflet 9. After the epicardial anchor 220 is delivered to the target location, the pericardial anchor suture 280 may be coupled to the mitral valve leaflet 9, as shown in FIG. 52, by use of a leaflet anchoring system 510. The leaflet anchoring system 510 includes a leaflet anchor 300 and a leaflet anchor suture 310 which is operable to pass through the mitral valve leaflet 9 and couple thereto.

FIGS. 42-46 are a series of illustrations of an embodiment of a leaflet anchoring system 510 and illustrates an embodiment of a method of providing leaflet tethering using the pericardial anchoring system 200 in combination with the leaflet anchoring system 510. In some examples, this method of providing leaflet tethering can be provided multiple times, such that a plurality of leaflet tethers can be provided. In some examples, the leaflet anchoring system 510 may be used to pass the leaflet anchor suture 310 through the mitral valve leaflet 9 multiple times, in accordance with an embodiment.

Figures 42, 43, 44:
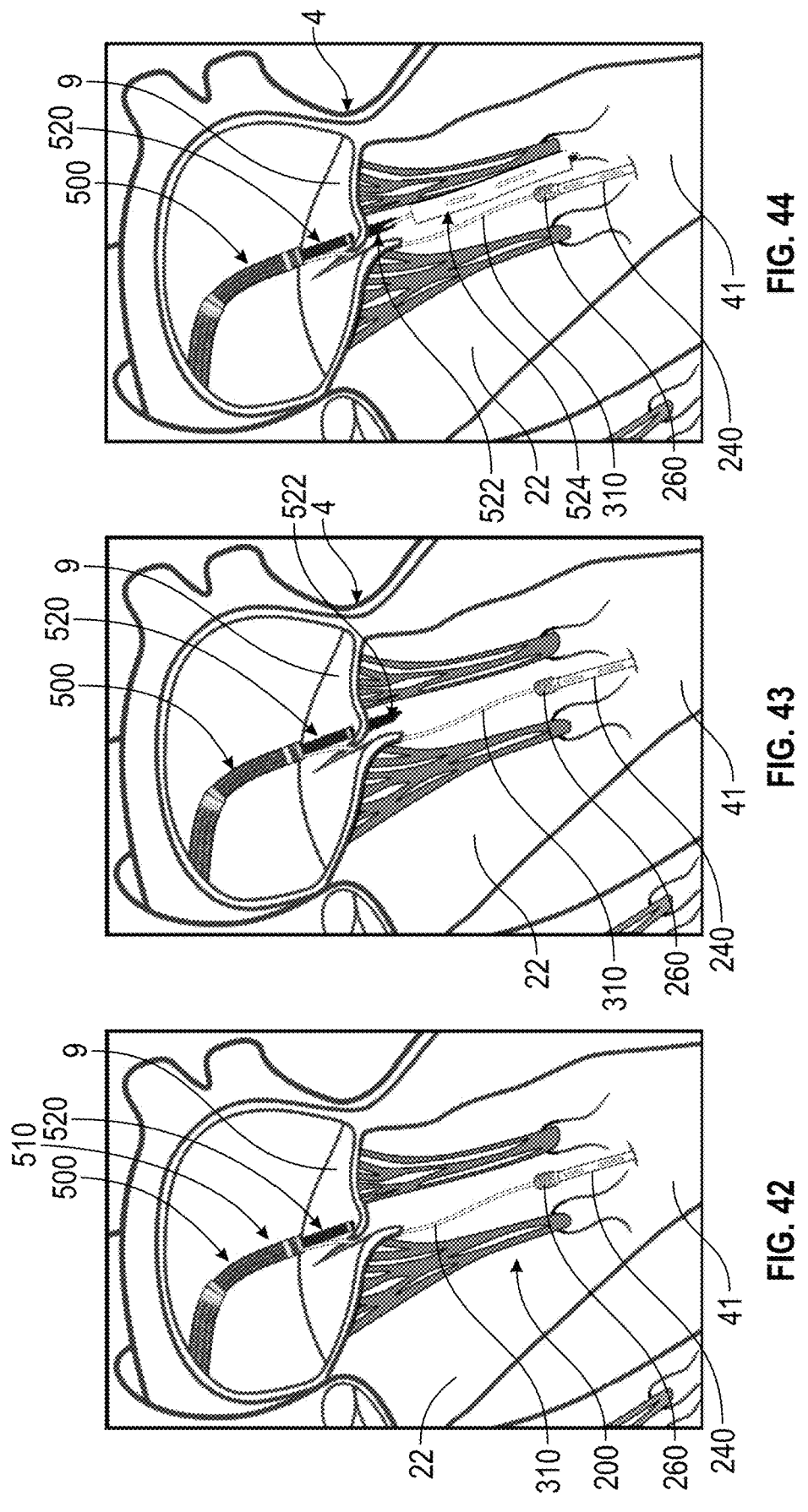
FIG. 42 is a cross-sectional view of the heart with a delivery subsystem for a leaflet anchoring system in accordance with an embodiment of the method of providing a leaflet anchoring system.
FIG. 43 is a cross-sectional view the heart with a needle in accordance with an embodiment of the method of providing a leaflet anchoring system.
FIG. 44 is a cross-sectional view the heart with a leaflet anchor in accordance with an embodiment of the method of providing a leaflet anchoring system.

FIG. 42 is a cross-sectional view of a heart 4 showing the delivery subsystem 520 operable with a leaflet anchoring system 510 in accordance with an embodiment of a method of providing leaflet tethering using the pericardial anchoring system 200. A delivery subsystem 520 for a leaflet anchor system 510 can be delivered via the delivery catheter 500. The delivery subsystem 520 can be positioned adjacent a first side of the leaflet 9, such as, but not limited to, an atrial side of the leaflet 9.

FIG. 43 is a cross-sectional view the heart 4 showing a needle 522 of the leaflet anchoring system 510, in accordance with an embodiment. The delivery subsystem 520 can deliver the needle 522 which can be positioned adjacent a first side of the leaflet 9. The needle 522 can be extended to puncture through the leaflet 9 to extend from the first side of the leaflet 9 to a second side of the leaflet 9, such as, but not limited to, the atrial side to a ventricle side of the leaflet 9.

Figures 45, 46, 47:
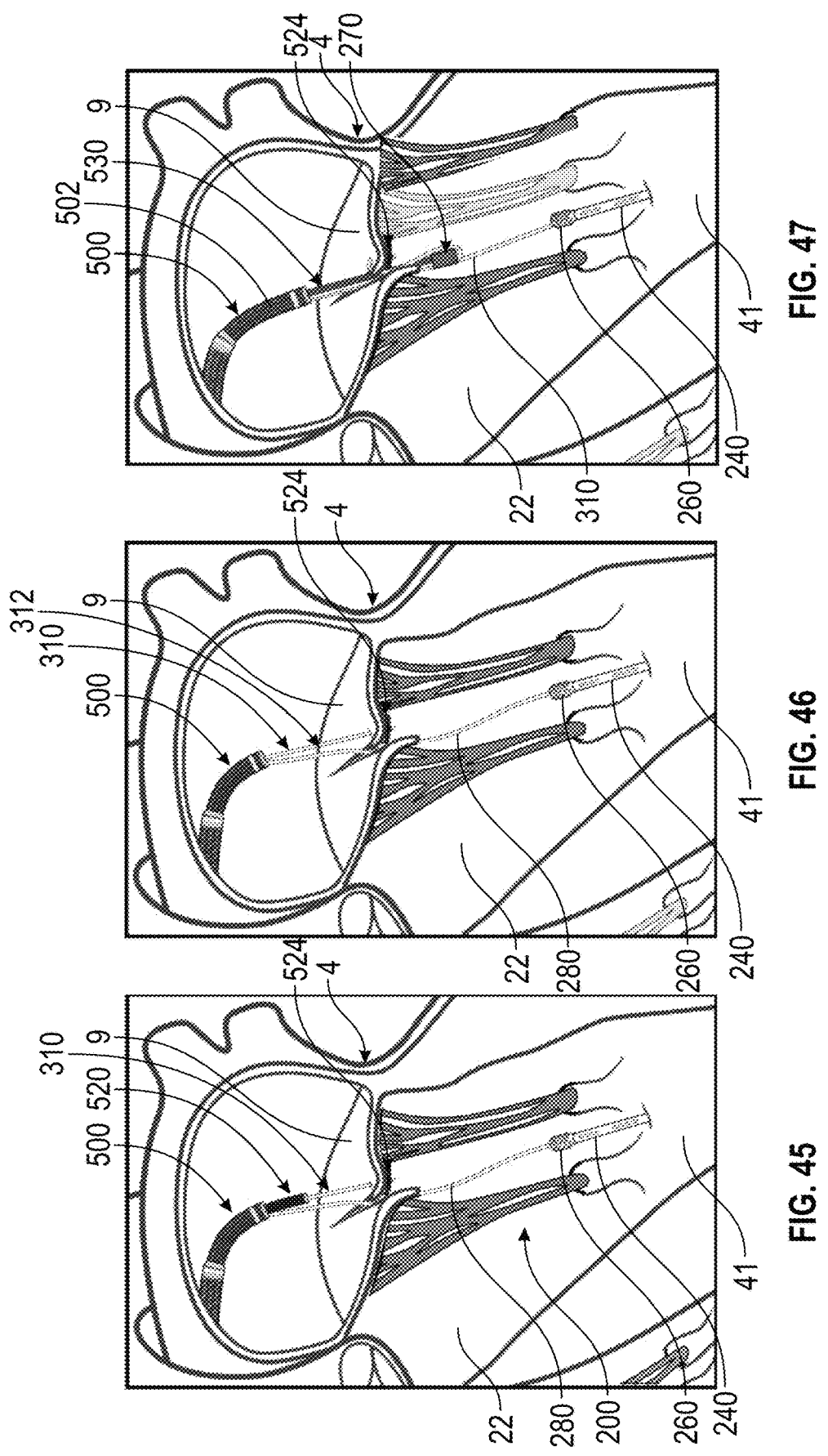
FIG. 45 is a cross-sectional view the heart with a leaflet anchor in accordance with an embodiment of the method of providing a leaflet anchoring system.
FIG. 46 is a cross-sectional view the heart with the delivery subsystem for a leaflet anchoring system withdrawn.
FIG. 47 is a cross-sectional view of the heart with a delivery subsystem for a suture lock.

FIG. 44 is a cross-sectional view the heart 4 showing a leaflet anchor 524 in accordance with an embodiment. The leaflet anchor 524 can be delivered through the needle 522, such that the leaflet anchor 524 extends from a distal end of the needle 522. In an embodiment, the leaflet anchor system 312 includes a leaflet anchor suture 310 and a leaflet anchor 524, such as, but not limited to a leaflet anchor 300, as shown in FIGS. 23 and 46. In accordance with an embodiment, as shown in FIG. 44, the leaflet anchor 524 is a leaflet anchor 300 which is coupled to the leaflet anchor suture 310, such as, but not limited to, by being integrated with or weaved through the leaflet anchor 300 and extending from the leaflet anchor 300 to the leaflet anchoring system 312. Embodiments of the leaflet anchor 524 also include, and not limited to, a knot, a stitch, a staple, adhesive, and a suture clip.

FIG. 45 is a cross-sectional view the heart 4 with the leaflet anchor 524 in accordance with an embodiment. The leaflet anchor suture 310 can be tensioned to collapse or fold the leaflet anchor 524, in this embodiment, the leaflet anchor 300, against the second side of the leaflet 9. The leaflet anchor 300 is operable to cinch into a compress configuration when tension is applied to the leaflet anchor suture 310 and is operable to prevent the leaflet anchor 300 from pulling through the puncture in the leaflet 9 from which it extends.

FIG. 46 is a cross-sectional view the heart 4 with the delivery subsystem 520 for the leaflet anchoring system 312 having been withdrawn. The delivery subsystem 520 can be withdrawn through the delivery catheter 500.

Once the leaflet anchoring system 312 is deployed to the target location in the leaflet 9, a suture lock 270 can be provided to lock the leaflet anchor suture 310 from the pericardial anchor system 200 and the leaflet anchor suture 310 from the one or more leaflet anchors 524 provided in the leaflet 9. FIGS. 47-49B are a series of illustrations of a method of providing a suture lock, in accordance with an embodiment. The suture lock 270 is operable to couple the respective sutures.

FIG. 47 is a cross-sectional view of the heart 4 with a suture lock delivery subsystem 530 operable for deployment of the suture lock 270. The suture lock delivery subsystem 530 for the suture lock 270 can be delivered through a delivery catheter distal end 502 of the delivery catheter 500, positioned in the right atrium in this embodiment, but not limited thereto. The suture lock 270 can be delivered to engage the pericardial anchor suture tail 313 from the pericardial anchor suture 280, shown in FIG. 21, and the one or more leaflet anchor suture tails 319 from the one or more leaflet anchor sutures 310, as shown in FIG. 23. The pericardial anchor suture 280 is tensioned to provide predetermined tension between the pericardial anchor system 200 and the leaflet anchor 524. The suture lock 270 can then be locked to maintain the desired tension.

Figures 48A, 48B, 49A, 49B:
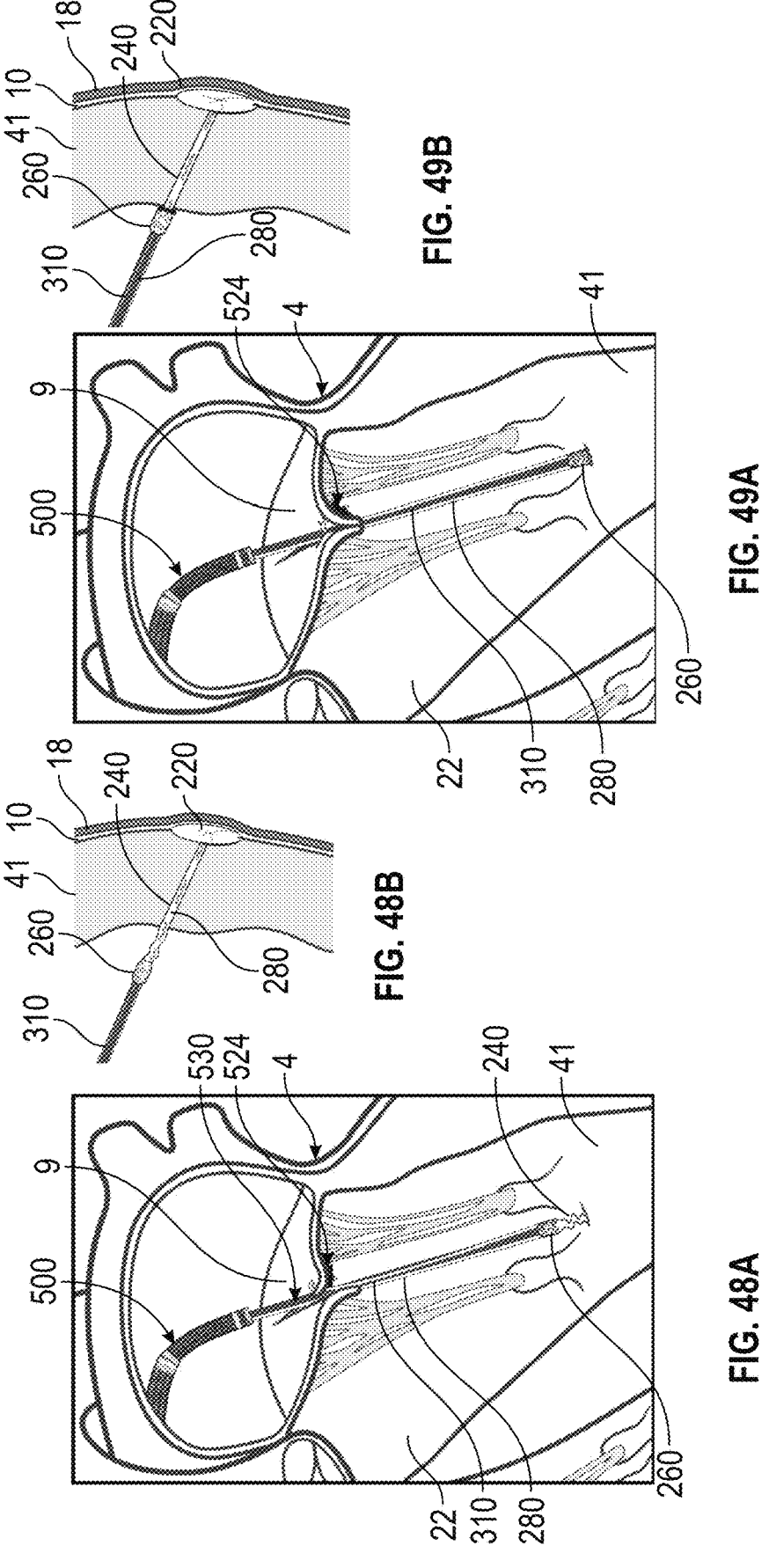
FIG. 48A is a cross-sectional view of the heart with a suture lock positioned in an anchor socket of the pericardial anchoring system.
FIG. 48B is a cross-sectional view of the heart wall with the suture lock positioned in an anchor socket of the pericardial anchoring system.
FIG. 49A is a cross-sectional view of the heart with the anchor socket of the pericardial anchoring system positioned against the heart wall.
FIG. 49B is a cross-sectional view of the heart wall with the pericardial anchoring system.

FIG. 48A is a cross-sectional view of the heart 4 with a suture lock 270 positioned in an anchor socket 260 of the pericardial anchoring system 200. The suture lock 270 can then be positioned within the anchor socket 260 using the pericardial anchor suture 280 as a rail to guide the suture lock 270 to the anchor socket 260. In accordance with an embodiment, the ventricular anchor and leaflet anchor sutures are fed through the suture lock and the suture lock is tracked down to the ventricular anchor by using the ventricular anchor suture as a rail. The transmyocardial anchor is accordioned in the process of bringing the lock down to the heart wall. The sutures are locked together after a predetermined tension has been applied to the leaflet anchor to correct the valve leaflet function. In accordance with another embodiment, the anchor suture is tensioned, the transmyocardial anchor pledget is cinched, the leaflet anchors are tensioned and then the sutures are coupled together. FIG. 48B is a cross-sectional view of the heart wall 41 with the suture lock 270 positioned in an anchor socket 260 of the pericardial anchoring system 200.

FIG. 49A is a cross-sectional view of the heart 4 with the anchor socket 260 of the pericardial anchoring system 200 positioned against the heart wall 41, in accordance with an embodiment. In accordance with an embodiment, the pericardial anchoring system 200 does not include an anchor socket 260, wherein the suture lock 270 is operable to affect tissue ingrowth. FIG. 49B is a cross-sectional view of the heart wall 41 with the pericardial anchoring system 200. The suture lock 270 positioned in the anchor socket 260 can be further lowered down to be positioned against the heart wall 41 which in turn can fold down or collapse the excess length of the transmyocardial pledget 240 down to the heart wall 41. The suture lock 270 positioned within the anchor socket 260 can be positioned against the folded down portion of the transmyocardial pledget 240. The suture lock 270 enclosed by the anchor socket 260 can drive the anchor socket 260 to the endocardial surface, which can also encourage sealing of the puncture on the endocardial surface by the folded down portion of the transmyocardial pledget 240. As shown in FIGS. 49A-49B, a portion of the transmyocardial pledget 240 is collapsed and compressed between the suture lock 270 positioned in the anchor socket 260 and the heart wall 41. The suture lock delivery subsystem 530 to deliver the suture lock 270 can then be withdrawn through the delivery catheter 500.

Once the suture lock 270 is delivered to the target location in the anchor socket 260, a suture cutter 542 can be provided to cut the suture tails of the one or more leaflet anchor sutures 310 and the suture tail of the pericardial anchor suture 280. FIGS. 50-52 are a series of illustrations of a method of providing a suture cutter, in accordance with an embodiment. FIG. 50 is a cross-sectional view of the heart with a suture cutter 542. A delivery subsystem 540 can be provided and delivered through the delivery catheter 500. The delivery subsystem 540 can be a catheter configured to extend distally from the delivery catheter 500. The delivery subsystem 540 can provide and deliver a suture cutter 542. The suture cutter 542 can be railed down over the sutures 280, 310 towards the suture lock 270. The suture cutter 542 can cut the excess suture tails of the sutures 280, 310, after the sutures 280, 310 have been tensioned by the suture lock

270. FIG. 51 is a cross-sectional view of the heart with a suture cutter 542 being withdrawn. The suture cutter 542 can then be withdrawn from the heart through the delivery catheter 500. FIG. 52 is a cross-sectional view of the heart with the delivery catheter being withdrawn. The delivery catheter 500 can then be withdrawn from the heart.

Figure 53B:
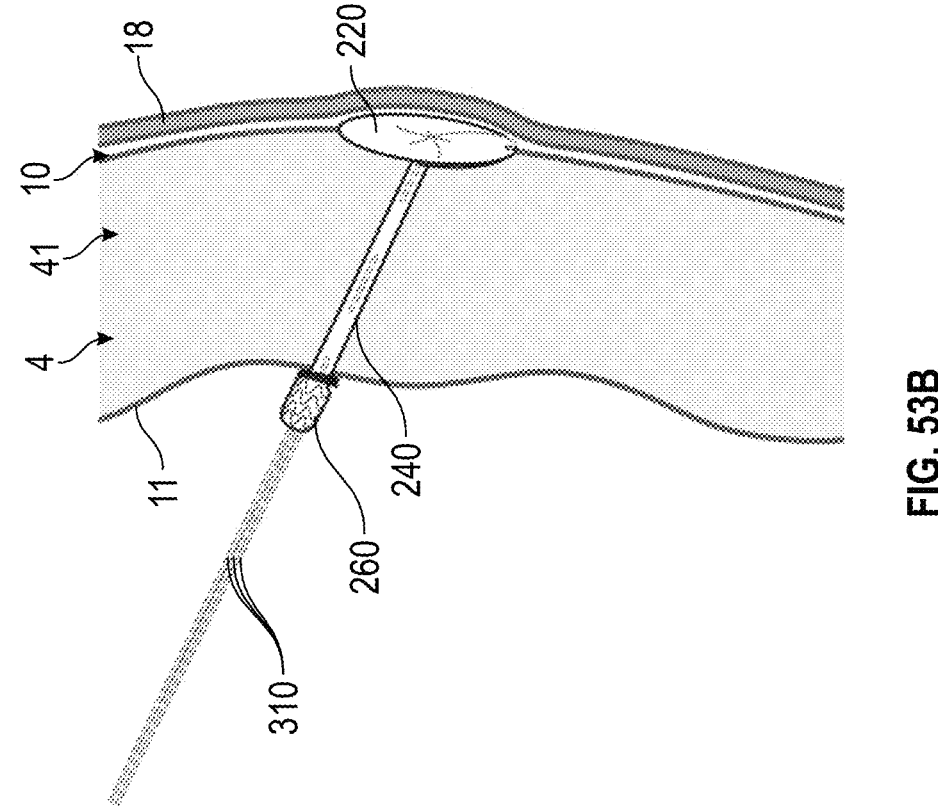
FIG. 53B is a cross-sectional view of the heart with multiple leaflet anchor sutures.
Figure 53A:
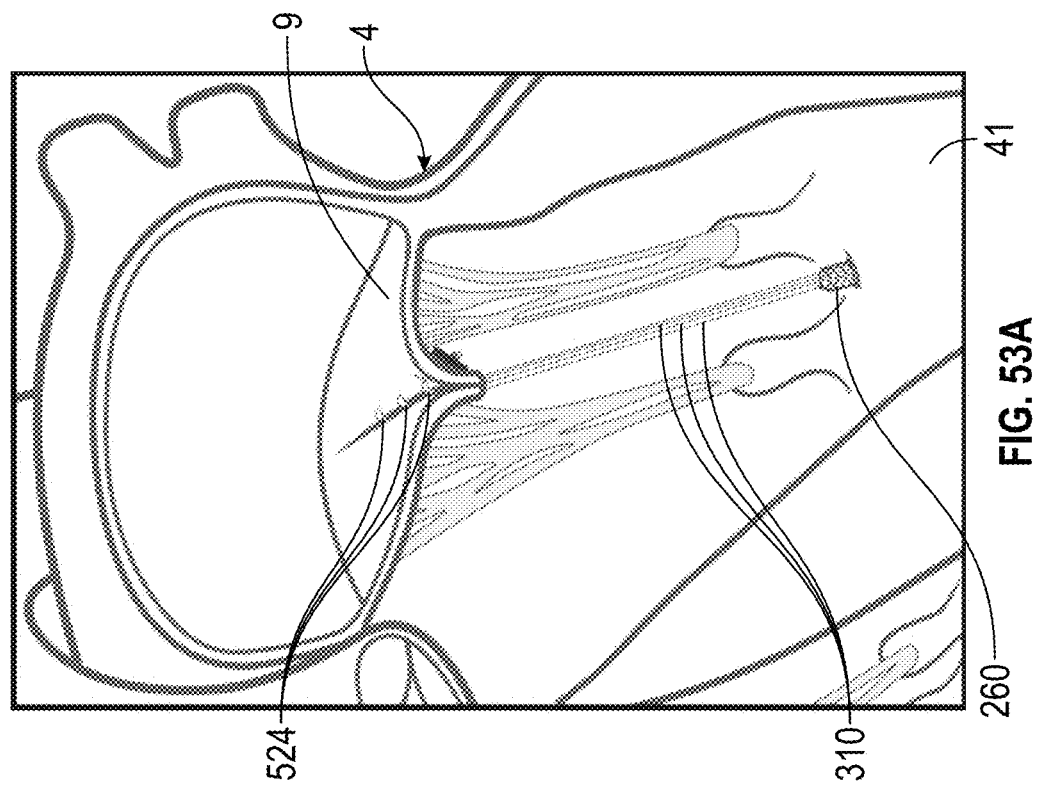
FIG. 53A is a cross-sectional view of the heart with multiple leaflet anchors.

FIG. 53A is a cross-sectional view of the heart with multiple leaflet anchors 524 provided. FIG. 53B is a cross-sectional view of the heart with multiple leaflet anchor sutures 310. As previously described, multiple leaflet anchors 524 can be provided and implanted in the leaflet 9. Each of the multiple leaflet anchors 524 can have a leaflet anchor suture 310 connected to the pericardial anchor system 200 as described herein.

In accordance with other embodiments, the present disclosure relates to apparatus, systems and methods for placing hardware, devices, or therapies into the pericardial space from the ventricular side of the heart. Although the present disclosure discusses the embodiments herein with respect to a patient's endovascular location and ventricles, the embodiments are applicable to placement into the pericardial space from many approaches, including improvements on current methods performed percutaneously from outside the chest or abdomen.

The tool, when used for placement of a device or therapy into the pericardial space, the present disclosure may be performed with echocardiography and/or fluoroscopy, and deployment of the tool and its use may be permanent or reversible.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

The present disclosure relates to systems and methods for placing hardware, devices, or therapies into the pericardial space from the heart's ventricles using an endovascular approach. This placement may be necessary when therapies for the treatment of valve disease, ventricular dilatation, ischemic heart disease, congenital lesions, heart failure, or structural heart disease are needed. In accordance with an embodiment, a pericardial access and fixation tool, referred herein as a tool, is provided operable for deployment into the myocardium and extending into the pericardial space from the ventricular side of the heart. These embodiments enable traversing of the myocardium with minimization of risk or degree of myocardial injury, bleeding, or placement in untoward places.

FIGS. 54A and 54B are side and cross-sectional views, respectively, of the tool 150, in accordance with an embodiment. Embodiments of the tool 150 may be used with a catheter-based delivery system, referred to as a delivery catheter system 50, of a small caliber (approximately 0.018" diameter), but can be larger or smaller with the same components specific to the intended use. In accordance with an embodiment, tool 150 includes a body 170 and a head 160, wherein the body 170 is operable to be deployed within the myocardium and the head 160 is operable to extend from the myocardium into the pericardial space 10. In accordance with an embodiment, the head 160 includes movable elements. In accordance with an embodiment, these movable elements are operable to expand the pericardial space 10 during and/or after deployment of the tool 150. In accordance with an embodiment, these movable elements are operable to anchor the tool 150 in the pericardial space 10 after placement. In accordance with an embodiment, the body 170 defines a lumen 172, and the head 160 defines an eyelet(s) 124 in fluid communication with the lumen 172, wherein the lumen 172 and eyelet 174 are operable to provide fluid communication between the ventricle 22 and the pericardial space 10. The combination of the lumen 172 and eyelet(s) 124 is referred to as an access channel 176. In accordance with an embodiment, the access channel 176 that is operable to provide fluid communication between the ventricle 22 and the pericardial space 10 is operable to facilitate confirmation of placement of the tool 150 in the pericardial space 10, as well for the passage of wires, catheters, or devices into the pericardial space 10 from the ventricle side of the heart 2.

In accordance with an embodiment, the access channel 176 may include an occluding element 175 operable to occlude or stop the fluid communication through the access channel 176. In accordance with an embodiment, the eyelet 174 comprises a resilient material operable to open under an abutment force of an object passing through the lumen 172 or fluid or gas pressure, and operable to close the fluid communication with the lumen 172 when the object or fluid or gas pressure is not present at the eyelet 174. In another embodiment, the eyelet 174 further includes a flap operable to open under an abutment force of an object or fluid or gas pressure, and operable to close the fluid communication with the lumen 172 when the object or fluid or gas pressure is not present at the eyelet 174.

In accordance with embodiments, the movable members 161 may be anchor expander members 162 and/or anchor apposition members 164.

The anchor expander members 162 are operable to provide a graduated crossing profile in a predeployed configuration and buttress the parietal pericardium when the anchor expander members 162 are expanded or moved to a deployed configuration.

The anchor apposition members 164 are operable to provide a graduated crossing profile in a predeployed configuration and buttress against the visceral pericardium 19 when the anchor apposition members 164 and expanded or moved to a deployed configuration in the pericardial space 10. In accordance with an embodiment, the movable members 161 are operable to function as both an anchor expander member 162 and anchor apposition member 164, that is, they are one of the same.

The body 170 is operable to occupy the traversing segment 28 after crossing of the myocardium so as to maintain hemostasis. As will be discussed below, the heart wall 4 is pierced by a needle 56 and/or the tool 150 from the ventricle side to the pericardial space 10 side so as to deploy the tool 150 therebetween. That pierced or formed heart wall channel in the heart wall 4 is referred herein as the traversing segment 28.

The tool 150 further includes a retention element 180 that is operable to retain the tool 150 within the heart wall 4 and/or as a means for coupling to other therapeutic devices. In accordance with an embodiment, the retention element 180 is a biocompatible cord or similar member to which a therapeutic device (e.g., valve repair, heart failure repair, or replacement prosthesis) may be coupled.

FIG. 55B is a cross-sectional view of the tool 150 showing an actuation mechanism 58 operable to extend and/or retract the movable members 161, in accordance with an embodiment. In accordance with an embodiment, the actuation mechanism 58 is a cable or lever member that is operable to lift the movable members 161 for movement into the deployed configuration once the head 160 have been placed in the desired position. These movable members 161 are operable to serve as anchors after deployment, in accordance with an embodiment.

The delivery catheter system 50 is operable to deliver the tool to the desired location. The delivery catheter system 50, in accordance with an embodiment, includes a steerable catheter(s) 51, 53 that may accept a delivery catheter(s) 55 that are operable to place and deploy the tool 150 with the body 170 in the heart wall 4 and the head 160 extending therefrom and in the pericardial space 10. FIG. 54C is a cross-sectional view of the left ventricle 22 and mitral valve 8, illustrating the delivery catheter system 50 for placement of the tool 150, in accordance with an embodiment. The delivery catheter system 50 includes steerable catheters 51, 53 that have been placed from a transvenous, transseptal approach to cross the mitral valve into the left ventricle 22, followed by pericardial access. Each of these steerable catheters 51, 53 contain cables for steering in multiple directions in order to achieve perpendicularity to the myocardium or a trajectory preferred for the therapy to be implanted as shown in FIG. 54D which is a cross-sectional view of the left ventricle 22 illustrating the delivery catheter distal end 52. The delivery catheter system 50 can be either single, in series, or in telescoped arrangement. While the figures show a transvenous, transseptal approach, the delivery catheter system 50 and tool 150 can similarly be used using a transatrial or transaortic approach. Similarly, the delivery catheter system 50 can be inserted from either atria and either ventricle 22 into the pericardial space 10.

In accordance with embodiments, the delivery catheter system 50 includes a guidewire 54 and a needle 56, singularly or in combination, operable to provide support for traversing the myocardium and piercing the visceral pericardium 19. The needle 56 may be coupled to or integrated with a guidewire 54 that can be advanced into the pericardial space 10 after the visceral pericardium 19 is pierced, in order to facilitate subsequent catheter exchanges, as shown in FIG. 55B.

FIGS. 55A-55I illustrate the sequence for delivery of the tool 150 using the delivery catheter system 50, in accordance with an embodiment. FIG. 55A is a cross-sectional view of the heart 2 illustrating the delivery catheter system 50 located adjacent to the endocardium 11, in accordance with an embodiment. As shown in FIG. 55A, the steerable guide catheter 55 is steered to the target site and opposed to the surface of the endocardium 11. The trajectory is established through steering of the different steerable catheters 51, 53, 55, with confirmation on echocardiography, fluoroscopy, or other comparable imaging method.

The tool 150 is then advanced through the myocardium 13. FIG. 55B is a cross-sectional view of the heart 2 illustrating the tool 150 traversing the endocardium 11 and myocardium 13 with the assistance of a needle 56 for placement in the myocardium 13 and pericardial space 10 during a deployment process, in accordance with an embodiment. This advancement can be aided by the needle 56, as well as use of electrical energy, cryoablation, radiofrequency, or mechanical force. In at least one embodiment, the tool 150 utilizes a mechanical method with the needle 56 for traversing the myocardium with a stylet to reduce tissue coring. In at least one other embodiment, the tool 150 uses radiofrequency energy or cautery. In at least one other embodiment, the tool 150 has a beveled or non-beveled sharp end that facilitates traversing, with or without a supporting needle 56 or guidewire 54. In at least one other embodiment, rotation of the tool 150 facilitates traversing of the myocardium. These embodiments enable traversing of the myocardium with minimization of risk or degree of myocardial injury, bleeding, or placement in untoward places. The tool 150 is advanced to the visceral pericardium 19, which is slowly traversed.

FIG. 55C is a cross-sectional view of the heart 2 illustrating the tool 150 traversing the epicardium 14 for placement in the myocardium 13 and pericardial space 10 during a deployment process, in accordance with an embodiment. Once the visceral pericardium 19 is traversed, the eyelet 174 is positioned in the pericardial space 10 without traversing the parietal pericardial layer. This positioning is enabled by the bluntness of the tip of the tool 150, the relatively stiff compliance of the parietal pericardial layer, and potential space between the visceral pericardium 19 and parietal layers. In at least once embodiment, signals from the eyelet 174, such as by, but not limited to, hydrostatic pressure or electrical impedance, are monitored to determine when the visceral pericardium 19 has been crossed and the head 160 of the tool 150 resides in the pericardial space 10. FIG. 55D is a cross-sectional view of the heart 2 illustrating the tool 150 enlarging the pericardial space 10 during a deployment process, in accordance with an embodiment. In accordance with an embodiment, confirmation of location can also be obtained through injection of contrast or imaging substances, as shown in FIG. 55D. Injection of these substances can help expand the pericardial space 10 as the tool 150 is being advanced.

In some embodiments, the eyelet 174 facilitates confirmation of placement in the pericardial space 10, as well as passage of wires, catheters, or devices into the pericardial space 10. The eyelet 174 can be used to transduce hydraulic or mural pressure as well as deliver contrast or visualizing agents. The eyelet 174 can also be used to inject material into and expand the pericardial space 10 (e.g., a gas, fluid, or mechanical expander) to facilitate subsequent device placement. In at least one embodiment, the eyelet 174 is at the distal end of the tool 150, facing towards the pericardial space 10 in either an orthogonal, perpendicular, or oblique orientation relative to the pericardial planes. In at least one embodiment, the eyelet 174 may be positioned more proximal or along a length of the head 160 of the tool 150. In other embodiments, the eyelet 174 may be oval, circular, square, rectangular or another geometric shape and size. In other embodiments, the eyelet 174 may be multiple in number, some or all of which are in fluid communication with one or more lumens 172 in the body 170.

FIG. 55E is a cross-sectional view of the heart 2 illustrating the movable elements of the tool 150 enlarging the pericardial space 10 during a deployment process, in accordance with an embodiment. As shown in FIG. 55E, once the tool 150 has been advanced into the pericardial space 10, the anchor expander members 162 are released, either via retraction of retention cables or similar elements, or unsheathing, in accordance with embodiments. These anchor expander members 162 are operable to create more bluntness and force to push on the parietal pericardial layer, in order to expand the pericardial space 10. This expansion enables larger elements to be advanced into the pericardial space 10 as needed.

In some embodiments, the tool 150 contains movable elements that help expand the pericardial space 10 as the tool 150 is being advanced. In at least one embodiment, the head 160 defines these movable elements to reside at or near the distal end of the tool 150 and are controlled by cables or push/pull rods. In at least one embodiment, the movable elements contribute to expansion of the pericardial space 10 as well as anchoring.

FIG. 55F is a cross-sectional view of the heart 2 illustrating the movable elements of the tool 150 engaging the epicardium 14 and/or the pericardium 18 so as to anchor the tool 150 in the pericardial space 10, in accordance with an embodiment. As shown in FIG. 55F, the anchor expander members 162 can be expanded or retracted with advancement of the tool 150 to create more space in the pericardial space 10. Once the head 160 of the tool 150 is positioned in the pericardial space 10, the anchor apposition members 164 are expanded or deployed as shown in FIG. 55G. FIG. 55G is a cross-sectional view of the heart 2 illustrating the movable elements of the tool 150 engaging the epicardium 14 and/or the pericardium 18 so as to anchor the tool 150 in the pericardial space 10, in accordance with an embodiment. The head 160 of the tool 150, in including the movable elements, can be retracted, rotated, or recaptured for position on the surface of the visceral pericardium 19 (i.e., epicardial). FIG. 55H is a top view of the head 160 illustrating the placement of the movable members 161, in this embodiment the expanded anchor apposition member 164 and the anchor expander members 162, in the deployed configuration, in accordance with an embodiment.

Once a satisfactory position is obtained, the epicardial anchoring tool 150 tool 150 is decoupled from the delivery catheter system 50. The tool 150 is retained by the engagement of the retention element 180 in cooperative engagement with the head 160 of the tool 150, leaving the tool 150 within the myocardium and extending into the pericardial space 10 for use. In accordance with an embodiment, the eyelet 174 may be closed so as to prevent fluid communication between the ventricle 22 and the pericardial space 10 with an occluding element 175.

FIGS. 56A1-56D2 show different configurations of the anchor expander members 162 and anchor apposition members 164. They may be symmetrical, asymmetric, have different lengths, be concave or convex, have different pads and sizes, and be offset or perpendicular.

In some embodiments, similar methods described herein for the use of the tool 150 to access the pericardial space 10 can also be used to place devices, anchors, or therapies on the surface of the parietal pericardium.

Inventive features of this disclosure have been described above both generically and with regard to specific embodiments. It will be apparent to those skilled in the art that various modifications and variations can be made in the embodiments without departing from the scope of the disclosure. Thus, it is intended that the embodiments cover the modifications and variations of this disclosure provided they come within the scope of the appended claims and their equivalents.

What is claimed is:

1. A mitral valve chord repair system, comprising:
   a pericardial anchoring system, comprising:
     an epicardial anchor comprising a skirt and a pericardial anchoring suture coupled to the skirt;
     a transmyocardial pledget extending from the skirt and coupled to the pericardial anchoring suture;
     wherein the epicardial anchor is configured to be transformable between a predeployed configuration and a deployed configuration, in the deployed configuration the epicardial anchor being in a coiled configuration and the transmyocardial pledget being in a collapsed configuration;
     a socket coupled to the transmyocardial pledget;

at least one leaflet anchor coupled to a leaflet anchoring suture; and a suture lock configured to secure the pericardial anchoring suture and the leaflet anchoring suture;

wherein the socket is configured to constrain and dock the suture lock.

2. A pericardial anchoring system, comprising:

an epicardial anchor comprising a skirt and a pericardial anchoring suture coupled to the skirt;

a transmyocardial pledget extending from a proximal portion of the epicardial anchor and coupled to the pericardial anchoring suture;

a suture lock configured to secure the pericardial anchoring suture; and a socket coupled to the transmyocardial pledget and configured to constrain and dock the suture lock, wherein the epicardial anchor is configured to be transformable between a predeployed configuration and a deployed configuration, in the deployed configuration the epicardial anchor being in a coiled configuration and the transmyocardial pledget being in a collapsed configuration.

3. The pericardial anchoring system of claim 2, wherein the epicardial anchor is configured to form a disc shape in the deployed configuration.

4. The pericardial anchoring system of claim 2, wherein the predeployed configuration comprises an elongate configuration, and wherein the deployed configuration comprises a compressed configuration.

5. The pericardial anchoring system of claim 2, wherein the predeployed configuration comprises an elongate configuration.

6. The pericardial anchoring system of claim 2, wherein the epicardial anchor has a free end in the predeployed configuration, wherein the epicardial anchor is configured to coil beginning from the free end of the epicardial anchor to form the deployed configuration.

7. The pericardial anchoring system of claim 2, wherein the epicardial anchor further comprises a wire frame, wherein the wire frame is covered with the skirt.

8. The pericardial anchoring system of claim 7, wherein the wire frame of the epicardial anchor has a shape memory property that is shape-set to the deployed configuration.

9. The pericardial anchoring system of claim 7, wherein the skirt of the epicardial anchor is coupled to the wire frame along an edge defining a length, wherein the skirt comprises a plurality of apertures along an edge of the skirt opposite the wire frame, wherein the pericardial anchoring suture is alternately weaved through the plurality of apertures, and wherein the pericardial anchoring suture is operable to be tensioned so as to cinch the skirt into the deployed configuration.

10. The pericardial anchoring system of claim 7, wherein the wire frame of the epicardial anchor further comprises a proximal leg, wherein the proximal leg is configured to remain straight and positioned in a center of the epicardial anchor in the deployed configuration.

11. The pericardial anchoring system of claim 10, wherein the transmyocardial pledget extends from the proximal leg of the epicardial anchor.

12. The pericardial anchoring system of claim 10, wherein the proximal leg includes two portions of a common wire that is doubled up, such that the two portions are parallel to each other.

13. The pericardial anchoring system of claim 10, wherein the epicardial anchor is transformable between the predeployed configuration to the deployed configuration at least partially due to proximal retraction of the pericardial anchoring suture.

14. The pericardial anchoring system of claim 7, wherein the epicardial anchor is transformable between the predeployed configuration to the deployed configuration at least partially due to a shape memory property of the wire frame that is shape-set to the deployed configuration.

15. The pericardial anchoring system of claim 7, wherein a first end of the wire frame and a second end of the wire frame each comprises a nontraumatic end.

16. The pericardial anchoring system of claim 15, wherein the nontraumatic end of each of the first end of the wire frame and the second end of the wire frame comprises an eyelet.

17. The pericardial anchoring system of claim 2, wherein the skirt is configured to slidingly receive the pericardial anchoring suture, and wherein the pericardial anchoring suture is operable to be tensioned so as to cinch the skirt into the deployed configuration.

18. The pericardial anchoring system of claim 2, wherein the transmyocardial pledget comprises a film with a tubular structure.

19. The pericardial anchoring system of claim 18, wherein the pericardial anchoring suture is weaved through a plurality of apertures through the film of the transmyocardial pledget.

20. The pericardial anchoring system of claim 2, further comprising at least one leaflet anchor coupled to a leaflet anchor suture, wherein the suture lock is configured to secure the pericardial anchoring suture and the leaflet anchor suture.

21. A pericardial anchoring system, comprising:

an epicardial anchor comprising a skirt including a reinforced portion;

a pericardial anchoring suture including an end fixedly coupled to the reinforced portion of the skirt; and a transmyocardial pledget extending from the skirt and coupled to the pericardial anchoring suture;

wherein the epicardial anchor is configured to be transformable between a predeployed configuration and a deployed configuration, in the deployed configuration the epicardial anchor being in a coiled configuration and the transmyocardial pledget being in a collapsed configuration.

* * * * *